United States Patent [19]

Jacquesy et al.

[11] Patent Number: 5,561,119

[45] Date of Patent: Oct. 1, 1996

[54] GLYCOSYLATED PRODRUGS, THEIR METHOD OF PREPARATION AND THEIR USES

[75] Inventors: Jean-Claude Jacquesy, Buxerolles; Jean-Pierre Gesson, Chasseneuil-du-Poitou; Claude Monneret, Paris; Martine Mondon, Poitiers; Brigitte Renoux, Saint-Julien-l'Ars; Jean-Claude Florent, Les Ulis; Michel Koch, La-Celle-Saint-Cloud; François Tillequin, Paris, all of France; Hans H. Sedlacek, Marburg, Germany; Manfred Gerken, Marburg, Germany; Cenek Kolar, Marburg, Germany; Gilbert Gaudel, Paris, France; Klaus Bosslet, Marburg, Germany; Jörg Czech, Marburg, Germany; Dieter Hoffman, Marburg, Germany; Gerhard Seemann, Marburg, Germany; Hans-Ulrich Schorlemmer, Marburg, Germany; Gerhard Dickneite, Marburg, Germany

[73] Assignees: Laboratoires Hoechst, Puteaux, France; Behringwerke A.G., Marburg, Germany

[21] Appl. No.: 137,167

[22] PCT Filed: Apr. 29, 1992

[86] PCT No.: PCT/FR92/00385

§ 371 Date: May 27, 1994

§ 102(e) Date: May 27, 1994

[87] PCT Pub. No.: WO92/19639

PCT Pub. Date: Nov. 12, 1992

[30] Foreign Application Priority Data

Apr. 30, 1991 [FR] France .................. 91 05326

[51] Int. Cl.⁶ .................. A61K 31/70; A61K 39/44; C07C 50/18; C07H 5/04
[52] U.S. Cl. .................. 514/34; 536/6.4; 536/18.2; 536/18.4; 536/18.5; 536/17.4; 536/17.7; 424/146.1; 424/155.1; 424/178.1; 424/179.1; 424/183.1; 556/465
[58] Field of Search .................. 424/146.1, 155.1, 424/178.1, 179.1, 183.1; 536/6.4, 18.2, 18.4, 18.5, 17.4, 17.7; 514/34; 556/465

[56] References Cited

U.S. PATENT DOCUMENTS 4,035,566 7/1977 Israel et al. .................. 536/6.4
4,952,394 8/1990 Senter .................. 424/181.1
4,975,278 12/1990 Senter et al. .................. 424/178.1

FOREIGN PATENT DOCUMENTS

| 0410366 | 1/1991 | European Pat. Off. . |
| 3935016 | 4/1991 | Germany . |
| 3077872 | 4/1991 | Japan . |
| 81/01145 | 4/1981 | WIPO . |
| 88/07378 | 10/1988 | WIPO . |
| 90/07929 | 7/1990 | WIPO . |

OTHER PUBLICATIONS

Tanino et al. *Tetrahedron Letters* 1992, 33(10), 1337–40.
Jain et al. *Indian J. Chem., Sect. B*, 1988, 27B(11), 1019–23.
Heslin et al. *J. Chem, Soc., Perkin Trans.* 1988, 1(6), 1417–23.
Nakatani et al. *Agric. Biol. Chem.* 1987, 51(10), 2727–32.
Collington et al. *Tetrahedron Letters* 1985, 26(5), 681–4.
Gray et al. *Helv. Chim. Acta* 1977, 60(4), 1304–11.
Levai et al. *Acta Chim. Acad. Sci. Hung.* 1975, 84(1), 99–107.
De Bruyne et al. *Carbohydr. Res.* 1974, 33(1), 117–25.

*Primary Examiner*—Gary L. Kunz
*Assistant Examiner*—Kathleen Kahler Fonda
*Attorney, Agent, or Firm*—Oblon, Spivak, McClelland, Maier & Neustadt, P.C.

[57] ABSTRACT

Glycosylated prodrugs, a preparation method therefor, and their use with tumor-specific immunoenzymatic conjugates for the treatment of cancer, are described. These anthracycline prodrugs have formula (I).

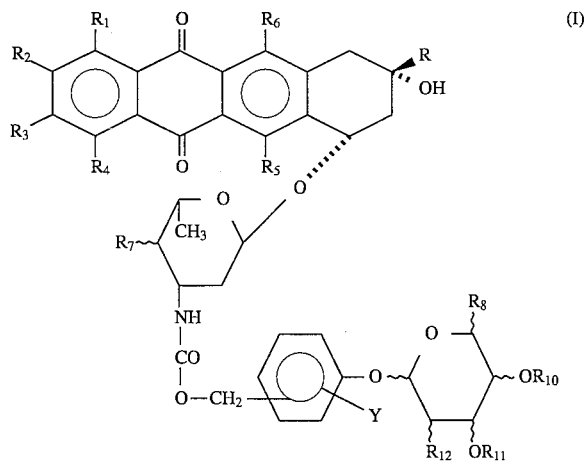

36 Claims, 3 Drawing Sheets

GLYCOSYLATED PRODRUGS, THEIR METHOD OF PREPARATION AND THEIR USES

BACKGROUND OF THE INVENTION

1. Field of the Invention

The present invention relates to glycosylated prodrugs, to a method of preparing them and to their uses, alone or with tumor-specific immunoezymatic conjugates, particularly in the treatment of cancer.

More specifically, the present invention relates to prodrugs comprising modified anthracyclines which can be cleaved, in particular, by the action of said tumor-specific immunoenzymatic conjugates to give cytotoxic substances which are active towards tumoral cells.

2. Discussion of the Background

The combination of a prodrug with enzyme/monoclonal antibody conjugates as therapeutic agents has been described in the literature. In general, the antibodies in question, which are directed against a specific tissue and are covalently bonded to an enzyme capable of cleaving the prodrug, are first injected into an appropriate animal, especially man, after which a prodrug is administered which can be activated by the enzyme. The prodrug is converted to a cytotoxin by the action of the enzyme/antibody conjugate anchored to the specific tissue, the cytotoxin exerting a cytotoxic effect on said tissue.

International patent application WO 81/01145, in the name of UNIVERSITY OF ILLINOIS FOUNDATION, describes prodrugs which can be activated by hydrolytic enzymes, and defines five criteria for the optimum efficacy of a prodrug: (1) there must be sufficient activating enzyme in the region of the tumor for cytotoxic levels of antitumoral agent to be released in the region of the tumor, (2) the prodrug must not be activated in regions other than that of the tumor, (3) the prodrug must be an appropriate substrate for the enzyme associated with the tumor, under physiological conditions, (4) the prodrug must be non-toxic or much less toxic than the activated antitumoral agent, and (5) the activated substance must have a short biological half-life so that the toxic effects are limited to the tumor.

More specifically, said patent application states that antitumoral agents can be made specific for a tumor by the addition of a peptide converting said agent to a prodrug which is pharmacologically inactive, but can be selectively activated only at the site of the tumor by an enzyme present in large amounts in the region of the tumor (plasmin and plasminogen activator in particular). The amino acid sequence of the peptide part of the prodrug is such that it will be cleaved enzymatically from the antitumoral agent part by proteases such as plasmin or plasminogen activator, so as to release the antitumoral agent in its active form in the region of the tumor.

The prodrugs which can be activated by hydrolytic enzymes can have a structure in which the peptide and the antitumoral part are covalently bonded via a self-sacrificing connector whose molecular structure is such that the enzymatic cleavage of the peptide from the self-sacrificing connector will spontaneously cause the cleavage of its bond with the antitumoral part.

However, the prodrugs described in said International patent application can only be used for cancers which cause an increased production of enzymes, and more particularly proteases, at the site of the tumor; now, these activating enzymes capable of cleaving the prodrugs described in said patent application are not found in sufficient amounts in human cancers, so these prodrugs do not afford the desired selective toxicity (K. D. BAGSHAWE, Br. J. Cancer, 1987, 56, 531).

International patent application WO 88/07378, in the name of CANCER RESEARCH CAMPAIGN TECHNOLOGY LTD, describes a therapeutic system containing on the one hand an enzyme/antibody conjugate and on the other hand a prodrug which can be activated by the enzyme. The antibody of the enzyme/antibody conjugate recognizes a tumor-specific antigen and the enzyme is capable of converting the prodrug to a cytotoxic agent.

Said patent application states that it is preferable to use enzymes other than mammalian enzymes, so as to prevent the premature release of cytotoxic agent by endogenous enzymes.

More specifically, said patent application describes modified nitrogen mustards such as p-bis-N-(2-chloroethyl)aminobenzylglutamic acid and its derivatives) which can be converted to nitrogen mustards in the presence of carboxypeptidases, and anthracyclines in which the terminal amino group is converted to an amide in the presence of an amino acid.

However, these prodrugs have the major disadvantage of retaining considerable intrinsic cytotoxicity.

European patent application 302 473 also describes a therapeutic system which contains two components and in which the enzyme/antibody conjugate located on the tumoral tissue cleaves a prodrug to give a cytotoxic active compound. More specifically, the enzyme/antibody conjugates contain alkaline phosphatase (AP), penicillin V amidase (PVA) or cytosine deaminase (CD) and are used in association with 4'-phosphate etoposide and its derivatives (or 7-(2-aminoethyl phosphate)mitomycin), with N-(p-hydroxyphenoxyacetyl)adriamycin or with 5-fluorocytosine, respectively, as the prodrug.

However, the system described in said patent application has the disadvantage of utilizing either a circulating enzyme, namely alkaline phosphatase, which is capable of activating the prodrug early in the circulation, or an exogenous enzyme (PVA or CD), which is capable of giving rise to intolerance phenomena or sensitization phenomena.

International patent application WO 90/07929, in the name of AKZO NV, describes a site-specific method of activating a prodrug in vivo in an animal by using a conjugate of an activator and a target-specific substance, the activator part of which enables the prodrug to be converted to a pharmacologically active substance. The activator is especially an enzyme of human origin, such as lysozyme, which is absent in the circulation or present in very small amounts, and whose natural substrates are also absent in the circulation or on the surface of the non-target cells. The target-specific substance is especially an antibody directed against a tumor-specific antigen. In particular, the prodrug can comprise an anthracycline (for example doxorubicin) modified by a chitin oligomer bonded to the anthracycline by an amino group at the carbonyl $C_{13}$ on the anthracycline or on the glycosylated part.

However, the system proposed in said International patent application has especially the major disadvantage of releasing not doxorubicin itself but a derivative thereof, namely Dox-(GlcNAc)$_1$ or Dox-(GlcNAc)$_5$; on the one hand this is not therefore a prodrug in the strict sense, and on the other hand, as far as these derivatives are concerned, there is a lack of accumulated knowledge from both the pharmacological and the toxicological point of view.

It is apparent from the above that the main disadvantages of the systems of the prior art are:

1) as regards the choice of enzyme:
   the undesired cleavage of the prodrug (circulating enzyme);
   the cleavage of the prodrug associated with the production of a large amount of enzyme at the site of the tumor; and
   the use of exogenous enzymes capable of giving rise to intolerance phenomena or sensitization phenomena; and
2) as regards the choice of prodrug:
   the intrinsic cytotoxicity of the prodrug;
   the production of an anthracycline derivative whose pharmacological and toxic effects are not sufficiently well known; and
   the use of a prodrug with two compartments (substrate for the enzyme+cytotoxic agent), which has the disadvantage of giving rise to steric or electronic interference with the enzymatic cleavage reaction.

The Applicant consequently set out to provide prodrugs capable of being converted to pharmacologically active substances in the presence of an appropriate enzymatic conjugate, which meet practical needs better than the prodrugs of the prior art, especially in that they are stable, in that they do not give rise to steric or electronic interference during the enzymatic cleavage reaction, and in that they deliver the active cytotoxic substance only at the site of the tumor.

SUMMARY OF THE INVENTION

The present invention relates to anthracycline prodrugs, characterized in that they have formula I below:

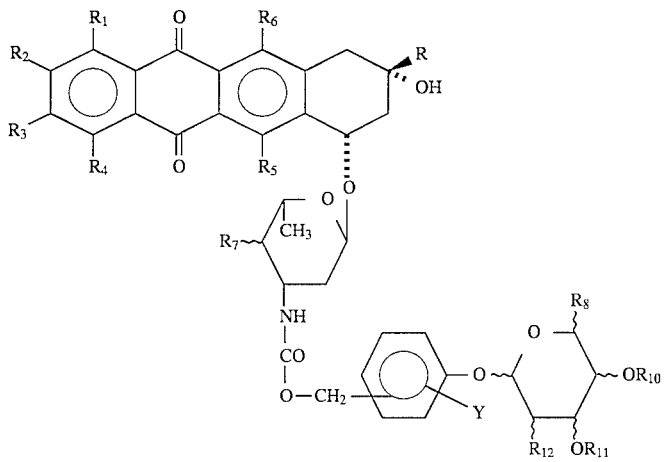

(I)

in which $R_1$, $R_2$ and $R_3$, which can be identical or different, are a hydrogen atom or a hydroxyl group;

$R_4$ is a hydrogen atom, a hydroxyl group or a methoxy group;

R is a group CO—CH$_2$—R", in which R" is a hydrogen atom, a C$_2$-C$_6$ alkyl group, a hydroxyl group, an alkoxy group, an O-acyl group or an aryl group;

$R_5$ and $R_6$, which can be identical or different, are a hydrogen atom or a hydroxyl group;

$R_7$ is a hydrogen atom or a hydroxyl group;

$R_8$ is a group —CH$_2$—OR$_9$ or a group COOR$_9$, where R$_9$ is a C$_1$-C$_3$ alkyl or a hydrogen atom;

$R_{10}$ and $R_{11}$ are a hydrogen atom, an acyl protecting group or an alkyl group;

$R_{12}$ is a hydroxyl group, an amine group, an amide group or an O-acyl protecting group;

the benzyl —CH$_2$ is preferably in the para or ortho position to the glycosyl oxygen; and Y is a hydrogen atom, or at least one electron-attracting group selected especially from the group comprising the NO$_2$ group, a halogen atom and a group SO$_2$X (where X=—CH$_3$, C$_6$H$_4$-CH$_3$, NH$_2$, N—(C$_1$-C$_4$ alkyl)$_2$ or NH—C$_1$-C$_4$ alkyl), —CN, acyl or COO-alkyl, and/or at least one electron-donating group selected from the group comprising groups of the type O-alkyl, NHCO-alkyl, N(alkyl)CO-alkyl, S-alkyl or alkyl.

In terms of the present invention, acyl and alkyl groups are understood as meaning groups comprising from 1 to 6 carbon atoms.

DETAILED DESCRIPTION OF THE PREFERRED EMBODIMENTS

Figure 1:
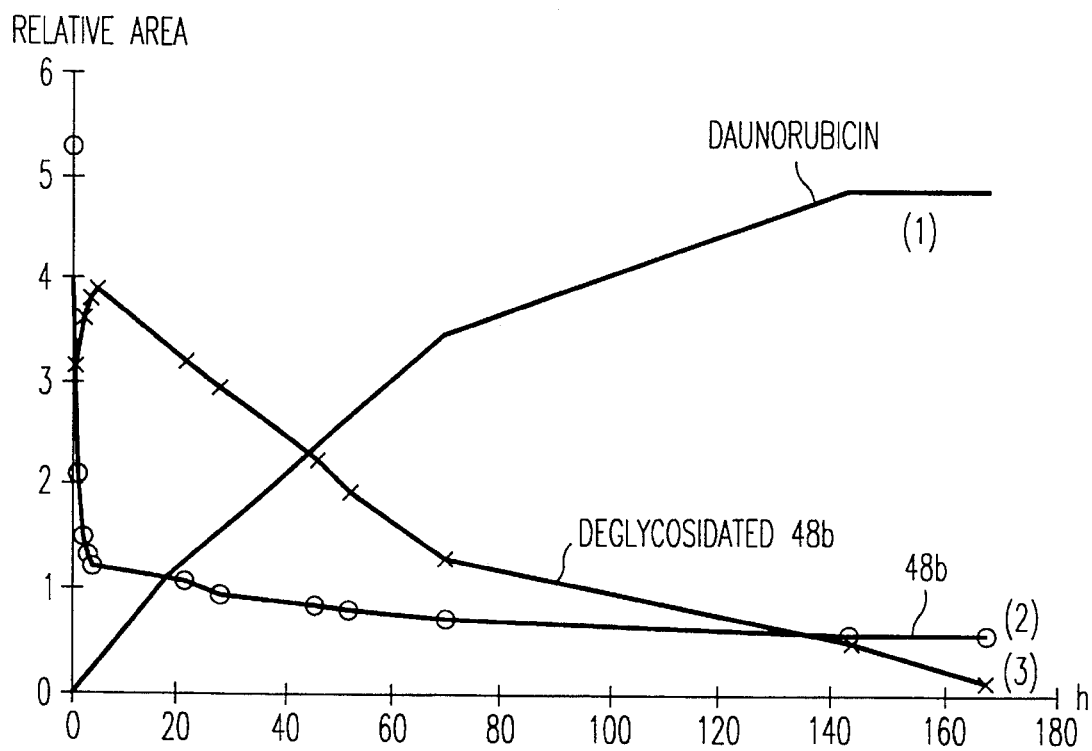
FIG. 1 shows the half-life of derivative 48b when the derivative is incubated with α-galactosidase.
Figure 2:
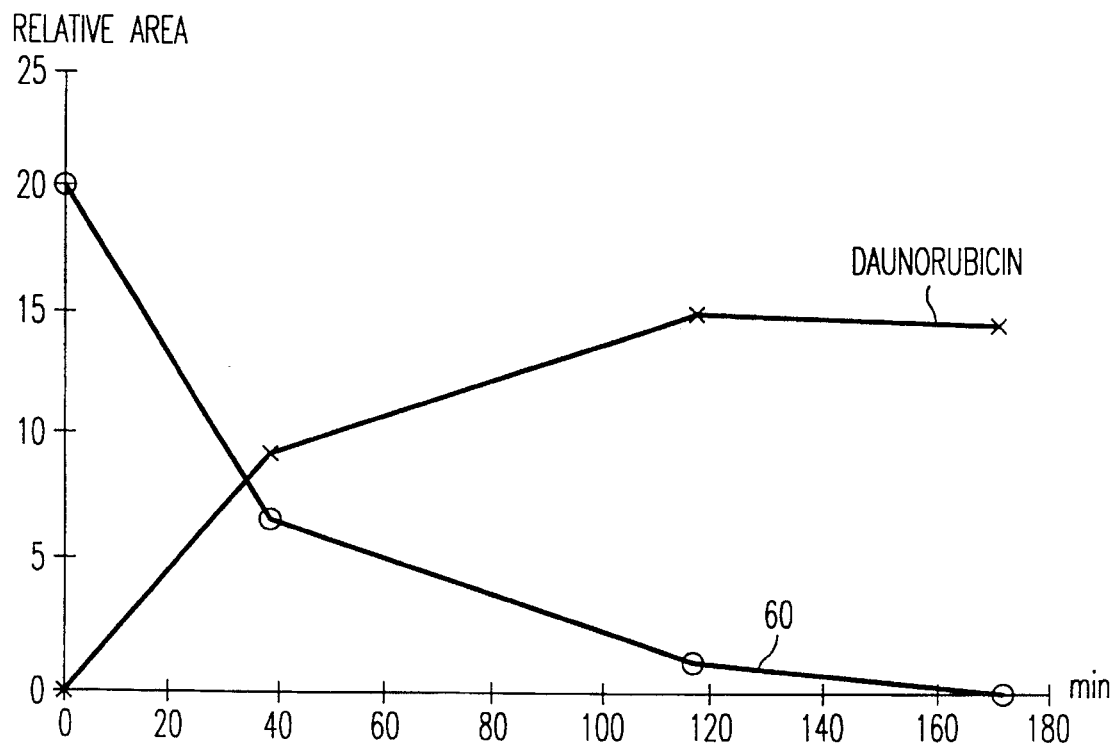
FIG. 2 shows the half-life when derivative 60 is incubated with α-galactosidase.

According to one advantageous embodiment of the invention, when Y is one or more electron-attracting groups, these are preferably in the ortho and/or para position to the glycosyl oxygen, and when Y is one or more electron-donating groups, these are preferably in the meta position.

According to the invention:
   when the benzyl CH$_2$ is in the ortho position relative to said glycosyl oxygen, Y is in the para position and is a hydrogen atom or an electron-attracting group, and/or in the meta position and is a hydrogen atom or an electron-donating group;

when the benzyl CH$_2$ is in the para position, Y is in the ortho position and is a hydrogen atom or an electron-attracting group, and/or in the meta position and is a hydrogen atom or an electron-donating group.

This gives para- or ortho-hydroxybenzyl carbamate derivatives of anthracyclines in which the phenol group is masked and which, surprisingly, can be cleaved into a pharmacologically active cytotoxic anthracycline and an ose, both by a glycosidase and by a glycosidase/tumor-specific ligand conjugate.

The compounds of formula I according to the invention include their various isomers.

The anthracycline prodrugs according to the invention, with 3 compartments, i.e. comprising an anthracycline, a self-sacrificing arm (para- or ortho-hydroxybenzyl carbamates) and an enzymatic substrate (ose), have the following advantages:

they prevent the risks of enzyme/substrate non-recognition, they avoid the problems of steric or electronic interference during the enzymatic cleavage reaction, and the connection between the amine group of the sugar and the O-heterosidic bond permits enzymatic attack and at the same time provides the molecule with sufficient bulk to significantly reduce the cytotoxicity of the prodrug.

Advantageously, as stated above, the intermediate arm is preferably a para- or ortho-hydroxybenzyl carbamate end the release of the active anthracycline from the prodrug with 3 compartments is determined by two processes:

(1) the rate of enzymatic hydrolysis, and (2) the rate of scission of the self-sacrificing arm, which are in fact linked, insofar as said self-sacrificing arm plays an important function both on the rate of enzymatic hydrolysis and on the rate of its scission, according to scheme A below:

SCHEME A

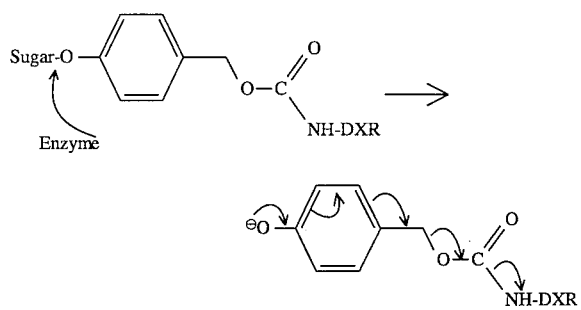

According to another advantageous embodiment of the invention, the preferred compounds of formula I contain the following radicals in particular:

R$_1$, R$_2$ and R$_3$ are hydrogen atoms,

R$_4$ is a methoxy group,

R$_5$ and R$_6$ are hydroxyl groups,

R is a —CO—CH$_3$ group or a —CO—CH$_2$OH group,

R$_7$ is a hydrogen atom or a hydroxyl group,

R$_8$, is a —CH$_2$—OAc, —CH$_2$OH, —COOMe or —COOH group,

R$_{10}$ and R$_{11}$, which can be identical or different, are a hydrogen atom or an Ac group, R$_{12}$ is a hydroxyl group or an OAc group, said radicals R$_8$, R$_{10}$, R$_{11}$ and R$_{12}$ preferably being in the following positions:

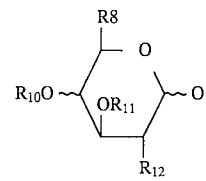

and

Y is a hydrogen atom, an NO$_2$ group or a chlorine atom in the para or ortho position to the glycosyl oxygen, and/or an OCH$_3$ group in the meta position to the glycosyl oxygen.

The present invention further relates to a method of preparing a compound of formula I which in particular can be degraded by a glycosidase, characterized in that it comprises:

(1) the coupling, if appropriate in the presence of a suitable promoter, of a derivative of formula A:

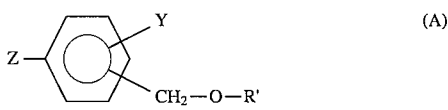

in which

Z is a hydroxyl group, an O-trialkylsilyl group or a group

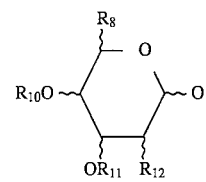

in which

R$_8$, R$_{10}$, R$_{11}$ and R$_{12}$ are as defined above;

R' is a hydrogen atom or one of the following groups:

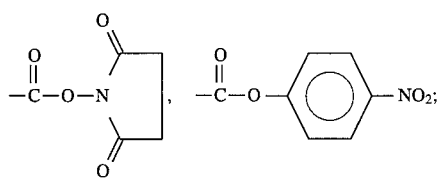

the benzyl —OH$_2$ is preferably in the pare or ortho position to the phenol group, which may be modified (glycosylated or silylated); and Y is a hydrogen atom, or at least one electron-attracting group selected especially from the group comprising the NO$_2$ group, a halogen atom and a group SO$_2$X (where X=—CH$_3$, C$_6$H$_4$—CH$_3$, NH$_2$, N—(C$_1$-C$_4$ alkyl)$_2$ or NH—C$_1$-C$_4$ alkyl), —CN, acyl or COO-alkyl, and/or at least one electron-donating group selected from the group comprising groups of the type O-alkyl, NH—CO-alkyl, N(alkyl)CO-alkyl, S-alkyl or alkyl, with an anthracycline of formula B:

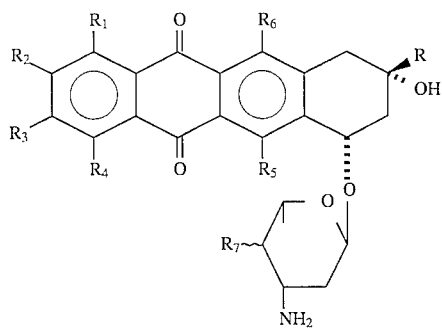

in which $R_1$, $R_2$, $R_3$, $R_4$, $R_5$, $R_6$, $R_7$ and R are as defined above;

(2) the removal of the protecting groups present in the compounds obtained, especially by hydrolysis, transesterification or saponification; and (3) if appropriate, suitable condensation with an ose of the following formula:

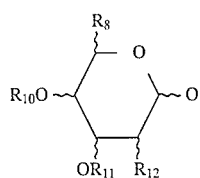

in the case where Z is a hydroxyl group or an O-trialkylsilyl group, to give an anthracycline prodrug of formula I, in which all the radicals $R_1$ to $R_{12}$ and R are as defined above.

When Z is an O-trialkylsilyl group, it is advantageously desilylated with tetrabutylammonium fluoride, for example, prior to condensation with an ose.

According to one advantageous embodiment of said method, the compound of formula A is a glycosylated hydroxybenzyl derivative of formula $A_1$:

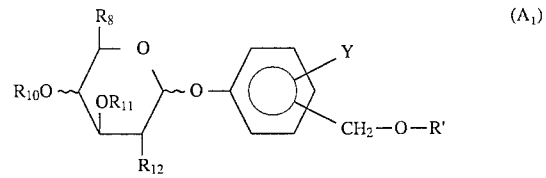

in which $R_8$, $R_{10}$, $R_{11}$, $R_{12}$, R' and Y are as defined above, which gives, after coupling with an anthracycline of formula B, an anthracycline prodrug of formula I as defined above, according to schemes I, II, III, IV, VI, X, XI, XIV, XV and XVI below:

SCHEME I

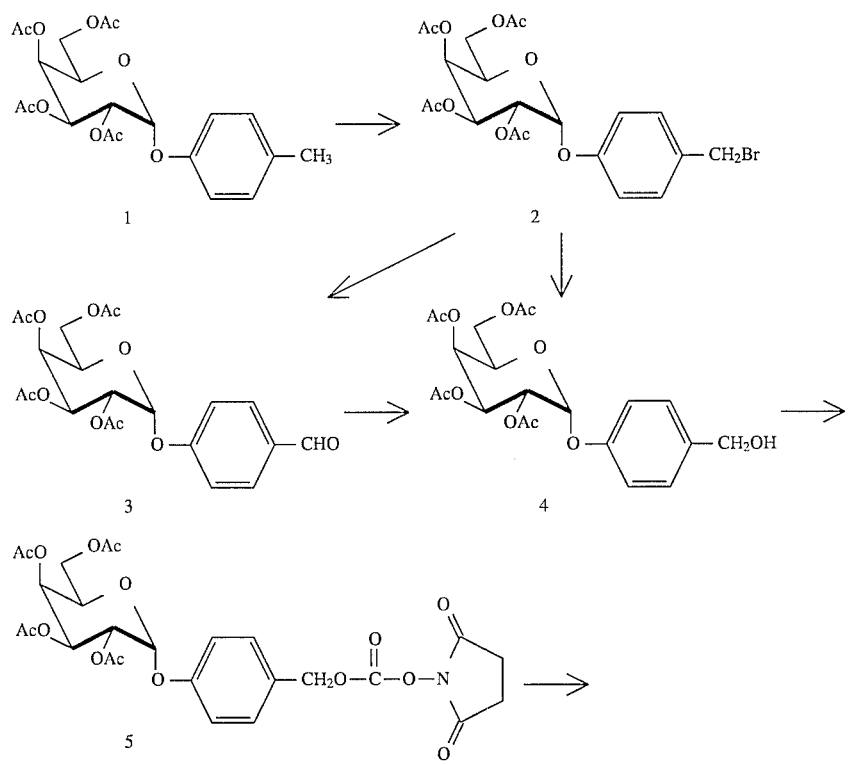

-continued
SCHEME I
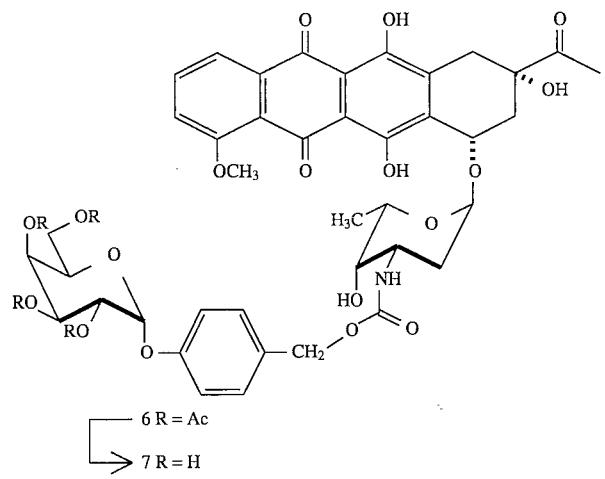
- 6 R = Ac
→ 7 R = H
SCHEME II
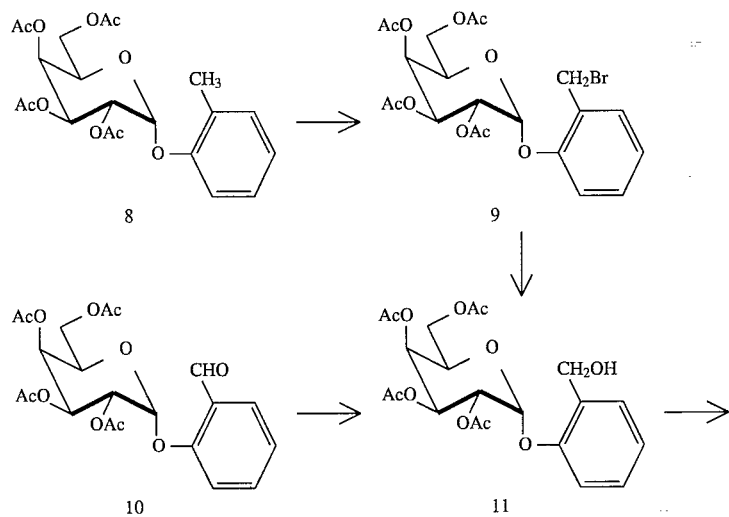

-continued
SCHEME II
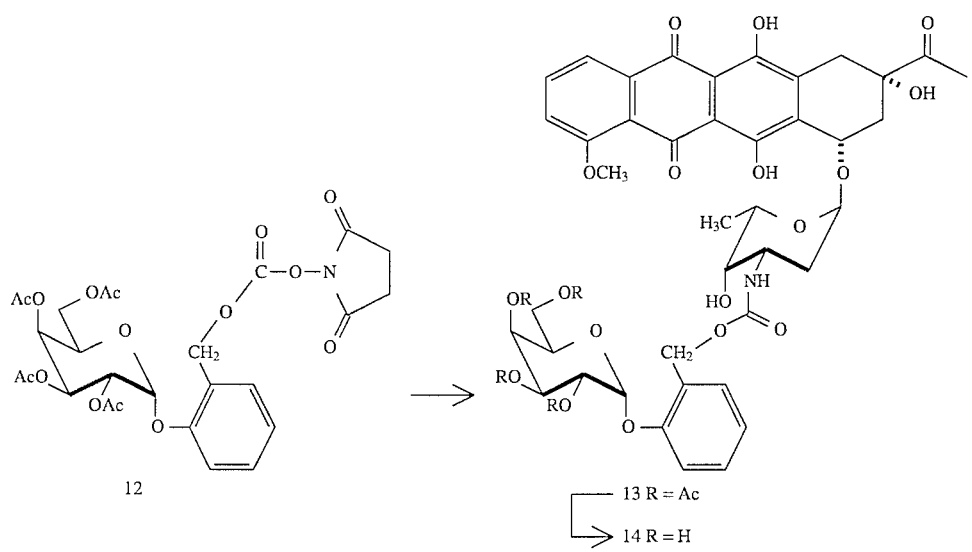
SCHEME III
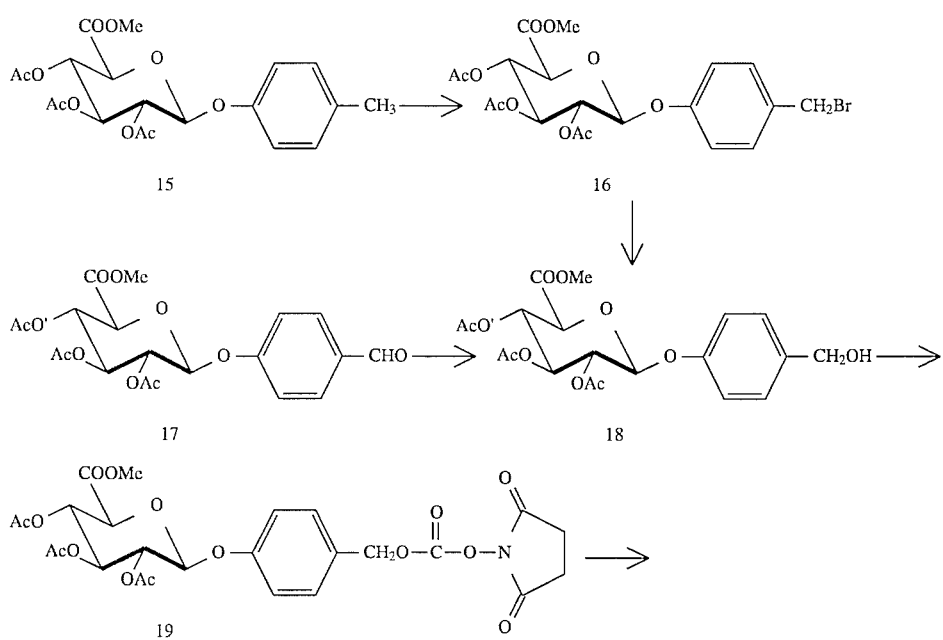

-continued
SCHEME III
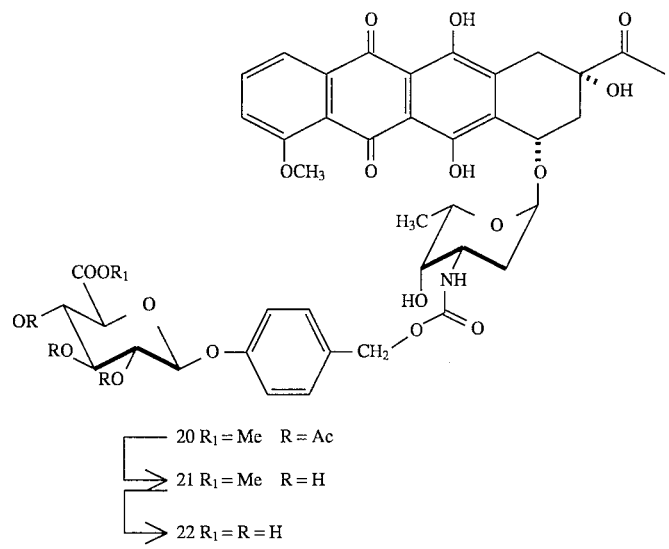
- 20 $R_1$ = Me  R = Ac
- 21 $R_1$ = Me  R = H
- 22 $R_1$ = R = H
SCHEME IV
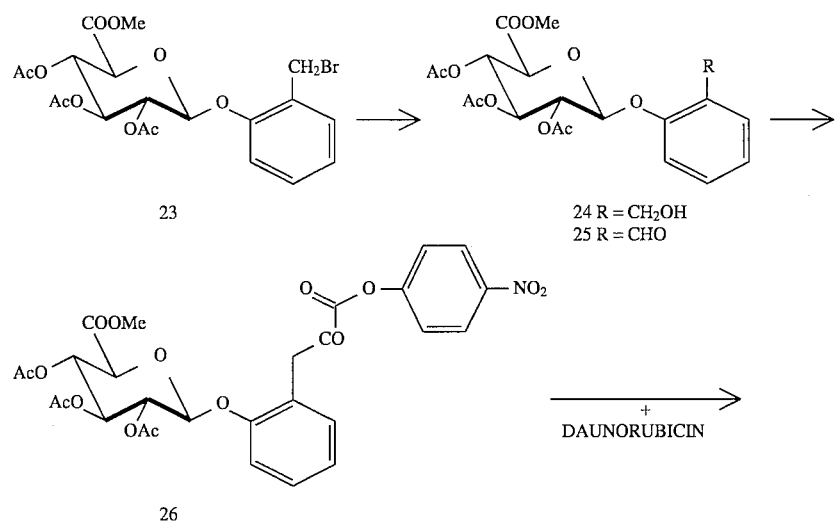
23
24 R = $CH_2OH$
25 R = CHO
26
+ DAUNORUBICIN →

-continued
SCHEME IV
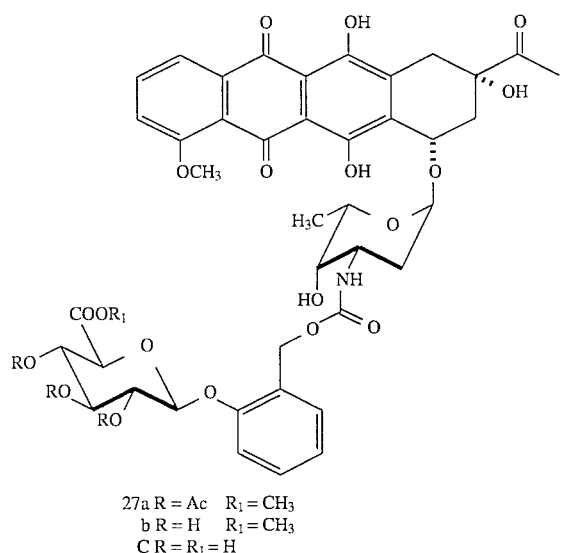
27a R = Ac  R₁ = CH₃
b R = H  R₁ = CH₃
C R = R₁ = H
SCHEME VI
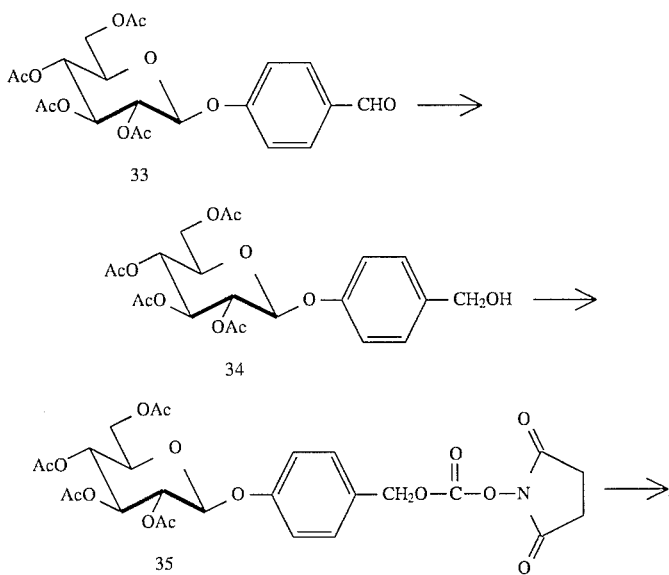

-continued
SCHEME VI
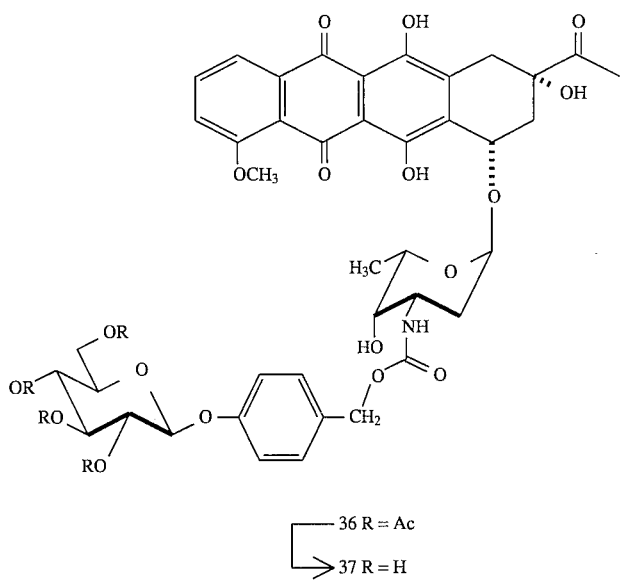
- 36 R = Ac
- 37 R = H
SCHEME X
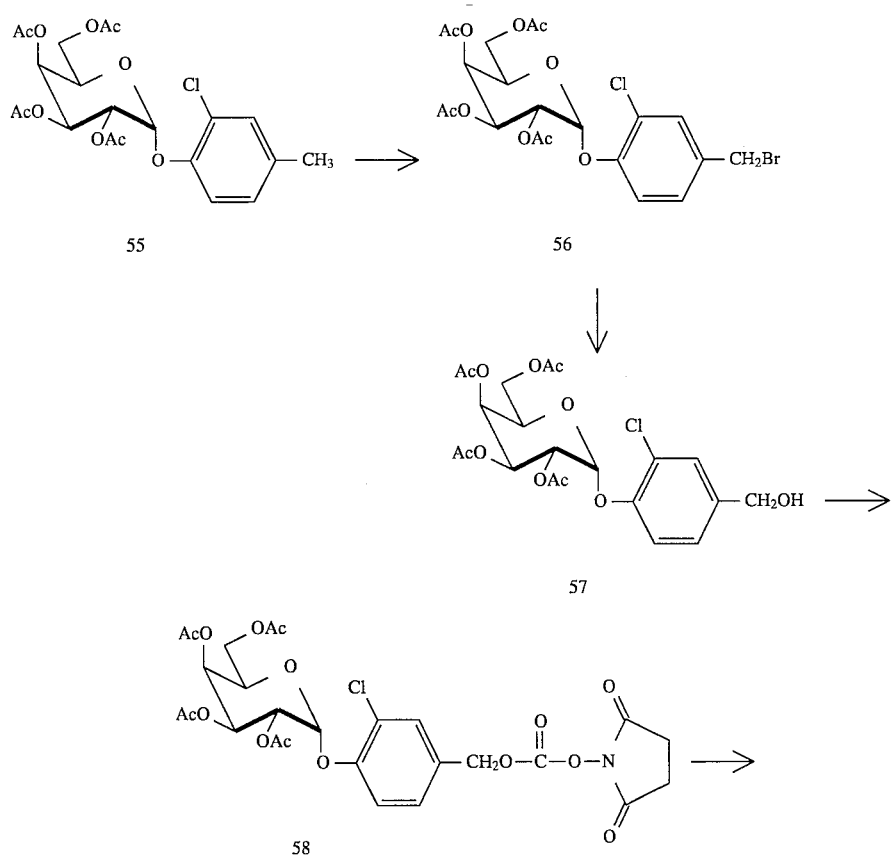

-continued
SCHEME X
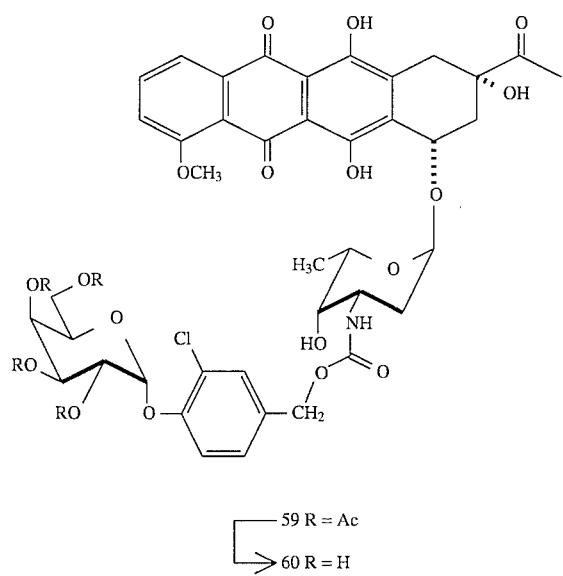
59 R = Ac
60 R = H
SCHEME XI
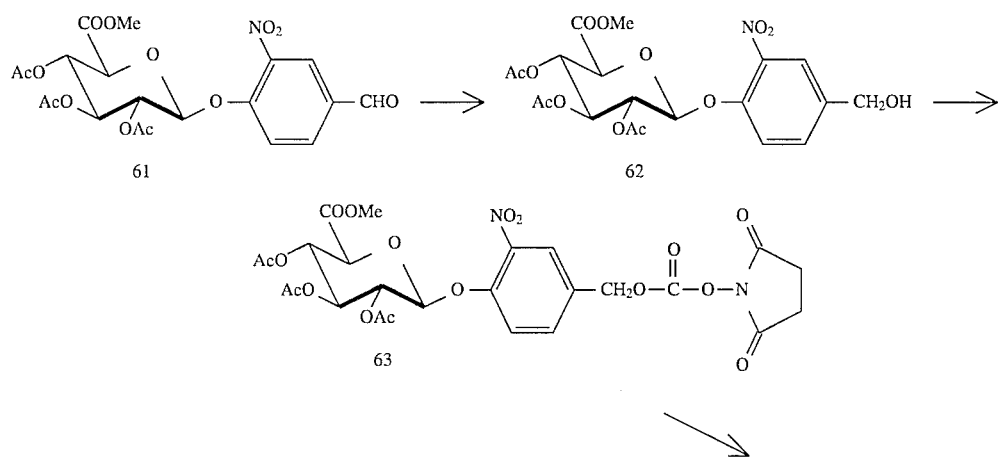

-continued
SCHEME XI
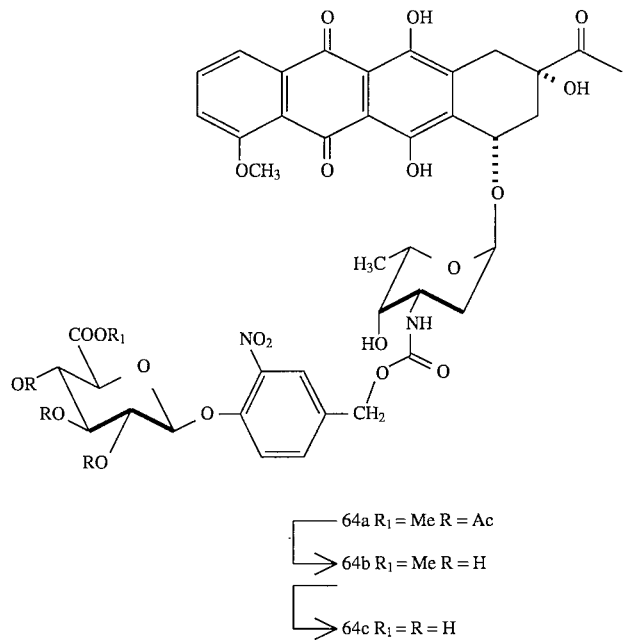
— 64a R₁ = Me R = Ac
→ 64b R₁ = Me R = H
→ 64c R₁ = R = H
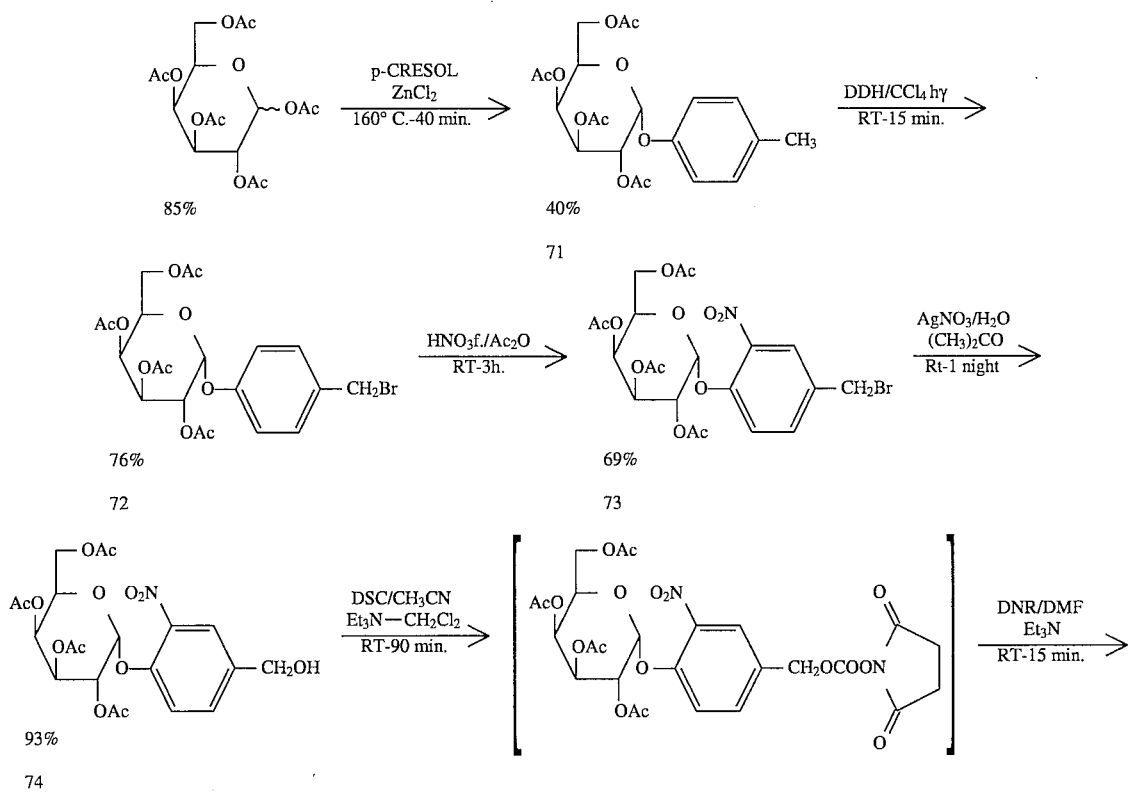

-continued
SCHEME XIV
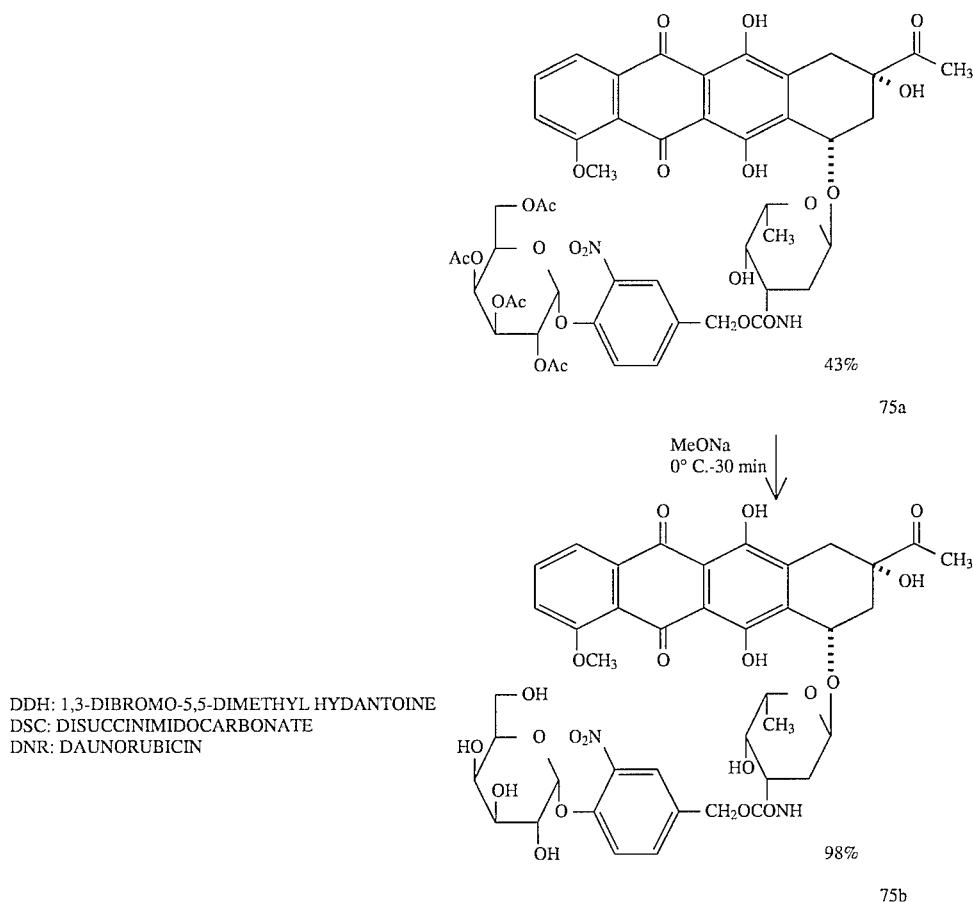
DDH: 1,3-DIBROMO-5,5-DIMETHYL HYDANTOINE
DSC: DISUCCINIMIDOCARBONATE
DNR: DAUNORUBICIN
SCHEME XV
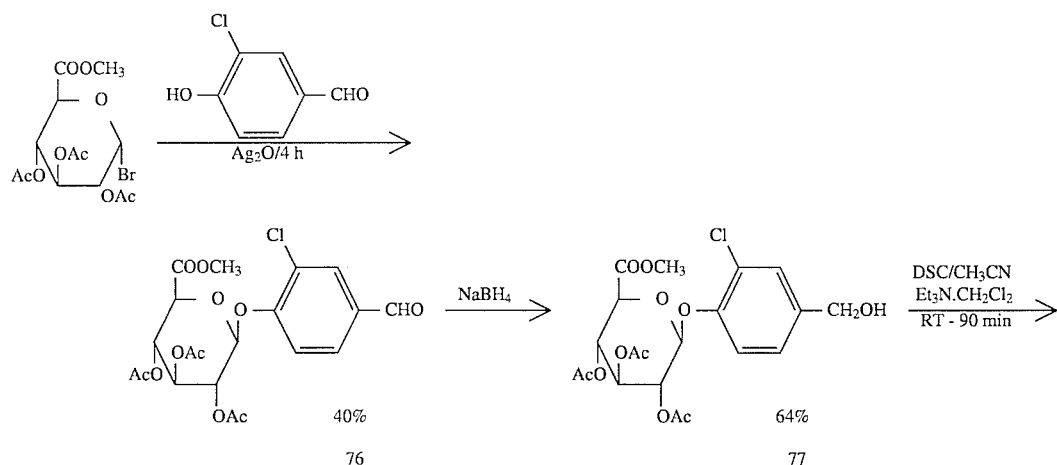

-continued
SCHEME XV
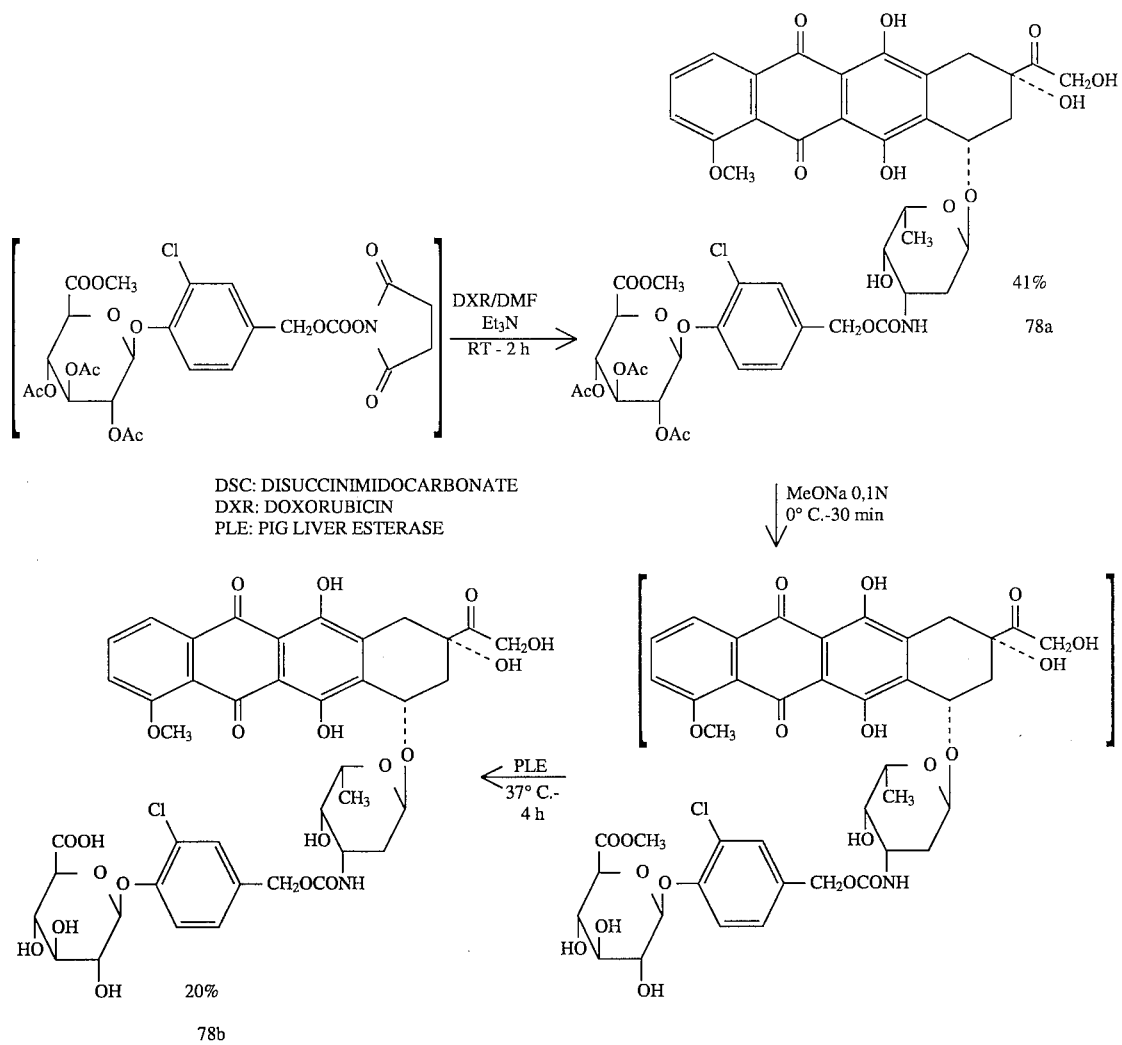
DSC: DISUCCINIMIDOCARBONATE
DXR: DOXORUBICIN
PLE: PIG LIVER ESTERASE
SCHEME XVI
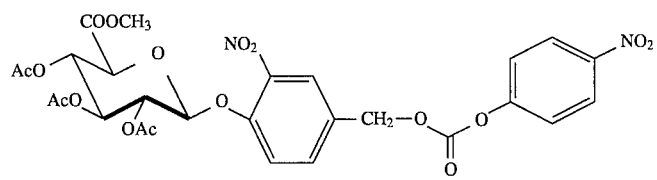
69

-continued
SCHEME XVI

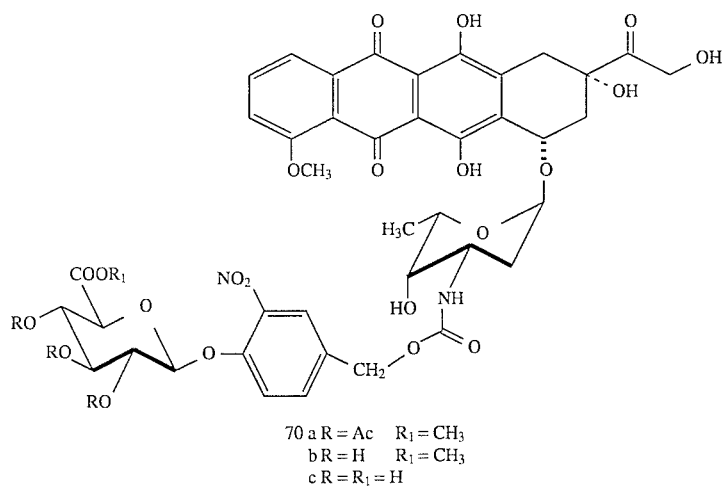

70 a R = Ac   R₁ = CH₃
   b R = H    R₁ = CH₃
   c R = R₁ = H

According to one advantageous provision of this embodiment, prior to step (1), the glycosylated p-hydroxybenzyl derivative is obtained by:

(a) fusion of a cresol with an ose or a peracetylated methyl glucuronate,
(b) benzyl bromination of the product obtained,
(c) solvolysis of the brominated derivative, and
(d) activation of the hydroxyl group with a hydroxysuccinimidyl or paranitrophenoxycarbonyl derivative.

According to another embodiment of said method, the compound of formula A is a silylated derivative of formula $A_2$:

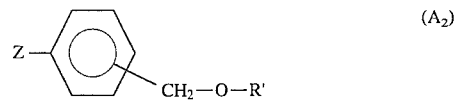

in which R' is as defined above and Z is an O-dimethylhexylsilyl group or an O-tert-butyldimethylsilyl group, which gives, after coupling with an anthracycline of formula B and condensation with a suitable ose, an anthracycline prodrug of formula I as defined above, according to schemes V and VII, which describe the method of obtaining the silylated derivatives before they are condensed with a suitable ose.

SCHEME V

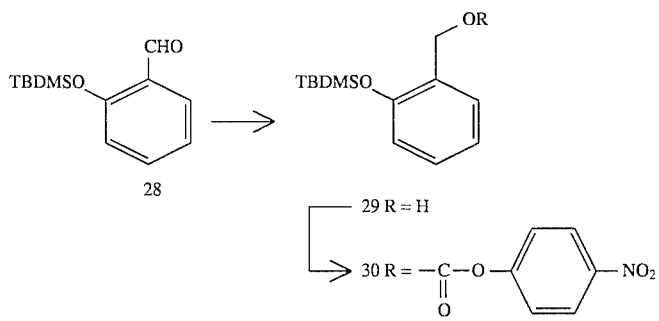

29 R = H
30 R = —C—O—⟨ ⟩—NO₂
         ‖
         O

-continued
SCHEME V
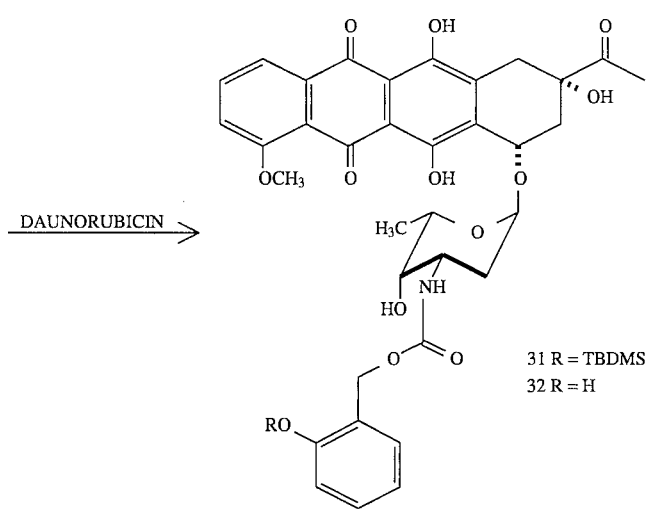
SCHEME VII
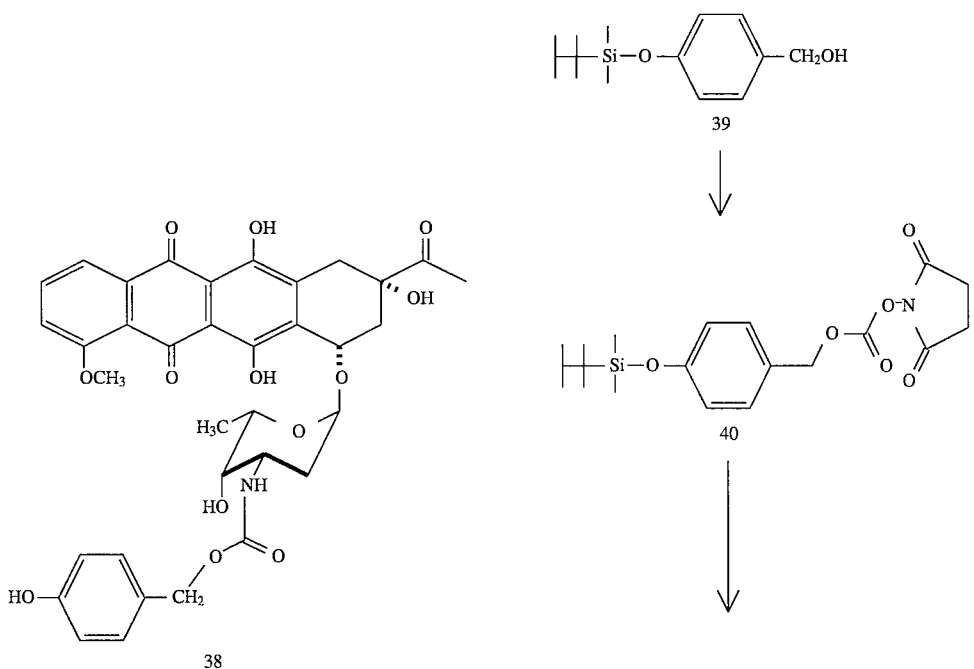

-continued
SCHEME VII

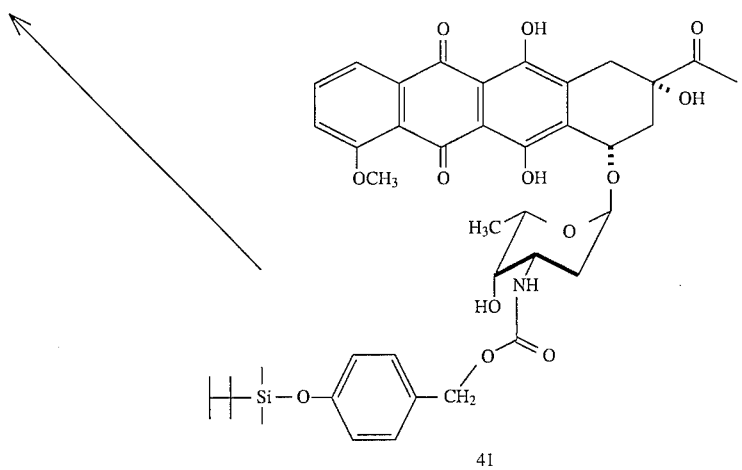

41

According to yet another mode of carrying out the method according to the invention, the compound of formula A is a glycosylated orthohydroxybenzyl derivative of formula $A_3$:

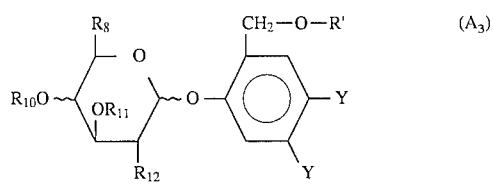

in which $R_8$, $R_{10}$, $R_{11}$, $R_{12}$ and R' are as defined above and Y is in the para position and is an $NO_2$ group or an halogen atom and in the meta position and is a hydrogen atom or an methoxy group, which gives, after coupling with an anthracycline of formula B, an anthracycline prodrug of formula I as defined above in which the benzyl $CH_2$ is in the ortho position relative to the glycosyl oxygen, according to schemes VIII, IX, XII and XIII below:

SCHEME VIII

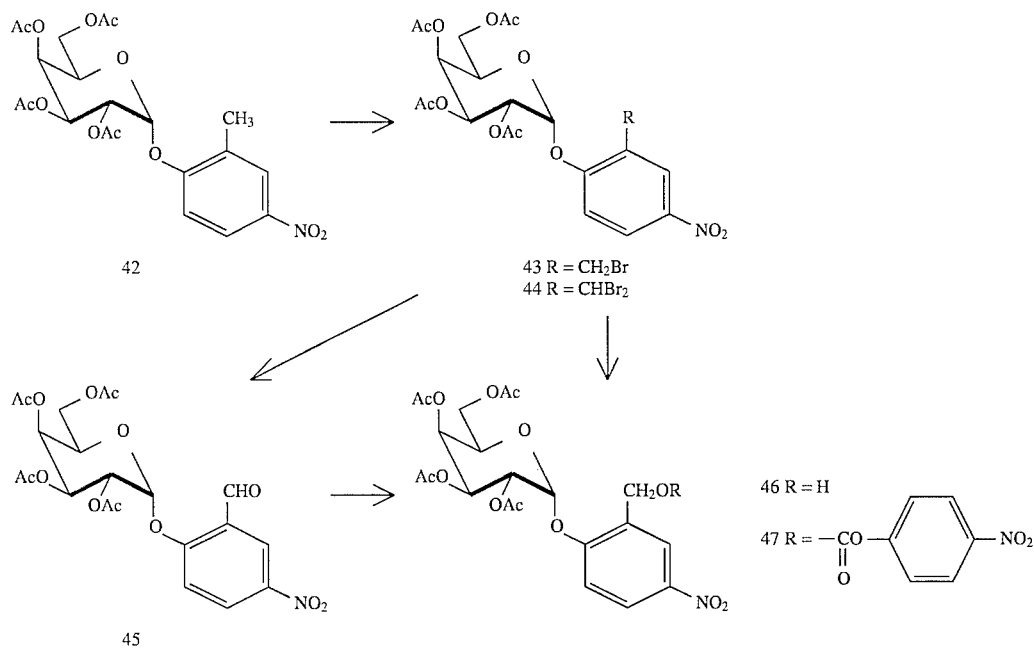

33 34
-continued
SCHEME VIII
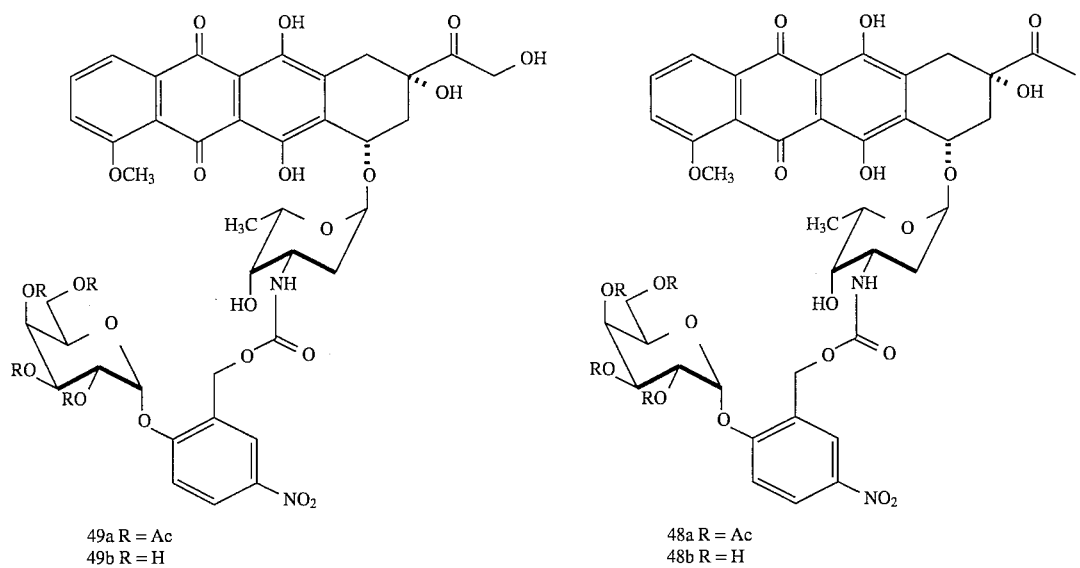
49a R = Ac
49b R = H
48a R = Ac
48b R = H
SCHEME IX
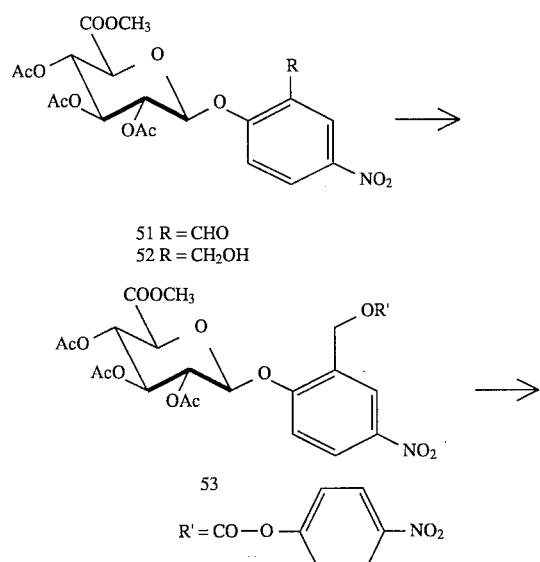
51 R = CHO
52 R = CH₂OH
53
R' = CO—O—⟨4-NO₂-phenyl⟩
-continued
SCHEME IX
54a R = Ac R₁ = CH₃
b R = H R₁ = CH₃
c R = R₁ = H
SCHEME XII
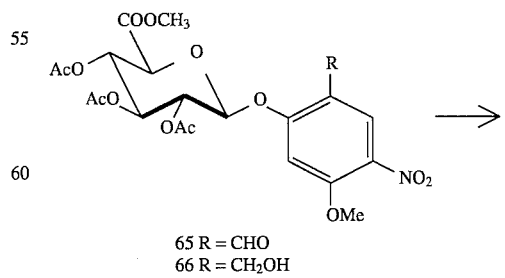
65 R = CHO
66 R = CH₂OH

SCHEME XII -continued
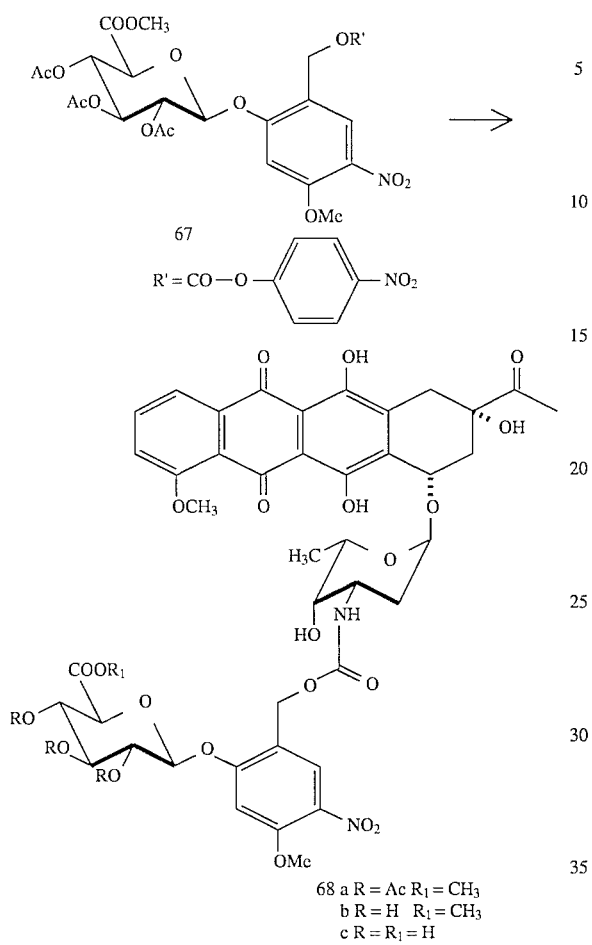
SCHEME XIII
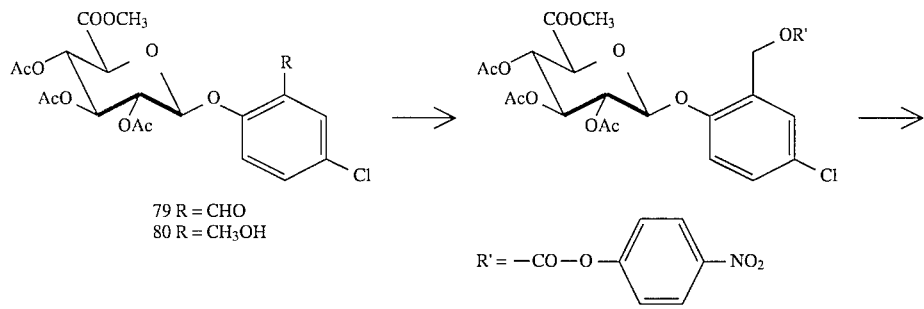

-continued
SCHEME XIII

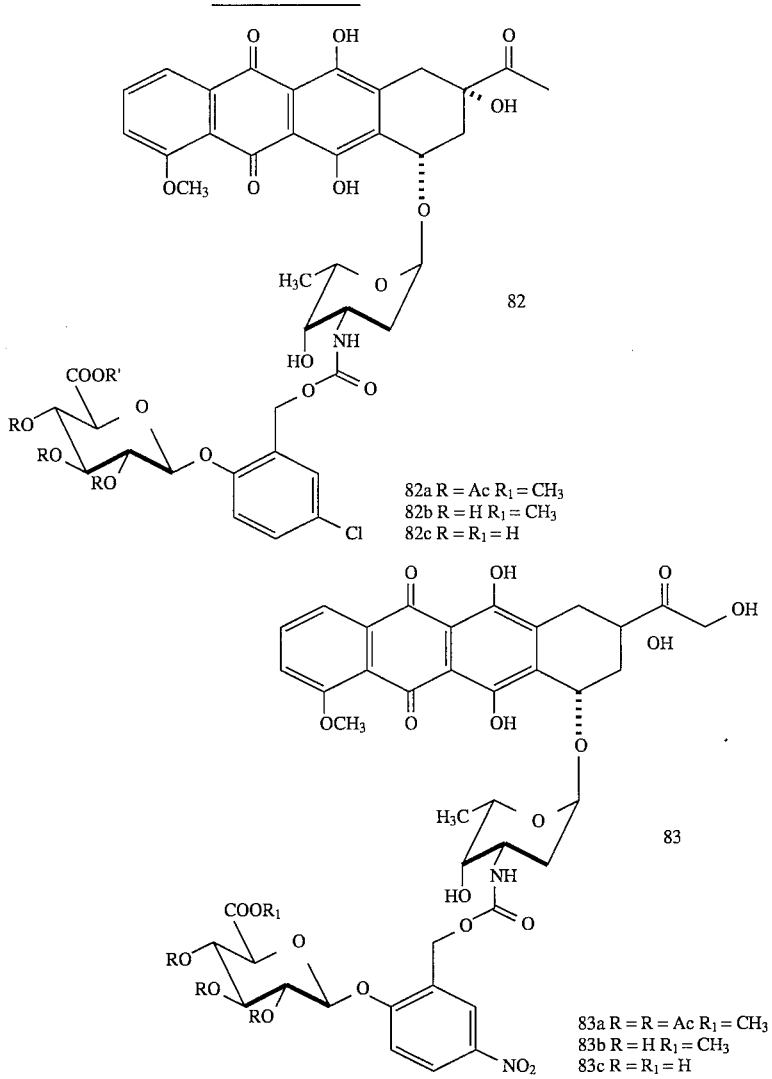

The present invention further relates to products comprising an anthracycline prodrug according to the invention and an enzyme/tumor-specific antibody conjugate of formula II, Ab-Sp-E, in which Ab is an antibody or one of its fragments, which is specific towards an antigen associated with a tumor, or is a biomolecule which tends to accumulate in a tumor, such as EGF (epidermal growth factor), α-TGF (α transforming growth factor), PDGF (platelet derived growth factor), IGF I+II (insulin growth factor I+II) or FGF a+b (fibroblast growth factor a+b), E is a glycosidase which is not immunogenic or has a very low immunogenicity, preferably a mammalian glycosidase such as α- or β-glucosidase, α-galactosidase, α- or β-mannosidase, α-fucosidase, N-acetyl-α-galactosaminidase, N-acetyl-β- band N-acetyl-α-glucosaminidase or β-glucuronidase, and Sp (arm) is a group containing a sulfide or a disulfide, of formula III or IV:

X'(S)$_n$Y'  (III)

X'(S)$_n$  (IV)

or a polypeptide arm, in which

X' or Y' is —CO—R$_{13}$—(N-succinimido)— or —C(=R$_{14}$)—CH$_2$—CH$_2$—, where R$_{13}$ is a —CH$_2$—CH$_2$, 1,4-cyclohexylidene, 1,3- or 1,4-phenylene or methoxycarbonyl- or chloro-1,4-phenylene group and R$_{14}$ is an oxygen atom or an NH group, and also Y' is —C(=R$_{14}$)—CH$_2$—CH$_2$ when R$_{14}$ is as defined above, and n is 1 or 2, for use in cytostatic therapy, either simultaneously, separately or spread out over a period of time.

According to the invention, both the anthracycline prodrug and the enzyme/antibody conjugate can be associated with at least one pharmaceutically acceptable vehicle.

Such an enzyme/antibody conjugate is described more particularly in German patent application 39 35016.9, in the name of BEHRING.

The coupling between the enzyme and the antibody, antibody fragment or biomolecule is effected by means of a method described in the literature (A. H. BLAIR and T. I. GHOSE, Immunology Methods, 1983, 59, 129–143; T. I. GHOSE et al., Methods in Enzymol., 1983, 19, 280–333).

This involves the initial functionalization of the enzyme via its amino group using a succinimidyl N-maleimidoalkylidene-, -cycloalkylidene- or -arylene-1-carboxylate, in which the double bond of the maleimido group reacts with the HS group of the functionalized antibody, antibody fragment or biomolecules to form a thioether group.

The antibody/enzyme conjugates can be prepared using the monoclonal antibodies described in European patent application 141 079, preferably the antibodies 431/26, 250/183,704/152 and 494/32.

The specificity of these antibodies for antigens associated with tumors has already been demonstrated in animals and man by methods of immunoscintigraphy and immunochemistry.

For the preparation of the tumor-specific enzymatic conjugates, it is possible for the enzymes mentioned below, obtained from the identified source, to be purified by the procedure indicated in the literature:

α-galactosidase from human liver, DEAN, K. G. and SWEELEY, C. C. (1979), J. Biol. Chem., 254, 994–1000;

β-glucuronidase from human liver, HO, K. J. (1985), Biochim. Biophys. Acta, 827, 197–206;

α-L-fucosidase from human liver, DAWSON, G., TSAY, G. (1977), Arch. Biochem. Biophys., 184, 12–23;

α-mannosidase from human liver, GRABOWSKI, G. A., IKONNE, J. U., DESNICK, R. J. (1980), Enzyme, 25, 13–25;

β-mannosidase from human placenta, NOESKE, C., MERSMANN, G. (1983), Hoppe Seylers Z. Physiol. Chem., 364, 1645–1651;

α-glucosidase from human gastrointestinal mucosa, ASP, N. G., GUDMAND-HOEYER, E., CHRISTIANSEN, P. M., DAHLQUIST, A. (1974), Scand. J. Clin. Lab. Invest., 33, 239–245;

β-glucosidase from human liver, DANIELS, L. B., COYLE, P. J., CHIA, Y. B., GLEW, R. H. (1981), J. Biol. Chem., 256, 13004–13013;

β-glucocerebrosidase from human placenta, FURBISH, F. S., BLAIR, H. E., SHILOACH, J., PENTCHEU, P. G., BRADY, R. O. (1977), Proc. Natl. Acad. Sci. USA, 74, 3560–3563;

α-N-acetylglucosaminidase from human placenta, ROEHRBORN, W., VON FIGURA, K. (1978), Hoppe Seylers Z. Physiol. Chem., 359, 1353–1362;

β-N-acetylglucosaminidase from human amniotic membrane, ORLACCHIO, A., EMILIANI, C., DI RENZO, G. C., COSMI, E. V. (1986), Clin. Chim. Acta, 159, 279–289;

α-N-acetylgalactosaminidase according to SALVAYRE, R., NEGRE, A., MARET, A., DOUSTE-BLAZY, L. (1984), Pathol. Biol. (PARIS), 32, 269–284.

The glycolytic activity of the enzyme/tumor specific antibody conjugates was determined, by comparison with p-nitrophenyl glycosides, at optimum pH.

To test the efficacy of sequential and combined use of the enzyme/antibody conjugate and the prodrug, the conjugate is administered to transplanted mice and then, after the plasma enzyme level has returned virtually to zero, the modified anthracycline (prodrug) is administered; observations are made to see whether there is a cessation of tumor growth and whether a regression is taking place.

The prodrugs 7, 14, 48b, 49b, 60 and 75b and the acetates 6, 13, 48a, 49a, 59 and 75a, which hydrolyze in vivo under the action of enzymes to give one of the above-mentioned prodrugs, are α-galactosides; the prodrugs 22,27c,54c,64c, 70c,78b and83c areβ-glucuronides; the prodrug 37 and its acetate 36 are β-glucosides. These prodrugs are advantageously cleaved to give daunorubicin or doxorubicin, as the case may be, in the presence of the appropriate conjugate as defined above.

Unexpectedly, the compositions according to the invention, combining a prodrug with three compartments and a conjugate in which the enzyme is a non-circulating enzyme of human origin, make it possible to solve both the problem of immunological tolerance and the problem of specificity of action at the site of the tumor and, as stated above, avoid steric or electronic interference during the enzymatic cleavage.

Also unexpectedly, the prodrugs with three compartments according to the invention can be cleaved by activated macrophages, granulocytes, thromobocytes or human tumor cells.

In fact, these activated cells release β-glucuronidase, which is capable of cleaving the glucuronyl/self-sacrificing arm/drug compounds effectively (by hydrolysis).

Such prodrugs can thus be used directly as drugs for the treatment of diseases which involve activated macrophages, granulocytes, thrombocytes or human tumoral cells.

Apart from the foregoing provisions, the invention also includes other provisions which will become apparent from the following description relating to Examples of how to carry out the method forming the subject of the present invention.

It must be clearly understood, however, that these Examples are given solely in order to illustrate the subject of the invention, without in any way implying a limitation.

EXAMPLE 1

Synthesis of N-(4-hydroxybenzyloxycarbonyl)daunorubicin α-D-galactopyranoside (7)

According to scheme I, the coupling of penta-O-acetyl-D-galactopyranose with paracresol is carried out by fusion in the presence of $ZnCl_2$ or of $ZnCl_2$ in an $AcOH/AC_2O$ mixture.

The benzyl bromination of the compound (1) obtained is carried out either in the presence of N-bromosuccinimide (NBS) and photochemical activation to give the compound 2 only, or in the presence of NBS and benzoyl peroxide to give mainly the compound 2 and small amounts of the aldehyde derivative 3.

The displacement of the bromine from the derivative 2 is carried out in acetone or in ether/acetone with (or without) $(Bu_3Sn)_2O$ to give the derivative 4, whereas the reduction of the aldehyde derivative 3 with sodium borohydride gives further amounts of the compound 4.

The activation of the OH group in the derivative 4 is carried out using N-succinimidyl chloroformate or disuccinimidyl carbonate (DSC).

In a subsequent step, the coupling of the derivative 5 with daunorubicin is carried out in DMF in the presence of $Et_3N$ and the N-hydroxybenzylcarbonyl derivative 6 is deprotected by transesterification to give the desired derivative 7.

1) 4-Methylphenyl 2,3,4,6-tetra-O-acetyl-α-D-galactopyranoside (1)

Preparations:

Method I: 8.9 g of p-cresol, 8.9 g of penta-O-acetyl-D-galactopyranose and 0.56 g of $ZnCl_2$ are mixed, heated to 160° C. and kept at this temperature for 30 minutes, according to HELFERICH's method. After cooling to 60° C., the reaction medium is taken up with 400 ml of $CH_2 Cl_2$ and washed with twice 400 ml of water and then with a solution of sodium hydroxide (≈1N) until the aqueous phase is practically colourless. The organic phase is finally washed with twice 400 ml of water, dried over anhydrous sodium sulfate and then evaporated to dryness in a water bath (temperature: 35°– 40° C.) to give a residue of 7.08 g (yield=70%). Chromatography on a column of 60H silica (solvent: hexane/ethyl acetate: 90/10 v/v) gives 2.9 g of the compound 1 (yield=29%) and 1.17 g of its β anomer (yield=12%).

Method II: 11 g of penta-O-acetyl-D-galactopyranose, 11 g of p-cresol and 2.4 g of $ZnCl_2$ are dissolved in 8 ml of a mixture of acetic acid and acetic anhydride (95/5 v/v) and heated to 120° C. Reflux is maintained for 2 hours.

After evaporation of the solvent under reduced pressure, the residue is taken up with 120 ml of $CH_2Cl_2$. The organic solution is washed with water, then with a solution of sodium hydroxide (≈1N) and finally with water before being dried over anhydrous sodium sulfate and evaporated to dryness under reduced pressure. This gives a crude residue of 7 g (yield=64%). After purification on a column of 60H silica (solvent: hexane/ethyl acetate: 70/30 v/v), the product 1 is obtained with a yield of 13% and its β anomer with a yield of 6.5%.

Compound 1: $C_{21}H_{26}O_{10}$. M=438. M.p.=163°–165° C. $[α]_D^{20}$=+164° (c 1, $CHCl_3$). $^1$H NMR (270 MHz, $CDCl_3$): δ ppm: 1.90 (s, 3H), 2.02 (s, 3H), 2.08 (s, 3H), 2.19 (s, 3H), 2.28 (s, 3H), 4.00 (dd, 1H, J=12, J'=7 Hz), 4.09 (dd, 1H, J=12, J'=6 Hz), 4.40 (ddd, 1H, J=7, J'=5 J"=1 Hz), 5.27 (dd, 1H, J=10, J', =4 Hz), 5.54 (dd, 1H, J=4, J'=1 Hz), 5.57 (dd, 1H, J=10, J'=4 Hz), 5 73 (d, 1H, J=4 Hz), 6.90 (d, 2H, J=8 Hz), 7.10 (d, 2H, J=8 Hz). MS (DIC/$NH_3$): m/z: 456 $(M+NH_4)^+$, 331.

2) 4-Bromomethylphenyl 2,3,4,6-tetra-O-acetyl-α-D-galactopyranoside (2)

Preparation:

1) with photochemical activation:

1.02 g of N-bromosuccinimide are added to a solution of 1 (2.5 g) in 100 ml of carbon tetrachloride and the mixture is refluxed at 80° C. under irradiation with light (1000 W) for 15 min. After cooling, the reaction medium is filtered to remove the succinimide which has precipitated, and the filtrate is then evaporated under reduced pressure to give 3.23 g of dry residue. 2.45 g of 2 are isolated after purification on a column of 60H silica (solvent: hexane/ethyl acetate: 70/30 v/v) (yield=83%).

2) with benzoyl peroxide activation:

0.8 g of N-bromosuccinimide and 0.08 g of benzoyl peroxide are added to a solution of 1 g of the product 1 in 40 ml of carbon tetrachloride. The reaction medium is refluxed for 3 h. After cooling, the reaction medium is filtered to remove the succinimide which has precipitated, and the filtrate is then evaporated to dryness to give 1.64 g of product. Flash chromatography (solvent: hexane/ethyl acetate: 80/20 v/v) gives 1.74 g of a mixture of the monobrominated derivative 2 and the corresponding dibrominated derivative and makes it possible to isolate 0.08 g of the pure compound 3.

Compound 2: $C_{21}H_{25}O_{10}Br$. M=517. M.p.=187° C. $[α]_D^{20}$=+26° (c 1, $CHCl_3$). $^1$H NMR (270 MHz, $CDCl_3$): δ ppm: 1.94 (s, 3H), 2.03 (s, 3H), 2.07 (s, 3H), 2.17 (s, 3H), 4.06 (dd, 1H, J=12, J'=7 Hz), 4.12 (dd, 1H, J=12, J'=6 Hz), 4.32 (ddd, 1H, J=7, J'=6, J"=1 Hz), 4.49 (s, 2H), 5.29 (dd, 1H, J=10, J'=4 Hz), 5.55 (dd, 1H, J=4, J'=1 Hz), 5.60 (dd, 1H, J=10, J'=4 Hz), 5.78 (d, 1H, J=4 Hz), 7.02 (d, 2H, J=8 Hz), 7.33 (d, 2H, J=8 Hz). MS (DIC/$NH_3$): m/z: 536 $(M+NH_4)^+$, 534 $(M+NH_4)^+$, 456, 331.

4-Formylphenyl 2,3,4,6-tetra-O-acetyl-α-D-galactopyranoside (3)

$C_{21}H_{24}O_{11}$. M=452. $^1$H NMR (270 MHz, $CDCl_3$): δ ppm: 1.91 (s, 3H), 2.03 (s, 3H), 2.06 (s, 3H), 2.20 (s, 3H), 4.09 (m, 2H), 4.28 (ddd, 1H, J=7, J'=6, J"=1 Hz), 5.30 (dd, 1H, J=10, J'=4 Hz), 5.52 (m, 2H), 5.88 (d, 1H, J=4 Hz), 7.17 (d, 2H, J=8 Hz), 7.83 (d, 2H, J=8 Hz), 9.89 (s, 1H). MS (DIC/$NH_3$): m/z: 470 $(M+NH_4)^+$, 331.

4-Hydroxymethylphenyl 2,3,4,6-tetra-O-acetyl-α-D-galactopyranoside (4)

Preparation:

A solution of 1.89 g of the compound 2 in 80 ml of acetone is mixed with an equal volume of a 0.1N aqueous solution of silver nitrate. The mixture is stirred at 25° C. for 2 h, the acetone is then evaporated off under reduced pressure, the remaining aqueous phase is extracted with $CH_2Cl_2$ and the extract is washed with water and then dried over anhydrous sodium sulfate, filtered and evaporated to dryness under reduced pressure. The dry residue obtained (1.52 g) is then purified by flash chromatography on a column of silica (solvent: hexane/ethyl acetate: 60/40 v/v). The product 4 (0.94 g) is obtained with a yield of 56%.

$C_{21}H_{26}O_{11}$. M=454. M.p.=153° C. ($CH_2Cl_2$). $[α]_D^{20}$=+144.5° (c 1, $CHCl_3$) $^1$H NMR (270 MHz, $CDCl_3$): δ ppm: 1.73 (1H, exch. $D_2O$), 1.96 (s, 3H), 2.03 (s, 3H), 2.08 (s, 3H), 2.17 (s, 3H), 4.07 (dd, 1H, J=12, J'=7 Hz), 4.09 (dd, 1H, J=12, J'=6 Hz), 4.35 (ddd, 1H, J=7, J'=6 J"=1 Hz), 4.64 (s, 2H), 5.28 (dd, 1H, J=10, J'=4 Hz), 5.51 (dd, 1H, J=4, J'=1 Hz), 5.54 (dd, 1H, J=10, J'=4 Hz), 5.60 (d, 1H, J=4 Hz), 7.04 (d, 2H, J=8 Hz), 7.30 (d, 2H, J=8 Hz). MS (DIC/$NH_3$): m/z: 472 $(M+NH_4)^+$, 331.

2,5-Dioxopyrrolidin-1-yl 4-(2,3,4,6-tetra-O-acetyl-α-D-galactopyranosyl)benzyl carbonate (5)

The compound 4 is converted to the succinimidocarbonate by coupling with succinimidyl chloroformate.

a) Preparation of succinimidyl chloroformate:

A solution of 2 g of N-hydroxysuccinimide in 11 ml of ethanol is mixed with a solution of 1 g of potassium hydroxide in 30 ml of ethanol. The product formed is filtered off, washed with ether and dried overnight at 40° C. under vacuum to give 2.40 g of the potassium salt of hydroxysuccinimide (yield=94%).

200 mg of the potassium salt of N-hydroxysuccinimide are added to 3 ml of a 20% solution of $COCl_2$ in toluene at 5° C., with stirring. After stirring for 2 h, the potassium chloride formed is filtered off and the filtrate is evaporated under reduced pressure. The residue is dissolved in ether and a white solid, consisting of disuccinimidyl carbonate, deposits and is filtered off. The filtrate is evaporated to dryness under reduced pressure to give 150 mg of succinimidyl chloroformate (yield=54%).

b) Preparation of the succinimidocarbonate:

150 mg of the compound 4 are added to 117 mg of succinimidyl chloroformate and 0.05 ml of pyridine in 8 ml of ethyl acetate. The mixture is stirred for 48 h at room temperature and filtered and the filtrate is evaporated under reduced pressure to give 189 mg of the compound 5 (yield=96%): $C_{26}H_{29}O_{15}N$. M=595. Lac. $[α]_D^{20}$=+142° (c 0.3, $CHCl_3$). $^1$H NMR (270 MHz, $CDCl_3$): δ ppm: 1.90 (s, 3H), 2.03 (s, 3H), 2.07 (s, 3H), 2.16 (s, 3H), 2.83 (s, 4H), 4.07 (dd, 1H, J=12, J'=7 Hz), 4.11 (dd, 1H, J=12, J'=6 Hz), 4.30 (ddd, 1H, J=7, J'=6, J"=1 Hz), 5.26 (s, 2H), 5.29 (dd, 1H, J=10, J'=4 Hz), 5.51 (dd, 1H, J=4, J'=1 Hz), 5.55 (dd, 1H, J=10, J'=4 Hz), 5.77 (d, 1H, J=4 Hz), 7.07 (d, 2H, J=8 Hz), 7.33 (d, 2H, J=8 Hz). MS (DIC/$NH_3$): m/z: 613 $(M+NH_4)^+$, 437, 348, 331.

6) N-[4-(2,3,4,6-Tetra-O-acetyl-α-D-galactopyranosyl)benzyloxycarbonyl]daunorubicin (6)

Preparation:

20 mg of daunorubicin are dissolved in 0.8 ml of dimethylformamide. 23 mg of 5 and one drop of triethylamine are added to this solution, which is stirred under argon for 10 minutes at room temperature.

The reaction medium is taken up with ethyl acetate and then extracted with a saturated solution of NaCl.

The organic phase is dried over anhydrous sodium sulfate, filtered and evaporated to dryness under reduced pressure. The 50 mg of dry residue obtained are purified on a column of 60H silica (solvent: acetone/cyclohexane: 45/55 v/v) to give 13 mg of the expected product 6 (yield=32%).

Compound 6: $C_{49}H_{53}NO_{22}$. M=1007. Amorphous. $[\alpha]_D^{20}=+278°$ (c 0.7, CHCl$_3$). $^1$H NMR (270 MHz, DMSO): δ ppm: 1.08 (d, 3H, J=7 Hz), 1.40–2.20 (m, 4H), 1.76 (s, 3H), 1.91 (s, 3H), 1.96 (s, 3H), 2.08 (s, 3H), 2.20 (s, 3H), 2.91 (s, 2H), 3.31 (m, 1H), 3.66 (ddt, 1H, J=12, J'=8, J''=4 Hz), 3.93–4.00 (m, 5H), 4.13 (dd, 1H, J=7, J'=4 Hz), 4.30 (ddd, J=7, J'=6, J''=1 Hz), 4.70 (d, 1H, J=6 Hz), 4.88 (m, 3H), 5.10 (dd, 1H, J=10, J'=4 Hz), 5.17 (m, 1H), 5.37 (m, 2H), 5.53 (s, 1H), 5.74 (d, 1H, J=4 Hz), 6.84 (d, 1H, J=8 Hz), 7.03 (d, 2H, J=8 Hz), 7.26 (d, 2H, J=8 Hz), 7.64 (m, 1H), 7.88 (m, 2H). MS (DIC/NH$_3$): m/z: 1025 (M+NH$_4$)$^+$, 376.

7) N-[4-(α-D-Galactopyranosyl)benzyloxycarbonyl]daunorubicin (7)

Preparation:

A solution of 9 mg of 6 in 1 ml of 0.1N sodium methanolate is stirred and kept at 0° C. for 15 minutes. The medium is neutralized by the addition of Amberlite IRC 120H$^+$ resin and then filtered. The filtrate is evaporated to dryness under reduced pressure to give 6.7 mg of the pure compound 7 (yield=89%).

Compound 7: $C_{41}H_{45}NO_{18}$. M=839. Amorphous. $[\alpha]_D^{20}=+243°$ (c 0.01, MeOH). $^1$H NMR (270 MHz, CD$_3$OD): δ ppm: 1.34 (d, 3H), 1.50–4.00 (m, 11H), 4.50–5.50 (m, 9H), 7.06 (d, 2H, J=8 Hz), 7.23 (d, 2H, J=8 Hz), 7.30–7.60 (m, 3H). MS (DIC/NH$_3$): m/z: 571, 554, 459, 383, 286, 164.

EXAMPLE 2

Synthesis of N-[2-(α-D-galactopyranosyl)benzyloxycarbonyl]daunorubicin (14)

According to scheme II, the desired product (14) is obtained by using the glycoside 8 as the starting material and by using the same reaction sequences as those described in Example 1, namely (i) benzyl bromination; (ii) solvolysis of the brominated derivative; (iii) activation of the OH group with succinimidyl chloroformate; and (iv) coupling of 12 with daunorubicin and deprotection of the OH groups in the sugar residue.

1) 2-Bromomethylphenyl 2,3,4,6-tetra-O-acetyl-α-D-galactopyranoside (9)

Preparation:

From 2-methylphenyl 2,3,4,6-tetra-O-acetyl-α-D-galactopyranoside 8 (ref.: P. M. DEY, Chemistry and Industry (London), 39, 1637, 1967) by using NBS/CCl$_4$ (yield=80%).

Compound 9: $C_{21}H_{25}BrO_{10}$. M=517. $^1$H NMR (200 MHz, CDCl$_3$): δ ppm: 1.96 (s, 3H), 2.04 (s, 3H), 2.11 (s, 3H), 2.19 (s, 3H), 4.14 (m, 2H), 4.40 (t, 1H, J=6 Hz), 4.60 (ABq, 2H, J=9 Hz), 5.38 (dd, 1H, J=11 and 4 Hz), 5.50–5.75 (m, 2H), 5.85 (d, 1H, J=4 Hz), 7.00–7.40 (m, 4H).

2) 2-Hydroxymethylphenyl 2,3,4,6-tetra-O-acetyl-α-D-galactopyranoside (11)

Preparations:

a) from 9 by using AgNO$_3$ (yield=21%);

b) from 10 by using NaBH$_4$/THF/MeOH (yield=80%).

Compound 11: $C_{21}H_{26}O_{11}$. M=454. M.p.=96° C. $^1$H NMR (200 MHz, CDCl$_3$): δ ppm: 1.98 (s, 3H), 2.03 (s, 3H), 2.09 (s, 3H), 2.19 (s, 3H), 4.15 (m, 2H), 4.43 (t, 1H, J=6 Hz), 4.57 (d, 1H, J=12.5 Hz), 4.89 (d, 1H, J=12.5 Hz), 5.30–5.60 (m, 3H), 5.72 (d, 1H, J=4 Hz), 7.00–7.40 (m, 4H).

3) 2-Formylphenyl 2,3,4,6-tetra-O-acetyl-α-D-galactopyranoside (10)

Preparation:

From 8 by bromination and then by using AgNO$_3$ (yield=52%).

Compound 10: $C_{21}H_{24}O_{11}$. M=452. $^1$H NMR (200 MHz, CDCl$_3$): δ ppm: 2.00 (s, 3H), 2.06 (s, 3H), 2.08 (s, 3H), 2.19 (s, 3H), 4.18 (m, 2H), 4.43 (t, 1H, J=6 Hz), 5.38 (d, 1H, J=11 Hz), 5.40–5.60 (m, 2H), 5.84 (d, 1H, J=4 Hz), 7.19 (t, 1H, J=8 Hz), 7.30 (d, 1H, J=8 Hz), 7.58 (t, 1H, J=8 Hz), 7.91 (d, 1H, J=8 Hz), 10.56 (s, 1H).

4) 2,5-Dioxopyrrolidin-1yl 2-(2,3,4,6-tetra-O-acetyl-α-D-galactopyranosyl)benzyl carbonate (12)

Preparation:

From 11 by using succinimidyl chloroformate (cf. preparation of 5, yield=72%).

Compound 12: $C_{26}H_{29}NO_{15}$. M=595. $^1$H NMR (200 MHz, CDCl$_3$): δ ppm: 1.98 (s, 3H), 1.99 (s, 3H), 2.06 (s, 3H), 2.17 (s, 3H), 2.87 (bs, 4H), 4.15 (m, 2H), 4.43 (t, 1H, J=6 Hz), 5.16 (d, 1H, J=12 Hz), 5.33 (dd, 1H, J=12 and 4 Hz), 5.40–5.90 (m, 5H), 7.10 (t, 1H, J=8 Hz), 7.20–7.50 (m, 3H).

N-[2-(2,3,4,6-Tetra-O-acetyl-α-D-galactopyranosyl) benzyloxycarbonyl]daunorubicin (13)

Preparation:

From 12 and daunorubicin (yield=85%) according to the protocol described for 6.

Compound 13: M.p.=130° C. $[\alpha]_D^{20}=+216°$ (c 0.25, CHCl$_3$). $C_{49}H_{53}NO_{22}$. M=1007. $^1$H NMR (200 MHz, CDCl$_3$): δ ppm: 1.87 (s, 3H), 2.00 (s, 3H), 2.08 (s, 3H), 2.12 (s, 3H), 2.41 (s, 3H), 2.94 (d, 1H, J=18 Hz), 3.23 (d, 1H, J=18 Hz), 3.66 (s, 1H), 3.70–4.20 (m, 6H), 4.08 (s, 3H), 5.10 (ABq, 2H, J=9 Hz), 5.20–5.70 (m, 7H), 5.85 (d, 1H, J=4 Hz), 7.00–7.50 (m, 4H), 7.78 (t, 1H, J=8 Hz), 8.03 (d, 1H, J=8 Hz), 13.28 (s, 1H), 13.98 (s, 1H).

6) N-[2-(α-D-Galactopyranosyl)benzyloxycarbonyl]daunorubicin (14)

Preparation:

From 13 by using MeONa(cat.)/MeOH (cf. preparation of 7, yield=83%).

$C_{41}H_{45}NO_{18}$. M=839. M.p.=130° C.

EXAMPLE 3

Synthesis of N-(4-hydroxybenzyloxycarbonyl)daunorubicin β-D-glucuronide (22)

According to scheme III, the coupling of methyl per-O-acetyl-D-glucuronate with paracresol is carried out in CH$_2$Cl$_2$ solution in the presence of TMSOTf as a catalyst.

The derivative 22 is then prepared by means of the same reaction sequences as those of Examples 1 and 2, except for the additional deprotection of the carbomethoxy group, which is carried out by mixing in MeOH in the presence of BaO.

1) Methyl (4-bromomethylphenyl 2,3,4-tri-O-acetyl-β-D-glucopyranoside)uronate (16)

This is obtained (yield=79%) by the method indicated for 2 (see Example 1) from methyl (4-methylphenyl 2,3,4-tri-O-acetyl-β-D-glucopyranoside)uronate (15), which is obtained as described by G. N. BOLLENBACK, J. Am. Chem. Soc., 1955, 77., 3310–3315.

$C_{20}H_{23}O_{10}Br$. M=503. M.p. =144°–146° C. (ethanol). $[\alpha]_D^{20}=+3°$ (c 0 85, CHCl$_3$). IR (CDCl$_3$): 1758 cm$^{-1}$ (CO). $^1$H NMR (90 MHz, CDCl$_3$): δ ppm: 2.00 (s, 9H), 3.66 (s, 3H), 4.16 (m, 1H), 4.43 (s, 2H), 5.03–5.36 (m, 4H), 6.89–7.33 (AB, 4H). MS (DIC/NH$_3$): m/z: 521 (M+NH$_4$)$^+$.

2) Methyl (4-hydroxymethylphenyl 2,3,4-tri-O-acetyl-β-D-glucopyranoside)uronate (18) and methyl (4-formylphenyl 2,3,4-tri-O-acetyl-β-D-glucopyranoside)uronate (17)

These are obtained from 16 (1.2 g, 2.3 mmol) by the method indicated above for obtaining 4 (Example 1). Chromatography of the residue on silica gel using a hexane/ethyl acetate mixture (2:1, v/v) as the eluent makes it possible to isolate some starting material 16 (100 mg), 18 (650 mg, 38%) and then 17 (200 mg, 12%).

Compound 18: $C_{20}H_{24}O_{11}$. M=440. M.p.=134°–136° C. $[\alpha]_D^{20}$=−45° (c 0.55, $CHCl_3$). IR (KBr): 3556 $cm^{-1}$ (OH), 1758 $cm^{-1}$ (CO). $^1H$ NMR (90 MHz, $CDCl_3$): δ ppm: 1.96 (s, 9H), 3.63 (s, 3H), 3.96–4.20 (m, 2H), 4.53 (s, 2H), 4.96–5.33 (m, 4H), 7.20 and 6.86 (AB, 4H). MS (DIC/$NH_3$): m/z: 458 (M+$NH_4$)$^+$.

Compound 17: $C_{20}H_{22}O_{11}$. M=438. M.p.=170°–172° C. $[\alpha]_D^{20}$=−31° (c 0.95, $CHCl_3$). IR ($CDCl_3$): 1758 $cm^{-1}$ (C=O, ester), 1698 $cm^{-1}$ (C=O, PhCHO). $^1H$ NMR (90 MHz, $CDCl_3$): δ ppm: 2.12 (s, 9H), 3.72 (s, 3H), 4.21–4.39 (m, 1H), 5.30–5.56 (m, 4H), 7.07–8.03 (dd, 4H), 9.91 (s, 1H). MS (DIC/$NH_3$): m/z: 456 (M+$NH_4$)$^+$.

3) 2,5-Dioxopyrrolidin-1-yl 4-(methyl (2,3,4-tri-O-acetyl-β-D-glucopyranosyl)uronate)benzyl carbonate (19)

Preparation:

A solution of 18 (170 mg, 0.39 mmol) and triethylamine (54 μl, 0.39 mmol) in anhydrous methylene chloride (4 ml) is added dropwise under argon to a solution of DSC (197 mg, 0.77 mmol) in 8 ml of acetonitrile. After stirring for 24 h at room temperature, the medium is filtered and the filtrate is concentrated to dryness. The product 19 is obtained (117 mg, 52%) in the form of a colourless syrup.

Compound 19: $C_{25}H_{27}NO_{15}$. M=581. $[\alpha]_D^{20}$=+3° (c 0.85, $CHCl_3$). IR ($CDCl_3$): 1747 $cm^{-1}$ (C=O). $^1H$ NMR (90 MHz, $CDCl_3$): δ ppm: 2.08 (s, 9H), 2.82 (s, 4H), 3.73 (s, 3H), 4.24 (d, 1H, J=9), 5.13–5.44 (m, 4H), 6.96–7.44 (m, 4H). MS (DIC/$NH_3$): m/z: 599 (M+$NH_4$)$^+$.

4) N-[4-(Methyl (2,3,4-tri-O-acetyl-β-D-glucopyranosyl)uronate)benzyloxycarbonyl]daunorubicin (20)

Preparation:

By the method indicated for obtaining 6 and 13 (yield=70%) (see Examples 1 and 2).

Compound 20: Amorphous product. $C_{48}H_{51}NO_{22}$. M=993. $[\alpha]_D^{20}$=+112° (c 0.06, $CHCl_3$). $^1H$ NMR (250 MHz, $CDCl_3$): δ ppm: 1.32 (d, 3H, J=6 Hz), 1.74 (s, 1H), 1.77 and 1.95 (AB, 2H, J=5, J'=12), 2 07 (3s, 9H), 2.12–2.38 (AB, 2H), 2.44 (s, 3H), 2.97 and 3.26 (AB, 1H, J=20), 3.70 (m, 1H), 3.73 (s, 3H), 3.92 (broad s, 1H), 4.12 (s, 3H), 4.19 (m, 1H), 5.00 (s, 2H), 5.14 (d, 1H, J=7), 5.68 (dd, J=3, J'=7, 1H) 5.53 (d, 1H, J=3.5), 6.98 and 7.28 (AB, 4H, J=8), 7.43 (d, 1H, J=8), 7.83 (t, 1H, J=J'=8), 8.07 (d, 1H, J=8), 13.33 and 14.00 (2s, 2H). MS (FAB): m/z: 1016 (M+Na)$^+$.

5)N-[4-(Methyl (β-D-glucopyranosyl)uronate)benzyloxyrcarbonyl]daunorubicin (21)

By treatment of 20 with MeONa/MeOH (cf. preparation of 7 and 14, Examples 1 and 2, yield=78%). Red syrup. $C_{42}H_{45}NO_{19}$. M=867. $[\alpha]_D^{20}$=+140° (c 0.02, $CH_3OH$). MS (252C FPD): m/z: 890 (M+Na)$^+$.

6)N-(4-Hydroxybenzyloxycarbonyl)daunorubicin β-D-glucuronide (22)

The compound 21 (2.7 mg) is dissolved in 0.2 ml of MeOH and the solution is stirred for 3 h at room temperature in the presence of barium oxide. The medium is then neutralized by the addition of Amberlite IR 50 H+ resin and, after filtration, is concentrated under reduced pressure. 1.8 mg of pure 22 are isolated by precipitation in an MeOH/$Et_2O$/hexane mixture. $C_{41}H_{43}NO_{19}$. M=853. $[\alpha]_D^{20}$=+2° (c 0.06, MeOH).

EXAMPLE 4

Synthesis of N-[2-((β-D-glucopyranosyl)uronic acid)benzyloxycarbonyl]daunorubicin (27c)

According to scheme IV, methyl (2-bromomethylphenyl 2,3,4-tri-O-acetyl-β-D-glucopyranoside)uronate 23 obtained from methyl (2-methylphenyl 2,3,4-tri-O-acetyl-β-D-glucopyranosyl)uronate, as described in G. N. BOLLENBACK et al., (J. Am. Chem. Soc., 1955, 77, 3310) is converted to the product 24 (and/or the product 25) and the product 24 is then converted to the product 26.

In this case, to bond the arm to the anthracycline, the carbonate 26 is prepared by means of commercially available 4-nitrophenyl chloroformate.

The compound 27c (desired prodrug) is subsequently obtained as described above in Examples 1, 2 and 3.

Methyl (2-bromomethylphenyl 2,3,4-tri-O-acetyl-β-D-glucopyranoside)uronate (23)

Preparation:

A solution of methyl (2-methylphenyl 2,3,4-tri-O-acetyl-β-D-glucopyranosyl)uronate (940 mg, 2.2 mmol) (ref.: G. N. BOLLENBACK, J. Am. Chem. Soc., 77, 3310– 3315, 1955), NBS (509 mg, 2.86 mmol) and 52 mg of benzoyl peroxide in 25 ml of $CCl_4$ is refluxed for 12 h. After conventional extraction and purification on a column of silica, 880 mg of 23 (80%) are isolated.

Compound 23: $C_{20}H_{23}BrO_{10}$. M=503. $^1H$ NMR (200 MHz, $CDCl_3$): δ ppm: 2.05 (s, 3H), 2.07 (s, 3H), 2.11 (s, 3H), 3.74 (s, 3H), 4.19 (d, 1H, J=9 Hz), 4.35 and 4.65 (2d, $CH_2$, J=12 Hz), 5.23 (m, 1H), 5.38 (m, 3H), 7.05 (m, 2H), 7.32 (m, 2H).

2) Methyl (2-hydroxymethylphenyl 2,3,4-tri-O-acetyl-β-D-glucopyranoside)uronate (24) and methyl (2-formylphenyl 2,3,4-tri-O-acetyl-β-D-glucopyranoside)uronate (25)

Preparation:

A solution of the brominated derivative 23 (690 mg, 1.37 mmol) in 14 ml of an acetone/water solution (50/50) is stirred for 2 h in the presence of 631 mg (3.7 mmol) of $AgNO_3$. After filtration and conventional extraction, 80 mg of the aldehyde 25 (13%) and 340 mg of the alcohol 24 (56%) are isolated by chromatography on silica gel.

Characteristics of 24: $C_{20}H_{24}O_{11}$. M=440. M.p.= 143°–147° C. $[\alpha]_D^{20}$=−26° (c 0.9, $CHCl_3$) NMR (200 MHz, $CDCl_3$): 2.05 (s, 3H), 2.07 (s, 3H), 2.11 (s, 3H), 3.72 (s, 3H), 4.13 (d, J=9 Hz, H-5), 4.48 and 4.77 (2d, J=12.5 Hz, 2H), 5.15 (d, J=7.2 Hz, 1H), 5.35 (m, 3H), 7.02 (d, J=8 Hz, 1H), 7.11 (t, J=7.2 Hz, 1H), 7.29 (d, J=6.8 Hz, 1H), 7.34 (t, J=7,4 Hz, 1H) ppm. IR ($CH_2Cl_2$): 3540, 3030, 2960, 1760, 1605, 1590, 1490, 1455, 1440, 1375, 1225, 1140, 1090, 1075, 1040 $cm^{-1}$. SM (FAB$^+$) m/z : 463 (M+Na)$^+$.

Compound 25: $C_{20}H_{22}O_{11}$. M=438. $^1H$ NMR (200 MHz, $CDCl_3$): δ ppm: 2.08 (s, 9H), 3.75 (s, 3H), 4.25 (d, 1H, J=9 Hz), 5.34 (m, 4H), 7.15 (t, 1H, J=8.6 Hz), 7.25 (d, 1H, J=7.3 Hz), 7.58 (t, 1H, J=7 Hz), 7.26 (d, 1H, J=7.6 Hz), 10.34 (s, 1H).

3) 4-Nitrophenyl 2-(methyl (2,3,4-tri-O-acetyl-β-D-glucopyranosyl)uronate)benzyl carbonate (26)

Preparation:

A solution of 24 (33 mg, 0.075 mmol) in 0.021 ml of pyridine and 0.2 ml of ethyl acetate is stirred for 12 h at room temperature in the presence of 46 mg (0.22 mmol) of paranitrophenyl chloroformate. After filtration and evaporation of the solvents, purification on a silica plate gives 45 mg of 26 (quantitative yield).

Compound 26: $C_{27}H_{27}NO_{15}$. M=605. M.p.=67°–70° C. $[\alpha]_D^{20}$=+2° (c 1, $CDCl_3$). $^1H$ NMR (200 MHz, $CHCl_3$): δ ppm: 2.07 (s, 9H), 3.74 (s, 3H), 4.24 (broad d, J=8.5 Hz, H-5), 5.3 (m, 6H), 7.10 (m, 2H), 7.39 (m, 4H), 8.27 (d, J=9 Hz, 2H).

4) N-[2-(Methyl (2,3,4-tri-O-acetyl-β-D-glucopyranosyl)uronate)benzyloxycarbonyl]daunorubicin (27a)

Preparation:

A solution of daunorubicin (15.8 mg, 0.03 mmol), the glycoside 26 (1.1 eq., 19.8 mg) and Et$_3$N (3.6 mg, 1.2 eq.) in 0.1 ml of DMF is stirred for 12 hours. After conventional extraction, purification on a silica plate gives 20 mg (67%) of 27.

Compound 27a: C$_{48}$H$_{51}$NO$_{22}$, M=993 , M.p. =153°–155° C. [α]$_D^{20}$=+122° (c 0.4, CHCl$_3$). $^1$H NMR (200 MHz, CDCl$_3$): δ ppm: 1.31 (d, 3H, J=6.4 Hz), 2.06 (s, 6H), 2.09 (s, 3H), 2.42 (s, 3H), 2.91 and 3.24 (2d, J=19 Hz, 2H), 3.60 (s, 3H), 4.08 (s, 3H), 4.20 (m, 2H), 5.00–5.32 (m, 8H), 7.05 (m, 2H), 7.26 (m, 2H), 7.38 (d, J=7.4 Hz, 1H), 7.77 (t, J=7.4 Hz, 1H), 8.03 (d, J=7.4 Hz, 1H), 13.24 (s, 1H), 12.57 (s, 1H). MS: [M+K]$^+$=1032.

N-[2-(Methyl (β-D-glucopyranosyl)uronate)benzyloxycarbonyl]daunorubicin (27b)

By treatment of 27a with MeONa/MeOH (cf. preparation of 7 and 14, Examples 1 and 2). Red solid. C$_{42}$H$_{45}$O$_{19}$N. M=867.

6) N-[2-((β-D-Glucopyranosyl)uronic acid)benzyloxycarbonyl]daunorubicin (27c)

By treatment of 27b with BaO or K$_2$CO$_3$ (cf. preparation of 22 in Example 3). Red solid. C$_{41}$H$_{43}$NO$_{19}$. M=853.

EXAMPLE 5

Synthesis of N-[2-hydroxybenzyloxycarbonyl]daunorubicin (32)

According to scheme V, the derivative 32 is prepared either by synthesis from the derivative 28 (2-tert-butyldimethylsilyloxybenzaldehyde), which is reduced in the presence of NaBH$_4$ to give the compound 29; activation with 4-nitrophenyl chloroformate gives the derivative 30, which is condensed with daunorubicin; the product 32 is then obtained by deprotection with KF; or by enzymatic hydrolysis of the product 14 (see Example 2) with α-galactosidase.

1) N-[2-Hydroxybenzyloxycarbonyl]daunorubicin (32)

a) Enzymatic hydrolysis of 14:

The compound 14 (1 mg) is dissolved in 0.02 ml of DMF. 1 ml of a 100 mM solution of HEPES in distilled water is then added. After the addition of α-galactosidase (2 U, EC 3.2.1.22, Sigma, n° G-8507), the reaction mixture is stirred for 2 hours at 35° C. The compound 32 is obtained in quantitative yield after hydrolysis and extraction.

b) Hydrolysis of 31:

The silylated derivative 31 (2 mg, 0.0025 mmol) is dissolved in THF (0.1 ml). 0.2 ml of an aqueous solution of KF (containing 0.1 g per ml) is then added. After 12 hours at room temperature, customary extraction gives 32.

Characteristics of 32: C$_{35}$H$_{35}$NO$_{13}$. M=677. $^1$H NMR (200 MHz, CDCl$_3$): δ ppm: 1.26 (d, J=6 Hz, 3H), 2.42 (s, 3H), 2.89 (d, J=20 Hz, 1H), 3.24 (d, J=20 Hz, 1H), 3.61 (s, 1H), 4.07 (s, 3H), 4.43 (S, 1H), 5.00 (s, 2H), 5.28 (broad s, 1H), 5.47 (d, J=2 Hz, 1H), 6.7–7.3 (m, 4H), 7.40 (d, J=8 Hz, 1H), 7.80 (t, J=8 Hz, 1H), 8.00 (d, J=8 Hz, 1H), 8.78 (s, 1H), 13.27 (s, 1H), 13.96 (s, 1H).

The product 32 can advantageously be condensed with a sugar to give the products 27a, 27b or 27c.

2) 2-Tert-butyldimethylsilyloxybenzaldehyde (28)

Preparation:

A solution of 2-hydroxybenzaldehyde (500 mg, 0.44 ml, 4.09 mmol), imidazole (685 mg) and tert-butyldimethylsilyl chloride (680 mg) in DMF is stirred for 24 hours at room temperature. After hydrolysis and customary extraction, chromatography gives 28 (890 mg, 93%).

Compound 28: C$_{13}$H$_{20}$O$_2$Si. M=236. $^1$H NMR (200 MHz, CDCl$_3$): δ ppm: 0.28 (s, 6H), 1.00 (s, 9H), 0.91 (d, J=8 Hz, 1H), 7.02 (t, J=8 Hz, 1H), 7.46 (t, J=8 Hz, 1H), 7.81 (d, J=8 Hz, 1H), 10.47 (s, 1H).

3) 2-Tert-butyldimethylsilyloxybenzyl alcohol (29)

Preparation:

A solution of 28 (200 mg) in methanol (5.5 ml) containing NaBH$_4$ (28 mg) is stirred for 1 hour at room temperature. 29 (140 mg, 68%) is obtained after hydrolysis and customary extraction.

Compound 29: C$_{13}$H$_{22}$O$_2$Si. M=238. $^1$H NMR (200 MHz, CDCl$_3$): δ ppm: 0.30 (s, 6H), 1.06 (s, 9H), 2.67 (s, 1H), 4.70 (s, 2H), 6.86 (d, J=8 Hz, 1H), 6.97 (t, J=8 Hz, 1H), 7.20 (t, J=8 Hz, 1H), 7.33 (d, J=8 Hz, 1H).

4) 4-Nitrophenyl 2-(tert-butyldimethylsilyloxy)benzyl carbonate (30)

Preparation:

The alcohol 29 (135 mg, 0.56 mmol) is dissolved in ethyl acetate (0.82 ml). Pyridine (0.081 ml) is then added, followed by 4-nitrophenyl chloroformate (275 mg, 2.4 eq.). After one night at room temperature, the solvent is evaporated off. Chromatography on silica gel gives the carbonate 30 (206 mg, 91%).

Characteristics of 30: C$_{20}$H$_{25}$NO$_6$Si. M=403. $^1$H NMR (200 MHz, CDCl$_3$): δ ppm: 0.27 (s, 6H), 1.03 (s, 9H), 5.32 (s, 2H), 6.86 (d, J=8 Hz, 1H), 6.96 (t, J=8 Hz, 1H), 7.1–7.5 (m, 4H), 8.21 (d, J=8 Hz, 2H).

5) N-[2-(Tert-butyldimethylsilyloxy)benzyloxycarbonyl] daunorubicin (31)

Preparation:

A solution of 30 (8.3 mg, 0.022 mmol), daunorubicin (9.6 mg, 0.018 mmol) and triethylamine (0.003 ml) in DMF (0.1 ml) is stirred for 4 hours at room temperature. After customary extraction, chromatography makes it possible to separate out 31 (6 mg, 41%) and 32 (4.5 mg, 36%).

Compound 31: C$_{41}$H$_{49}$NO$_{13}$Si. M=791. $^1$H NMR (200 MHz, CDCl$_3$): δ ppm: 0.20 (s, 6H), 0.96 (s, 9H), 1.30 (d, J=6 Hz, 1H), 2.42 (s, 3H), 2.9 (m, 2H), 3.24 (d, J=20 Hz, 1H), 3.65 (broad s, 1H), 3.90 (broad s, 1H), 4.09 (s, 3H), 4.48 (s, 1H), 5.06 (s, 2H), 5.28 (s, 1H), 5.52 (d, J=2 Hz, 1H), 6.8–7.0 (m, 4H), 7.42 (d, J=8 Hz, 1H), 7.80 (t, J=8 Hz, 1H), 8.03 (d, J=8 Hz, 1H), 13.31 (s, 1H), 14.0 (s, 1H).

EXAMPLE 6

Synthesis of N-[4-(β-D-glucopyranosyl)benzyloxycarbonyl]daunorubicin (37)

According to scheme VI, phase transfer catalysis is used to condense peracetyl-α-D-glucose with p-hydroxybenzaldehyde, and the glycoside 33 is converted to the compound 37 according to Examples 1, 2, 3, 4 or 5 above.

1) 4-Formylphenyl 2,3,4,6-tetra-O-acetyl-β-D-glucopyranoside (33)

Preparation:

2,3,4,6-Tetra-O-acetyl-α-D-bromoglucose (2 g, 4.8 mmol) is dissolved in 20 ml of chloroform. A mixture of p-hydroxybenzaldehyde (585 mg, 4.8 mmol) and benzyltriethylammonium bromide (1.1 g), dissolved beforehand in a 1.25N solution of sodium hydroxide (10 ml), is added to the above solution and the reaction medium is refluxed for 24 h. Extraction is carried out with 50 ml of water. The organic phase obtained is washed successively with a 1N solution of NaOH (2×50 ml), a solution of HCl (1N) and then water, dried and concentrated to dryness. The crude product obtained is then recrystallized from ethanol to give 33 (0.5 g, 23%).

Compound 33: C$_{21}$H$_{24}$O$_{11}$. M=452. M.p.=150°–152° C. [α]$_D^°$=+28° (c 0.5, CHCl$_3$) IR (CHCl$_3$): 1757 cm$^{-1}$ (C=O, ester), 1698 cm$^{-1}$ (C=O, aldehyde). $^1$H NMR (90 MHz, CDCl$_3$): δ ppm: 2.09 (s, 12H), 3.99 (m, 1H), 4.22 (AB, 1H), 4.33 (AB, 1H), 5.13–5.48 (m, 4H), 7.15 and 7.89 (AB, 4H, J=12 Hz), 9.96 (s, 1H). MS (DIC): m/z: 470 (M+NH$_4$)$^+$.

2) 4-Hydroxymethylphenyl 2,3,4,6-tetra-O-acetyl-β-D-glucopyranoside (34)

Preparation:

This is obtained from 33 by the method used to prepare 11 from 10 (see Example 2), and crystallizes from ethanol (yield=92%).

Compound 34: C$_{21}$H$_{26}$O$_{11}$. M=454. M.p.=102°–103° C. [α]$_D^{20}$=–18° (c 0 5, CHCl$_3$) IR (CDCl$_3$): 1757 cm$^{-1}$ (C=O, ester). $^1$H NMR (200 MHz, CDCl$_3$): δ ppm: 1.98–2.03 (4s, 12H, 4 OAc), 3.75–3.84 (m, 1H, H- 5),4.11 (AB, J$_{gem}$ =6 Hz, H-6a), 4.57 (s, 1H, OH), 4.99–5.25 (m, 4H, H-1, H-2, H-3 and H-4), 6.92 and 7.24 (AB, J$_{gem}$ =8 Hz, 4H, Ph). MS (DIC): m/z: 472 (M+NH$_4$)$^+$.

3) 2,5-Dioxopyrrolidin-1yl 4-(2,3,4,6-tetra-O-acetyl-β-D-glucopyranosyl)benzyl carbonate (35)

Preparations:

Method A: By activation of the compound 34 (617 mg, 1.36 mmol) with succinimidyl chloroformate (cf. preparation of 5, Example 1). The pure product 35 (780 mg, 95%) is obtained.

Method B: By activation of the compound 34 with DSC (cf. preparation of 19, Example 3) (yield=80%).

Compound 35: C$_{26}$H$_{29}$O$_{15}$N. M=595. M.p.=164° C. [α]$_D^{20}$=+18° (c 0.09, CHCl$_3$) IR (KBr): 1791 cm$^{-1}$ (C=O). $^1$H NMR (200 MHz, CDCl$_3$): δ ppm: 2.02 (4s, 12H), 2.77 (s, 4H), 3.81 (m, 1H), 4.14 (AB, J=12 Hz, H), 4.24 (AB, J=5 Hz, 1H), 5.02–5.31 (m, 6H), 6.95–7.31 (AB, J=12 Hz, 4H). MS (DIC/NH$_3$): m/z: 613 (M+NH$_4$)$^+$.

4) N-[4-(2,3,4,6-Tetra-O-acetyl-β-D-glucopyranosyl)benzyloxycarbonyl]daunorubicin (36)

Preparation:

By condensation of the compound 35 (26 mg, 0.04 mmol) with daunorubicin (20 mg, 0.04 mmol) (cf. preparation of 6 and 13, Examples 1 and 2). The pure derivative 36 (25 mg, 90%) is isolated in the form of a red lac.

Compound 36: C$_{49}$H$_{53}$O$_{22}$N. M=1007. [α]$_D^{20}$=135° (c 0.04, CHCl$_3$). IR (CDCl$_3$): 3435 cm$^{-1}$ (OH), 1758 cm$^{-1}$ (C=O). $^1$H NMR (400 MHz, CDCl$_3$): δ ppm: 1.29 (d, H, J=5 Hz), 1.79 (AB, 1H, J=3.5 Hz), 1.91 (AB, 1H, J$_{gem}$=14 Hz), 2.07 (4s, 12H), 2.15 (AB, 1H, J=3.5 Hz), 2.35 (AB, 1H, J=18 Hz), 2.50 (s, 3H), 2.95 (AB, H, J=18 Hz), 3.25 (AB, 1H, J=18 Hz), 3.70 (m, 1H), 3.84–3.90 (m, 1H), 3.92 (1H, OH), 4.11 (s, 3H, OMe), 4.17 (AB, 1H, J=2 Hz), 4.24 (m, 1H), 4.30 (AB, 1H, J=12 Hz), 5.00 (s, 2H), 5.08 (d, 1H, J=7 Hz), 5.14 (d, 1H, J=8.5 Hz), 5.17 (t, 1H, J=J'=10 Hz), 5 24–5 34 (m, 3H), 5 23 (dd, 1H, H-1'J<0 5 Hz, J'=3.5 Hz), 6.96 and 7.28 (AB, 4H), 7.42 (d, 1H, J=8 Hz), 7.82 (t, J=J'=8 Hz), 8.07 (d, 1H, J=8 Hz), 13.25 (s, 1H), 14.00 (s, 1H). MS (DIC/NH$_3$): m/z: 1026 (M+NH$_4$)$^+$.

5) N-[4-(β-D-Glucopyranosyl)benzyloxycarbonyl]daunorubicin (37)

By reacting MeONa(cat.)/MeOH with the compound 36 (91%), 37 is obtained in the form of a red syrup.

C$_{41}$H$_{45}$O$_{18}$N. M=839. [α]$_D^{20}$=+200° (c 0.001, CH$_3$OH). IR (KBr): 3422 cm$^{-1}$ (OH), 1617 cm$^{-1}$ (C=O). MS (FAB): m/z: 838 (M+1)$^+$.

EXAMPLE 7

Preparation of N-[4-hydroxybenzyloxycarbonyl]daunorubicin (38)

According to scheme VII, the derivative 38 is prepared either by synthesis or by enzymatic hydrolysis according to Example 5 (derivative 32).

1) N-[4-Hydroxybenzyloxycarbonyl]daunorubicin (38)

The compound 37 (3 mg, 3.68 μmol) is dissolved in a buffer solution of sodium acetate of pH 5.5 (0.46 ml), and a suspension of enzyme (20 μl, 5 U of β-D-glucosidase (20 mg of β-D-glucosidase in 400 μl of water) plus 80 μl of ethanol) is then added at 37° C. over 15 min. The enzymatic reaction is complete. The mixture is filtered, the solvents are evaporated off and the residue is then chromatographed on silica gel by means of a CH$_2$Cl$_2$/CH$_3$OH mixture (9:1, v/v). The pure derivative 38 (1.5 mg, 60%) is isolated in the form of a syrupy red liquid.

C$_{35}$H$_{35}$O$_{13}$N. M=676.

The compound 38 can advantageously be condensed with another sugar (glucuronic acid derivative, for instance), to give the products 20, 21 or 22.

2) 4-Dimethyl-thexylsilyloxybenzyl alcohol (39)

2.8 g (41.2 mmol) of imidazole are added to a solution of 4-hydroxybenzyl alcohol (2.55 g, 20.6 mmol) in 25 ml of anhydrous DMF. The mixture is stirred at room temperature until a clear solution is obtained, and is then cooled to 0° C. under argon. 4.4 ml (22.6 mmol) of t-hexyldimethylsilyl chloride are then added. After stirring for 48 h at 0° C., the organic phase is washed with water, dried over Na$_2$SO$_4$ and evaporated under reduced pressure to give 39 (3.7 g, 68%) in the form of a gum.

C$_{15}$H$_{26}$O$_2$Si. M=266.44. IR (CDCl$_3$): 3304 cm$^{-1}$ (OH), 2960 cm$^{-1}$ (CH). $^1$H NMR (90 MHz, CDCl$_3$): δ ppm: 0.00 (s, 6H, CH$_3$Si), 0.83 (d, 6H, CH$_3$CCSi, J=5 Hz), 0.83 (d, 6H, CH$_3$CSi), 1.50 (m, 1H, CHCSi), 4.50 (s, 2H, CH=Ph), 6.67–7.03 (AB, J$_{gem}$=6 Hz, 4H, Ph). MS (DIC): m/z: 284 (M+NH$_4$)$^+$.

3) 2,5-Dioxopyrrolidin-1-yl 4-dimethyl-thexylsilyloxybenzyl carbonate (40)

1.85 g (10 mmol) of the compound 35 and 0.8 ml of pyridine are added to a solution of DSC (1.39 g, 5 mmol) in anhydrous ethyl acetate (50 ml). After stirring for 24 h at room temperature, the mixture is filtered and the filtrate is concentrated under reduced pressure to give 40 (1.84 g, 91%) in the form of a gum.

C$_{20}$H$_{29}$O$_6$SiN. M=407.52. IR (CDCl$_3$): 2961 cm$^{-1}$ (CH), 1296 cm$^{-1}$ (CO). $^1$H NMR (90 MHz, CDCl$_3$): δ ppm: 0.00 (s, 6H, CH$_3$Si), 0.80 (d, 6H, CH$_3$CCSi, J=5 Hz), 0.80 (s, 6H, CH$_3$CSi), 1.50 (m, 1H, CHCSi), 2.73 (s, 4H, CH$_2$CO), 4.57 (s, 2H, CH$_2$Ph), 7.16 (AB, 4H, Ph, J$_{gem}$=6 Hz). MS (DIC): m/z: 425 (M+NH$_4$)$^+$.

4) N-[4-(Dimethyl-thexylsilyloxy)benzyloxycarbonyl] daunorubicin (41)

76 μl (0.73 mmol) of Et$_3$N are added to a mixture of 40 (29 mg, 0,073 mmol) and daunomycinone (20 mg, 0.043 mmol) dissolved in 0.4 ml of anhydrous DMF; after stirring for 5 min at room temperature, extraction is carried out with ethyl acetate. The solution obtained is washed with a saturated solution of sodium chloride and then dried over Na$_2$SO$_4$ and concentrated under reduced pressure. 41 (24 mg, 70%) is isolated in the form of a red syrup.

C$_{43}$H$_{52}$SiN. M=819. [α]$_D^{20}$ =+53° (c 0.03, CHCl$_3$), IR (CDCl$_3$): 3597–3439 cm$^{-1}$ (OH), 2960 cm$^{-1}$ (CH), 1762 cm$^{-1}$ (CO). $^1$H NMR (250 MHz, CDCl$_3$): δ ppm: 0.00 (m, 6H, CH$_3$Si), 0.82 (d, 6H, J=5 Hz), 0.82 (s, 6H), 1.27 (d, 3H, J=6 Hz), 1.62 (m, 3H), 2.36 (s, 3H), 2.89 and 3.20 (AB, 2H, J=6 Hz), 3.93 (s, 1H), 4.04 (s, 3H), 4.20 (m, 1H), 4.40 (m, 1H), 4.62 (s, 2H), 5.52 (s, 1H), 5.33 (d, 1H, J=3 Hz), 5.49 (dd, 1H, J=2, J'<0.5 Hz), 6.95 and 7.19 (AB, 4H, J=3 Hz), 7.34 (d, 1H, J=9 Hz), 7.78 (t, 1H, J=J'=9 Hz), 8.00 (d, 1H, J=9 Hz). MS (DIC): m/z: 837 (M+NH$_4$)$^+$.

EXAMPLE 8

Synthesis of N-[2-(α-D-galactopyranosyl)-5-nitrobenzyloxycarbonyl]daunorubicin (48b) and N-[2-(α-D-galactopyranosyl)-5-nitrobenzyloxycarbonyl]doxorubicin (49b)

According to scheme VIII, $SnCl_4$-catalyzed glycosidation of 5-nitro-o-cresol with peracetyl-D-galactose gives the derivative 42.

Benzyl bromination, using NBS in $CCl_4$, gives a mixture of 43 and 44.

Hydrolysis of the dibrominated derivative 44 gives the aldehyde 45, which can be reduced with $NaBH_4$ to the derivative 46, whereas hydrolysis of the derivative 43 gives a mixture of 45 and 46. 4-Nitrophenyl formate is used to activate the derivative 46, and coupling of 47 with daunorubicin and doxorubicin gives the derivatives 48a and 49a respectively.

1) 2-Methyl-4-nitrophenyl 2,3,4,6-tetra-O-acetyl-α-D-galactopyranoside (42)

$SnCl_4$ (0.6 ml) is added slowly to a solution of 2-methyl-4-nitrophenol (ref.: J. S. ANDERSON and K. C. BROWN, Synthetic Commun., 13, 233–236, 1983) and 1,2,3,4,6-penta-O-acetyl-β-D-galactose (1 g, 2.56 mmol), kept at room temperature. The reaction mixture is then stirred under nitrogen for 12 hours at 60° C. After hydrolysis in iced water, extraction with $CH_2Cl_2$, followed by washing with a saturated solution of sodium bicarbonate and then water, gives 42, which is then purified by chromatography on silica gel (yield=45%).

$C_{21}H_{25}NO_{12}$. M=483. M.p.=166° C. $[\alpha]_D^{20}$=+184° (c 0.56, $CHCl_3$). IR ($CHCl_3$): 3030, 2960, 2925, 2860, 1745, 1580, 1520, 1490, 1370, 1345, 1220 cm$^{-1}$. $^1$H NMR (200 MHz, $CDCl_3$): δ ppm: 1.96 (s, 3H), 2.05 (s, 3H), 2.09 (s, 3H), 2.19 (s, 3H), 2.36 (s, 3H), 4.13 (m, 2H), 4.28 (m, 1H), 5.85 (d, J=4 Hz, 1H), 7.21 (d, J=9 Hz, 1H), 8.10 (s, 1H and d, J=9 Hz, 1H).

2) 2-Bromomethyl-4-nitrophenyl 2,3,4,6-tetra-O-acetyl-α-D-galactopyranoside (43)

Preparation:

From 42 by using NBS (1.5 eq.)/$CCl_4$ (cf. preparation of the compounds 2 and 9, Example 1, yield=51%).

Compound 43: $C_{21}H_{24}BrNO_{12}$. M=562. $^1$H NMR (200 MHz, $CDCl_3$): δ ppm: 1.96 (s, 3H), 2.06 (s, 3H), 2.12 (s, 3H), 2.20 (s, 3H), 4.13 (m, 2H), 4.32 (t, J=6 Hz, 1H), 4.59 (ABq, J=9 Hz, 2H), 5.38 (dd, J=12 and 4 Hz, 1H), 5.5–5.8 (m, 2H), 5.99 (d, J=4 Hz, 1H), 7.28 (d, J=9 Hz, 1H), 8.20 (d, J=9 Hz, 1H), 8.29 (s, 1H).

3) 2-Dibromomethyl-4-nitrophenyl 2,3,4,6-tetra-O-acetyl-α-D-galactopyranoside (44)

Preparations:

a) from 42 by using NBS (1.5 eq.)/$CCl_4$ (yield=27%);

b) from 42 by using NBS (4 eq.)/$CCl_4$ (yield=60–90% ).

Compound 44: $C_{21}H_{23}Br_2NO_{12}$. M=641. M.p.=70° C. $[\alpha]_D^{20}$=+143° (c 0.47, $CHCl_3$) IR ($CHCl_3$): 3030, 3020, 2960, 2930, 2860, 1745, 1620, 1590, 1525, 1480, 1425, 1370, 1345, 1220, 1130, 1110, 1075, 1040 cm$^{-1}$. $^1$H NMR (200 MHz, $CDCl_3$): δ ppm: 1.97 (s, 3H), 2.06 (s, 3H), 2.13 (s, 3H), 2.20 (s, 3H), 4.13 (m, 2H), 4.31 (t, J=6 Hz, 1H), 5.3–5.7 (m, 3H), 5.93 (d, J=14 Hz, 1H), 7.01 (s, 1H), 7.29 (d, J=9 Hz, 1H), 8.20 (d, J=9 Hz), 8.75 (s, 1H).

4) 2-Formyl-4-nitrophenyl 2,3,4,6-tetra-O-acetyl-α-D-galactopyranoside (45)

Preparations:

a) from 43 by using $AgNO_3$ (yield=15%);

b) from 44 by using $AgNO_3$ (yield=83%).

Compound 45: $C_{21}H_{23}NO_{13}$. M=497. M.p.=180° C. $[\alpha]_D^{20}$=+97° (c 2, $CHCl_3$) IR ($CHCl_3$): 3030, 2960, 2930, 2880, 2860, 1745, 1695, 1645, 1610, 1590, 1530, 1480, 1430, 1370, 1345, 1220, 1180, 1125, 1110, 1075, 1045 cm$^{-1}$. $^1$H NMR (200 MHz, $CDCl_3$): δ ppm: 1.98 (s, 3H), 2.05 (s, 3H), 2.08 (s, 3H), 2.20 (s, 3H), 4.13 (m, 2H), 4.35 (t, J=6 Hz, 1H), 5.3–5.6 (m, 3H), 5.99 (d, J=4 Hz, 1H), 7.46 (d, J=9 Hz, 1H), 8.41 (dd, J=9 and 2 Hz, 1H), 10.52 (s, 1H).

5) 2-Hydroxymethyl-4-nitrophenyl 2,3,4,6-tetra-O-acetyl-α-galactopyranoside (46)

Preparations:

a) from 43 by using $AgNO_3$ (yield=19%) (cf. preparation of 11 and 18);

b) from 45 by using $NaBH_4$/THF/MeOH (yield=73%).

Compound 46: $C_{21}H_{25}NO_{13}$. M=499. M.p.=140° C. $[\alpha]_D^{20}$=+152° (c 0.42, $CDCl_3$). IR ($CDCl_3$): 3700, 3600, 3030, 2970, 2940, 2860, 1750, 1630, 1625, 1595, 1585, 1370, 1350, 1210, 1130, 1110, 1075, 1035 cm$^{-1}$. NMR (200 MHz, $CHCl_3$): δ ppm: 1.97 (s, 3H), (s, 3H), 2.10 (s, 3H), 2.19 (s, 3H), 4.12 (m, 3H), 4.33 (t, J=6 Hz, 1H), 4.71 (d, J=14 Hz, 1H), 4.89 (d, J=14 Hz, 1H), 5.35–5.6 (m, 3H), 5.87 (d, J=2 Hz, 1H), 7.28 (d, J=9 Hz, 1H), 8.19 (dd, J=9 and 2 Hz, 1H), 8.32 (d, J=2 Hz, 1H).

6) 4-Nitrophenyl 2-(2,3,4,6-tetra-O-acetyl-α-D-galactopyranosyl)-5-nitrobenzyl carbonate (47)

Preparation:

From 46 and p-nitrophenyl chloroformate (yield =52% ).

Compound 47: $C_{28}H_{28}N_2O_{17}$. M=664. $^1$H NMR (200 MHz, $CDCl_3$): δ ppm: 1.93 (s, 3H), 2.04 (s, 3H), 2.09 (s, 3H), 2.19 (s, 3H), 4.12 (m, 2H), 4.30 (t, J=6 Hz, 1H), 5.3–5.6 (m, 5H), 5.93 (d, J=4 Hz, 1H), 7.34 (d, J=9 Hz, 1H), 7.44 (d, J=9 Hz, 1H), 8.2–8.4 (m, 4H).

7) N-[2-(2,3,4,6-Tetra-O-acetyl-α-D-galactopyranosyl)-5-nitrobenzyloxycarbonyl]daunorubicin (48a)

Preparation:

From 47 and daunorubicin (cf. preparation of 6, Example 1, yield=31%).

Compound 48: $C_{49}H_{52}N_2O_{24}$. M=1052. $^1$H NMR (200 MHz, $CDCl_3$): δ ppm: 1.86 (s, 3H), 2.02 (s, 3H), 2.08 (s, 3H), 2.14 (s, 3H), 2.39 (s, 3H), 2.94 (d, J=20 Hz, 1H), 3.23 (d, J=20 Hz, 1H), 3.60 (s, 1H), 4.08 (s, 3H), 5.02 (d, J=12 Hz, 1H), 5.21 (d, J=12 Hz, 1H), 5.3–5.8 (m, H), 5.93 (d, J=4 Hz, 1H), 7.18 (d, J=9 Hz, 1H), 7.40 (d, J=8 Hz, 1H), 7.80 (t, J=8 Hz, 1H), 8.02 (d, J=8 Hz, 1H), 8.17 (dd, J=9 and 2 Hz, 1H), 8.26 (broad s, 1H), 13.30 (s, 1H) and 13.99 (s, 1H).

8) N-[2-(α-D-Galactopyranosyl)-5-nitrobenzyloxycarbonyl]daunorubicin (48b)

Preparation:

From 48a by using MeONa(cat.)/MeOH (yield=83%).

Compound 48b: Amorphous. $C_{41}H_{44}N_2O_{20}$. M=884. M.p.=140° C. (decomp.).

9) N-[2-(2,3,4,6-Tetra-O-acetyl-α-D-galactopyranosyl)-5-nitrobenzyloxycarbonyl]doxorubicin (49a)

Preparation:

From 47 and doxorubicin. Yield=13%.

Compound 49a: $C_{49}H_{52}N_2O_{25}$. M=1068. $^1$H NMR (200 MHz, $CDCl_3$): δ ppm: 1.86 (s, 3H), 2.01 (s, 3H), 2.09 (s, 3H), 2.13 (s, 3H), 2.99 (s, 1H), 3.03 (d, J=20 Hz, 1H), 3.29 (d, J=20 Hz, 1H), 4.10 (s, 3H), 4.59 (s, 1H), 4.74 (s, 1H), 5.07 (d, J=12 Hz, 1H), 5.22 (d, J=12 Hz, 1H), 5.3–5.8 (m, H), 5.95 (d, J=4 Hz, 1H), 7.17 (d, J=9 Hz, 1H), 7.40 (d, J=8 Hz, 1H), 7.80 (t, J=8 Hz, 1H), 8.03 (d, J=8 Hz, 1H), 8.18 (dd, J=9 and 2 Hz, 1H), 8.27 (broad s, 1H), 13.28 (s, 1H), 14.0 (s, 1H).

10) N-[2-(α-D-Galactopyranosyl)-5-nitrobenzyloxycarbonyl]doxorubicin (49b)

By treatment of 49a with MeONa/MeOH (cf. preparation of 7 and 14, Examples 1 and 2). Red solid. $C_{41}H_{44}N_2O_{21}$. M=900.

EXAMPLE 9

Synthesis of N-[2-((β-D-glucopyranosyl)uronic acid)-5-nitrobenzyloxycarbonyl]daunorubicin (54c)

According to scheme IX, methyl (peracetyl-β-D-glucopyranosyl)uronate bromide is condensed with 2-hydroxy-5-nitrobenzaldehyde in the presence of $Ag_2O$ at room temperature. The glycoside 51 (yield=46%) is converted to the derivative 52 ($NaBH_4$/THF/MeOH, yield=70%) and the activated derivative of 52, i.e. 53 (yield=73%), reacts with daunorubicin to give the derivative 54a (yield=62%).

1) Methyl (2-formyl-4-nitrophenyl 2,3,4-tri-O-acetyl-β-D-glucopyranoside)uronate (51)

Preparation:

A solution of methyl (2,3,4-tri-O-acetyl-β-D-glucopyranosyl)uronate bromide (1.45 g, 3.64 mmol) and 2-hydroxy-5-nitrobenzaldehyde (609 mg, 3.64 mmol) in 22 ml of acetonitrile containing silver oxide (1.3 g, 5.6 mmol) is stirred for 4 hours at room temperature. After filtration of the reaction medium and evaporation of the filtrate, flash chromatography gives 800 mg of 51 (yield=46%).

Compound 51: $C_{20}H_{21}NO_{13}$. M=483. M.p.=173°–174° C. $[\alpha]_D^{20}$=–52° (c 1, $CHCl_3$) IR ($CH_2Cl_2$): 3060, 2960, 1755, 1690, 1590, 1530 $cm^{-1}$. $^1H$ NMR (200 MHz, $CDCl_3$): δ ppm: 2.09 (s, 9H), 3.73 (s, 3H), 4.40 (d, H-5, J=8.5 Hz), 5.5 (m, 4H), 7.32 (d, 1H, J=9.1 Hz), 8.42 (dd, 1H, J=9.1 and 3 Hz), 8.67 (d, 1H, J=3 Hz), 10,31 (s, 1H)

2) Methyl (2-hydroxymethyl-4-nitrophenyl 2,3,4-tri-O-acetyl-β-D-glucopyranoside)uronate (52)

Preparation:

From 51 by using $NaBH_4$/THF/MeOH (yield=70%).

Compound 52: $C_{20}H_{23}NO_{13}$. M=485. M.p.=137°–145° C. $[\alpha]_D^{20}$ =–34° (c 0.7, $CHCl_3$) IR ($CH_2Cl_2$): 3600, 3570, 3060, 2960, 1755, 1620, 1590, 1525, 1485, 1435, 1370, 1340, 1230, 1075, 1040, 900 $cm^{-1}$. $^1H$ NMR (200 MHz, $CDCl_3$): δ ppm: 2.07 (s, 3H), 2.08 (s, 3H), 2.10 (s, 3H), 2.95 (OH), 3.72 (s, 3H), 4.30 (d, H-5, J=8.7 Hz), 4.61 and 4.72 (ABq, 2H, J=13.8 Hz), 5.32 (m, 4H), 7.08 (d, 1H, J=9 Hz), 8.12 (dd, 1H, J=9 and J=2.7 Hz), 8.27 (d, 1H, J=2.7 Hz), $SM(FAB^+)$ m/z: 508 $(M+Na)^+$.

3) 4-Nitrophenyl 2-(methyl (2,3,4-tri-O-acetyl-β-D-glucopyanosyl) uronate)-5-nitrobenzyl carbonate (53)

Preparation:

From 52 and paranitrophenyl chloroformate (yield=73%).

Compound 53: $C_{27}H_{26}N_2O_{16}$. M=634 M.p.=154°–155° C. $[\alpha]_D^{20}$ =–34.5° (c 1, $CHCl_3$) IR ($CH_2Cl_2$): 2960, 2880, 1760, 1620, 1595, 1525, 1490, 1370, 1345, 1230, 1215, 1080, 1040, 860 $cm^{-1}$. $^1H$ NMR (200 MHz, $CDCl_3$): δ ppm: 2.08 and 2.09 (2s, 9H), 3.74 (s, 3H), 4.36 (broad d, 1H, J=8.7 Hz), 5.36 (m, 6H), 7.23 (d, 1H, J=9.1 Hz), 7.43 (d, 2H, J=8.3 Hz), 8.26 (m, 4H).

4) N-[2-(Methyl (2,3,4-tri-O-acetyl-β-D-glucopyranosyl) uronate)-5-nitrobenzyloxycarbonyl]daunorubicin (54a )

Preparation:

From 53 and daunorubicin (yield=62%).

Compound 54a: $C_{48}H_{50}O_{24}N_2$. M=1038. M.p.= 142°–145° C. $[\alpha]_D^{20}$=+115° (c 0.6, $CHCl_3$). IR ($CH_2Cl_2$): 2950, 1755, 1720, 1710, 1620, 1580, 1525, 1345, 1230, 1210, 1110, 1080, 1035 $cm^{-1}$. $^1H$ NMR (200 MHz, $CDCl_3$): δ ppm: 1.32 (d, 3H, J=7.3 Hz), 2.09 and 2.11 (2s, 9H), 2.43 (s, 3H), 2.93 and 3.24 (ABq, 2H, J=19 Hz), 3.59 (s, 3H), 4.30 (m, 2H), 4.51 (s, 1H), 4.96 and 5.11 (ABq, 2H, J=13 Hz), 5.20 and 5.60 (m, 6H), 7.14 (d, 1H, J=8.5 Hz), 7.41 (d, 1H, J=8 Hz), 7.79 (t, 1H, J=8 Hz), 8.05 (d, 1H, J=8 Hz), 8.21 (2H), 12.15 (s, 1H), 12.91 (s, 1H).

5) N-[2-(Methyl (β-D-glucopyranosulfonate)-5-nitrobenzyloxycarbonyl ]daunorubicin (54b)

From 54a with MeONa/MeOH (cf. preparation of 7 and 14, Examples 1 and 2). Red solid. $C_{42}H_{44}N_2O_{21}$. M=912. NMR ($CD_3COCD_3$): δ ppm: 2.37 (s, 3H), 3.70 (s, 3H), 4.04 (s, 3H), 6.50 (d, J=7.5 Hz, 1H), 7.32 (d, J=7.4 Hz, 1H), 7.60 (d, J=7.4 Hz, 1H), 7.89 (m, 2H), 8.19 (m, 2H), 13.30 (s, 1H), 14.15 (s, 1H).

6) N-[2-((β-D-Glucopyranosyl)uronic acid)-5-nitrobenzyloxycarbonyl ]daunorubicin (54c )

From 54b and BaO (cf. preparation of 22 in Example 3). Red solid. $C_{44}H_{42}N_2O_{21}$. M=898.

EXAMPLE 10

Synthesis of N-[2-((β-D-glucopyranosyl) uronic acid )-5-nitro-benzyloxycarbonyl ]doxorubicin (83c).

1) N-[2-(methyl (2,3,4-tri-O-acetyl-β-D-glucopyranosyl) uronate)-5-nitro-benzyloxy-carbonyl]doxorubicin (83a).

Preparation:

From 53 and doxorubicin (yield=65%).

Compound 83a: $C_{48}H_{50}N_2O_{25}$; M=1054 ; F=162°–167° C. (dec) ; $[\alpha]_D^{20}$122° (c 0 5 $CHCl_3$); IR ($CH_2Cl_2$): 1757, 1720, 1618, 1580, 1525, 1410, 1370, 1344, 1230 $cm^{-1}$; NMR (200 MHz, $CDCl_3$): δ ppm: 1.30 (d, 3H, J=7.3 Hz), 2.06 et 2.08 (28, 9H), 2.94 et 3.23 (ABq, 2H, J=19 Hz), 3.60 (s, 3H), 4.06 (s, 3H), 4.28 (d, 1H, J=9 Hz), 5.03 (ABq, 2H, J=13 Hz), 5.27–5.51 (m, 6H), 7.11 (d, 1H, J=8 Hz), 7.99 (d, 1H, J=8 Hz), 8.15 (m, 2H), 12.62 (s, 1H), 13.15 (s, 1H).

2) N-[2-(methyl (β-D-glucopyranosyl) uronate)-5-nitrobenzyloxycarbonyl]doxorubicin (83b).

Preparation:

From 83a with MeONa/MeOH (cf. preparation of 7 and 14, Examples 1 and 2).

Compound 83b: $C_{42}H_{44}N_2O_{22}$; M=928 ; F=180° C. (dec.); $[\alpha]_D^{20}$ 0° (c 0.5 $CHCl_3$); NMR (200 MHz, $CD_3COCD_3$): δ ppm: 1.29 (d, 3H, J=7,3 Hz), 3.79 (s, H), 4.07 (s, 3H), 6.09 (d, NH), 7.12 (d, 1H, J=8.6 Hz), 7.41 (d, 1H, J=8 Hz), 7.79 (t, 1H, J=8 Hz), 8.00 (d, 1H, J=8 Hz), 8.16 (m, 2H), 12.75 (s, 1H), 13.25 (s, 1H).

3) N-[2-((β-D-glucopyranosyl) uronic acid)-5-nitrobenzyloxycarbonyl]doxorubicin (83c).

Preparation:

From 83b with NaOH or pig liver esterase (EC 3.1.1.1.).

Compound 83c: red solid; $C_{41}H_{42}N_2O_{22}$; M=914.

EXAMPLE 11

1) 2-Chloro-4-methylphenyl 2,3,4,6-tetra-O-acetyl-α-D-galactopyranoside (55)

Preparation:

From 2,3,4,6-tetra-O-acetyl-α-D-galactopyranose and 2-chloro-4-methylphenol (cf. preparation of 1, yield=40%).

Compound 55: $C_{21}H_{25}O_{10}Cl$. M=472.5. $^1H$ NMR (270 MHz, $CDCl_3$): δ ppm: 2.02 (s, 3H), 2.06 (s, 3H), 2.14 (s, 3H), 2.20 (s, 3H), 2.32 (s, 3H), 4.12 (dd, 1H, J=12, J'=7 Hz), 4.17 (dd, 1H J=12 J'=6 Hz), 4.54 (ddd, 1H, J=7, J'=6, J''=1 Hz), 5.29 (dd, 1H, J=10, J'=4 Hz), 5.61 (m, 1H), 5.63 (dd, 1H, J=10, J'=4 Hz), 5.76 (d, 1H, J=4 Hz), 7.02 (dd, 1H, J=8, J'=2 Hz), 7.07 (d, 1H, J=8 Hz), 7.23 (d, 1H, J=2 Hz). MS ($DIC/NH_3$): m/z: 490 $(M+NH_4)^+$, 456, 331.

2) 2-Chloro-4-bromomethylphenyl 2,3,4,6-tetra-O-acetyl-α-D-galactopyranoside (56)

Preparation:

Monobromination of 55 with photochemical activation (cf. preparation of 2, yield=80%).

Compound 56: $C_{21}H_{24}O_{10}ClBr$. M=551.5. $^1H$ NMR (270 MHz, $CDCl_3$): δ ppm: 2.00 (s, 3H), 2.03 (s, 3H), 2.12 (s, 3H), 2.18 (s, 3H), 4.09 (dd, 1H, J=12, J'=7 Hz), 4.14 (dd, 1H, J=12, J'=6 Hz), 4.42 (s, 2H), 4.50 (ddd, 1H, J=7, J'=6, J''=1 Hz), 5.27 (dd, 1H, J=10, J'=4 Hz), 5.58 (m, 1H), 5 60 (dd, 1H, J=10, J'=4 Hz), 5.80 (d, 1H, J=4 Hz), 7.13 (d, 1H, J=8

Hz), 7.22 (dd, 1H, J=8, J'=2 Hz), 7.42 (d, 1H, J=2 Hz). MS (DIC/NH₃): m/z: 571 (M+NH₄)⁺, 569 (M+NH₄)⁺, 490, 331.

3)2-Chloro-4-hydroxymethylphenyl 2,3,4,6-tetra-O-acetyl-α-D-galactopyranoside (57)

Preparation:

From 56 (cf. preparation of 4, yield=34%).

compound 57: $C_{21}H_{25}O_{11}Cl$. M=488.5. ¹H NMR (270 MHz, CDCl₃): δ ppm: 1.98 (s, 3H), 2.04 (s, 3H), 2.10 (s, 3H), 2.18 (s, 3H), 4.09 (dd, 1H, J=12, J'=7 Hz), 4.14 (dd, 1H, J=12, J'=6 Hz), 4.49 (ddd, 1H, J=7, J'=6, J''=1Hz), 4.64 (s, 2H), 5.26 (dd, 1H, J=10, J'=4 Hz), 5 58 (m, 1H), 5 60 (dd, 1H, J=10, J'=4 Hz), 5.77 (d, 1H, J=4 Hz), 7.15 (d, 1H, J=8 Hz), 7.20 (dd, 1H, J=8, J'=2 Hz), 7.42 (d, 1H, J=2 Hz). MS (DIC/NH₃): m/z: 506 (M+NH₄)⁺, 472, 331.

4)2,5-Dioxopyrrolidin-1-yl 3-chloro-4-(2,3,4,6-tetra-O-acetyl-α-D-galactopyranosyl)benzyl carbonate (58)

Preparation:

From 57 and disuccinimidyl carbonate (DSC) (cf. preparation of 19, Example 3).

It should be noted that, because of its instability, the compound 58 could not be purified and isolated on a column of silica.

Compound 58: $C_{26}H_{28}ClNO_{15}$. M=629.5.

5)N-[3-Chloro-4-(2,3,4,6-tetra-O-acetyl-α-D-galactopyranosyl)benzyloxycarbonyl]daunorubicin (59)

Preparation:

Coupling of 58 with daunorubicin (cf. preparation of 6, yield=20%).

Compound 59: $C_{49}H_{52}ClNO_{22}$. M=1041.5. ¹H NMR (270 MHz, DMSO): δ ppm: 1.12 (d, 3H, J=7 Hz), 1.48 (m, 1H), 1.88 (m, 2H), 1.98 (s, 3H), 2.02 (s, 3H), 2.04 (s, 3H), 2.15 (s, 3H), 2.23 (m, 1H), 2.25 (s, 3H), 2.76 (m, 1H), 2.96 (m, 1H), 3.50–4.20 (m, 5H), 4.00 (s, 3H), 4.44 (m, 1H), 4.72 (m, 1H), 4.90 (m, 3H), 5.20 (m, 1H), 5.32 (m, 1H), 5.43 (m, 2H), 5.53 (s, 1H), 5.85 (d, 1H, J=4 Hz), 6.94 (m, 1H), 7.23 (m, 2H), 7.47 (d, 1H, J=2 Hz), 7.66 (m, 1H), 7.92 (m, 2H). MS (DIC/NH₃): m/z: 1060 (M+NH₄)⁺, 506, 331.

6)N-[3-Chloro-4-(α-D-galactopyranosyl)benzyloxycarbonyl]daunorubicin (60)

Preparation:

From 59 (cf. preparation of 7, yield=91%).

EXAMPLE 12

Synthesis of N-[3-nitro-4-((β-D-glucopyranosyl)uronic acid)benzyloxycarbonyl]daunorubicin (64c)

Methyl (4-formyl-2-nitrophenyl 2,3,4-tri-O-acetyl-β-D-glucopyranoside)uronate (61)

Preparation:

From a solution of methyl (2,3,4-tri-O-acetyl D-glucopyranosyl)uronate bromide (5.3 g), 3-nitro-p-hydroxybenzaldehyde (3.55 g) and silver oxide (15.45 g) under the conditions indicated for the preparation of 51. 5.35 g (80%) of pure 61 are obtained after flash chromatography and crystallization.

Compound 61: $C_{20}H_{21}NO_{13}$. M.p.=483. M.p.=172°–173° C. $[\alpha]_D^{20}$=+10° (c 1, CHCl₃) IR (lac): 1760, 1230 cm⁻¹. ¹H NMR (250 MHz, CDCl₃): δ ppm: 2.16 (s, 3H), 2.12 (s, 3H), 2.07 (s, 3H), 3.71 (s, 3H, OMe), 4.33 (d, 1H, J=8.2 Hz), 5.45–5.25 (m, 4H), 7.49 (d, 1H, J=7.5 Hz), 8 08 (dd, 1H, J=7.5, J'=1.8 Hz), 8.31 (dd, 1H, J=1.8 Hz), 9.97 (s, 1H). MS (DIC/NH₃): m/z: 501 (M+NH₄)⁺.

2) Methyl (4-hydroxymethyl-2-nitrophenyl 2,3,4-tri-O-acetyl-β-D-glucopyranoside)uronate (62)

Preparation:

From 61 by using NaBH₄/THF/MeOH (yield=72%).

Compound 62: $C_{20}H_{23}NO_{13}$. M=485. M.p.=173°–174° C. $[\alpha]_D^{20}$=+10° (c 1, CHCl₃) ¹H NMR: δ ppm: 2.08 (s, 6H), 2.01 (s, 3H), 3.63 (s, 3H), 4.12 (d, 1H, J=8 Hz), 4.62 (s, 2H), 5.35–5.02 (m, 4H), 7.21 (d, 1H, J=7 Hz), 7.39 (dd, 1H, J=7 Hz, J'=1.8 Hz), 7.65 (d, 1H, J=1.8 Hz). MS (DIC/NH₃): m/z: 503 (M+NH₄)⁺.

3)N-[3-Nitro-4-(methyl (2,3,4-tri-O-acetyl-β-D-glucopyranosyl)uronate)benzyloxycarbonyl]daunorubicin (64a)

Preparation:

The carbonate 63 is obtained as an intermediate from 62 and DSC; it is not purified but immediately reacted further with daunorubicin under the conditions described for the preparation of 54.

64a is isolated with a yield of 50%.

Compound 64a: $C_{48}H_{50}N_2O_{24}$. M=1038. M.p.= 137°–138° C. $[\alpha]_D^{20}$=+88° (c 0.5, chloroform). IR (CDCl₃): 1760, 1720, 1220 cm⁻¹. ¹H NMR: δ ppm: 1.30 (d, 3H, J=6 Hz), 1.75 (m, 2H), 2.12 (s, 3H), 2.10 (s, 3H), 2.13 (s, 3H), 2.45 (s, 3H), 3.00 (d, 1H, J=20 Hz), 3.30 (d, 1H, J=20 Hz), 3.75 (s, 3H), 4.14 (s, 3H), 4.26 (m, 2H), 4.47 (s, 1H), 5.08 (s, 2H), 5.10–5.47 (m, 4H), 5.58 (d, 1H), 7.50 (1H), 7.89 (1H), 8.05 (1H), 14.00 (s, 1H), 13.30 (s, 1H).

4)N-(4-Hydroxy-3-nitrobenzyloxycarbonyl)daunorubicin β-D-glucopyranoside (64b)

From 64a with MeOH/MeONa (cf. preparation of 7 and 14, Examples 1 and 2). Red solid. $C_{42}H_{44}N_2O_{21}$. M=912.

5)N-(4-Hydroxy-3-nitrobenzyloxycarbonyl)daunorubicin β-D-glucuronide (64c)

From 64b and BaO or K₂CO₃ (cf. preparation of 22 in Example 3). Red solid. $C_{41}H_{42}N_2O_{21}$. M=898.

EXAMPLE 13

Synthesis of N-[4-methoxy-5-nitro-2-((β-D-glucopyranosyl) uronic acid)benzyloxycarbonyl]daunorubicin (68c)

According to scheme XII, the Ag₂O -catalyzed glycosidation of 2-hydroxy-4-methoxy-5-nitrobenzaldehyde with methyl (peracetyl-β-D-glucopyranosyl)uronate bromide gives the compound 65, which is then converted to the derivative 68c by the method described in Example 9.

1) Methyl (2-formyl-5-methoxy-4-nitrophenyl 2,3,4-tri-O-acetyl-β-D-glucopyranoside)uronate (65)

This is obtained with a yield of 53% by the method used for 51 (see Example 9).

Compound 65: $C_{21}H_{23}NO_{14}$. M=513. M.p.=159° C. $[\alpha]_D$=83° (c 0.95, CHCl₃). IR (CHCl₃): 3080, 3010, 1765, 1695, 1620, 1580, 1540, 1450, 1375, 1300, 1220, 1080, 1045 cm⁻¹. ¹H NMR (200 MHz, CDCl₃): δ ppm: 2.08 (s, 6H), 2.10 (s, 3H), 3.74 (s, 3H), 4.04 (s, 3H), 4.39 (d, 1H, J=9 Hz), 5.39 (m, 4H), 6.92 (s, 1H), 8.43 (s, 1H), 10.16 (s, 1H).

2) Methyl (2-hydroxymethyl-5-methoxy-4-nitrophenyl 2,3, 4-tri-O-acetyl-β-D-glucopyranoside)uronate (66)

Preparation from 65 by using NaBH₄/THF/MeOH (yield=30%).

Compound 66: $C_{21}H_{25}NO_{14}$. M=514. M.p.=176° C. $[\alpha]_D$=-61° (c 1.05, CHCl₃). IR (CHCl₃): 3560, 3040, 2960, 1760, 1625, 1590, 1530, 1445, 1375, 1350, 1290, 1220, 1075, 1040 cm⁻¹. ¹H NMR (200 MHz, CDCl₃): δ ppm: 2.07 (s, 3H), 2.09 (s, 3H), 2.13 (s, 3H), 3.72 (s, 3H), 3.96 (s, 3H), 4.27 (1H), 4.50 and 4.63 (qAB, 2H, J=12.9 Hz), 5.23 (m, 4H), 6.99 (s, 1H), 7.99 (s, 1H).

3)4-Nitrophenyl 4-methoxy-5-nitro-2-(methyl (2,3,4-tri-O-acetyl-β-D-glucopyranosyl)uronate)benzyl carbonate (67)

Preparation from 66 and 4-nitrophenyl chloroformate (yield=74%).

Compound 67: $C_{28}H_{28}N_2O_{18}$. M=680. M.p.=90° C. $[\alpha]_D$=-47° (c 1.05, CHCl₃). IR (CHCl₃): 3020, 2960, 1745, 1615, 1575, 1435, 1340, 1280, 1205, 1068, 1030, 895, 852 cm⁻¹. ¹H NMR (200 MHz, CDCl₃): δ ppm: 2.06 (s, 3H), 2.07 (s, 3H), 2.09 (s, 3H), 3.75 (s, 3H), 3.98 (s, 3H), 4.35 (1H), 5.14 and 5.24 (qAB, 2H, J=12 Hz), 5.39 (m, 4H), 6.92 (s, 1H), 7.43 (d, 2H, J=9.1 Hz), 8.09 (s, 1H), 8.30 (d, 2H, J=9.1 Hz).

4)N-[4-Methoxy-5-nitro-2-(methyl (2,3,4-tri-O-acetyl-β-D-glucopyranosyl)uronate)benzyloxycarbonyl]daunorubicin (68a)

Preparation from 67 and daunorubicin (yield=83%).

Compound 68a: $C_{49}H_{52}N_2O_{25}$. M=1068. M.p.=153° C. (decomp.). $[\alpha]_D$=+105° (c 0.24, CHCl$_3$). $^1$H NMR (200 MHz, CDCl$_3$): δ ppm: 1.31 (d, 3H, J=7 Hz), 2.07 and 2.12 (2s, 9H), 2.42 (s, 3H), 2.91 and 3.24 (qAB, H, J=18.7 Hz), 3.62 (s, 3H), 3.94 (s, 3H), 4.08 (s, 3H), 4.93 (qAB, 2H), 6.88 (s, 1H), 7.39 (d, 1H, J=8 Hz), 7.77 (t, 1H, J=8 Hz), 7.94 (s, 1H), 8.03 (d, 1H, J=8 Hz), 9,59 (s, 1H), 10,29 (s, 1H).

5)N-[4-Methoxy-5-nitro-2-(methyl (β-D-glucopyranosyl)uronate) benzyloxycarbonyl]daunorubicin (68b)

Preparation from 68a (yield=91%) by using MeONa/MeOH (−20° C., 12 hours).

Compound 68b: $C_{43}H_{46}N_2O_{22}$. M=942. M.p.=176°–177° C. $[\alpha]_D$=+1° (c 0.19, CHCl$_3$). IR (CHCl$_3$): 3000, 1750, 1720, 1710, 1620, 1580, 1520, 1440, 1410, 1365, 1345, 1280 cm$^{-1}$. $^1$H NMR (200 MHz, CD$_3$OD): δ ppm: 2.43 (S, 3H), 3.10 (qAB, 2H), 3.79 (s, 3H), 3.95 (s, 3H), 4.08 (s, 3H), 6.28 (d, 1H), 6.87 (s, 1H), 7.46 (d, 1H, J=8 Hz), 7.83 (d, 1H, J=8 Hz), 8.02 (m, 2H). SM (FAB$^+$)m/z:109

6)  N-[4-Methoxy-5-nitro-2-((β-D-glucopyranosyl)uronic acid)benzyloxycarbonyl]daunorubicin (68c)

Preparation from 68b by using Na$_2$CO$_3$/MeOH/H$_2$O.
Compound 68c: Red solid. $C_{42}H_{44}N_2O_{22}$. M=928.

EXAMPLE 14

Synthesis of N-[2-((β-D-glucopyranosyl) uronic acid)-5-chloro-benzyloxycarbonyl]daunorubicin (82c).

1) Methyl (2-formyl-4-chlorophenyl 2,3,4-tri-O-acetyl -β-D-glucopyranoside)uronate (79).

This is obtained (yield=41% ) by the method indicated for 51 (see Example 9).

Compound 79 : $C_{20}H_{21}ClO_{11}$; M=472.5; F=156°–157° C.; $[\alpha]_D^{20}$ −39° (c 1, CHCl$_3$); IR (CH$_2$Cl$_2$: 2940, 2870, 1755, 1680, 1585, 1465 cm$^{-1}$; NMR (200 MHz, CDCl$_3$) : δ ppm: 2.09 (s, 9H), 3.74 (s, 3H), 4.25 (d, 1H, J=8.5 Hz), 5.30 (m, 4H), 7.10 (d, 1H, J=8.5 Hz), 7.53 (dd, 1H, J=8.5 et 2.5 Hz), 7.80 (d, 1H, J=2.5 Hz), 10.27 (s, 1H).

2) Methyl (2-hydroxymethyl-4-chloro phenyl 2,3,4-tri-O-acetyl-β-D-glucopyranoside) uronate (80).

This is obtained from 79, by using NaBH$_4$/THF/MeOH (yield=70%).

Compound 80: $C_{20}H_{23}ClO_{11}$; M=474.5; F=120° C.; $[\alpha]_D^{20}$−20° (c 0.9, CHCl$_3$); IR (CH$_2$Cl$_2$): 3050, 2980, 1750, 1470, 1415, 1250, 1220 cm$^{-1}$; NMR (200 MHz, CDCl$_3$): δ ppm: 2.06 (s, 3H), 2.07 (s, 3H), 2.11 (s, 3H), 3.71 (s, 3H), 4.14 (d, 1H, J=9 Hz), 4.3 et 4.72 (ABq, 2H, J=13 Hz), 5.11 (d, 1H, J=6.5 Hz), 5.34 (m, 3H), 6.94 (d, 1H, J=8.7 Hz), 7.23 (dd, 1H, J=8.7 et 2.5 Hz), 7.36 (d, 1H, J=2.5 Hz).

3) 4-chlorophenyl 2-(methyl (2,3,4-tri-O-acetyl-β-D-glucopyranosyl) uronate)-5-nitrobenzyl carbonate (81).
Preparation:
From 80 and 4-nitrophenyl chloroformate (yield =50%).
Compound 81: $C_{27}H_{26}ClNO_{14}$; M=623.5; F=136° C.; NMR (200 MHz, CDCl$_3$) :δ ppm: 2.08 (s, 9H), 3.74 (s, 3H), 4.22 (d large, 1H, J=8.7 Hz), 5.30 (m, 6H), 7.03 (d, 1H, J=8.2 Hz), 7.30 (m, 4H), 8.30 (d, 2H, J=8.3 Hz).

4)  N-[2-(methyl(2,3,4-tri-O-acetyl-β-D-glucopyranosyl) uronate)-5-chloro-benzyloxycarbonyl]daunorubicin (82a).

Preparation:
From 81 and daunorubicin (yield=73%).
Compound 81: $C_{48}H_{50}ClNO_{22}$; M=1027.5; F=155° C. (dec.); $[\alpha]_D^{20}$ 125° (c 0.24, CHCl$_3$); IR (CH$_2$Cl$_2$): 1755, 1715, 1610, 1575 cm$^{-1}$; NMR (200 MHz, CDCl$_3$): δ ppm : 1.31 (d, 3H, J=7 Hz), 2.05 (s, 6H), 2.08 (s, 3H), 2.42 (s, 3H), 2.94 et 3.25 (ABq, 2H, J=19 Hz), 3.62 (s, 3H), 4.06 (s, 3H), 4.20 (m, 2H), 4.53 (broad s, 1H), 4.96 (broad s, 2H), 5.15–5.52 (m, 6H), 7.00 (d, 1H, J=8 Hz), 7.20 (m, 2H), 7.40 (d, 1H, J=8 Hz), 7.79 (t, 1H, J=8 Hz), 8.05 (d, 1H, J=8Hz).

5)  N-[2-(methyl (β-D-glucopyranosyl)uronate)-5-chloro-benzyloxycarbonyl]daunorubicin (82b).
Preparation:
From 82a by using MeONa/MeOH (cf. preparation of 7 and 14, Examples 1 and 2), yield=47%.
Compound 82b : red solid; $C_{42}H_{44}ClNO_{19}$; M=901.5; F=167°–170° C.; $[\alpha]_D^{20}$0° (c 0.03, MeOH); NMR (200 MHz, CDCl$_3$) δ ppm: 2.42 (s, 3H), 2.96 et 3.23 (ABq, 2H, J=18 Hz), 3.79 (s, 3H), 4.07 (s, 3H), 5.89 (d, NH), 6.99 (broad d, 1H, J=8 Hz), 7.20 (broad d, 1H, J=8 Hz), 7.33 (s, 1H), 7.41 (d, 1H, J=8 Hz), 7.80 (t, 1H, J=8 Hz), 8.03 (d, 1H, J=8 Hz).

6)N-[2-((β-D-glucopyranosyl)uronic acid)-5-chlorobenzyloxycarbonyl ]daunorubicin (82c ).
Preparation:
From 82b by using Na$_2$CO$_3$ (cf. preparation of 22, Example 3).
Compound 82c : red solid; $C_{41}H_{42}ClNO_{19}$; M=887.5.

EXAMPLE 15

Synthesis of N-[4-hydroxy-3-nitro-benzyloxycarbonyl) doxorubicin β-D-glucuronide (70c).

1) 4-nitro-phenyl 4-(methyl (2,3,4-tri-O-acetyl-β-glucopyranosyl) uronate)-5-nitro-benzyl carbonate (69).
Preparation:
From 62 and paranitrophenyl chloroformate (yield=47%).
Compound 69 : $C_{27}H_{26}N_2O_{17}$; M=650; F=126° C.; $[\alpha]_D^{20}$=+12° (c 0.1, CHCl13), IR (KBr)$_{vmax}$ 1730 (CO, ester), 1210; $^1$H NMR (90 MHz, CDCl$_3$) : δ ppm : 7.81 (d, 1H, J=5 Hz), 7.54 (dd, 1H, J=8.4 Hz), 7.30 (d, 1H, J=8.4 Hz), 5.36–5.29 (m, 3H), 5.18 (d, 1H, J=6.7 Hz), 4.72 (s, 2H), 4.20 (d, 1H, J=8.4 Hz), 3.74 (s, 3H), 2.12 (s, 3H), 2.06 (s, 3H), 2.05 (s, 3H). SM (DCI/NH$_3$) m/z: 668 (M+18)$^+$, 608, 503, 443.

2) N-[3-nitro-4-(methyl (2,3,4-tri-O-acetyl-β-D-glucopyranosyl) uronate)-benzyloxycarbonyl]doxorubicin (70a ).
Preparation:
From 69 and doxorubicin (yield=6%).
Compound 70a : $C_{48}H_{50}O_{25}N_2$, M=1.054; F=114° C. $[\alpha]_D^{20}$=+121° (c 0.05, CHCl$_3$). IR (KBr)$_{vmax}$ 1760, 1730, 1220. $^1$H NMR (250 MHz, CDCl$_3$): δ ppm: 13.90 (s, 1H, OH phenol), 13.15 (s, 1H, OH phenol), 8.00–7.20 (m, 6H arom.), 5.47 (s, 1H), 5.29–5.16 (m, 5H), 4.97 (s, 2H), 4.73 (s, 2H), 4.20–4.15 (m, 2H), 4.21 (s, 3H), 3.80 (br s, 1H), 3.72 (s, 3H), 3.68 (s, 1H), 3.19 (d, 1H, J=19 Hz) et 2.91 (d, 1H, J=19 Hz), 2.30 (d, 1H, J=13.6 Hz), 2.15 (s, 3H), 2.10 (d, 1H, J=13.6 Hz), 2.07 (s, 6H), 1.83 (br s, 2H), 1.27 (d, 1H, J=5.4 Hz).

3) N-[3-nitro-4-(methyl (β-D-glucopyranosyl) uronate) benzyloxycarbonyl]doxorubicin (70b).
Preparation:
The compound 70a (1.48 g) is dissolved in anhydrous DMF (20 mL). 200 mL of anhydrous MeOH is then added. After cooling at 0° C., 18 mL of 1M MeONa are added. After stirring for 1 h at 0° C., the medium is then neutralized by addition of a methanol solution of AcOH (10%) at 0° C. After evaporation to dryness and flash chromatography (solvent $CH_2Cl_2$/MeOH 90:10), 500 mg of pure 70b are isolated.

Compound 70b : $C_{42}H_{44}O_{22}N_2$; M=928; F=150° C.; $[\alpha]_D^{20}$=+85° (c 0.05, THF) ; $^1$H NMR (250 MHz, $CDCl_3$) : δ ppm: 13.92 (s, 1H), 13.22 (s, 1H), 7.92–7.18 (m, 6H), 5.23 (s, 1H), 5.07 (m, 2H), 4.95 (s, 2H), 3.88 (s, 1H), 4.57 (s, 2H), 4.07 (m, 2H), 3.96 (s, 3H), 3.64 (s, 3H), 3.01 (d, 1H) and 2.85 (d, 1H, J=18 Hz) (AB syst), 2.22 (d, 1H, J=13.6 Hz), 2.03 (dd, 1H, J=13.6, J'=5 Hz), 1.92–1.37 (m, 4H), 1.15 (d, 1H, J=6.8 Hz). SM (FAB) m/e: 951 (M+23).

4) N-[4-hydroxy-3-nitro-benzyloxy-carbonyl) doxorubicin β-D-glucuronide (70c ).

Preparation:

The compound 70b (780 mg) is dissolved in THF (75 mL); then water (≈30 mL) and 2N NaOH (drop by drop) (750 μL) are added after cooling at 0° C. After stirring at 0° C. for 1 h 30, the medium is neutralized by addition of IR 50H$^+$resin. The filtrate is then evaporated to give about 35 mL, and lyophilized. 750 mg of pure 70c are obtained.

Compound 70c : $C_{41}H_{41}O_{22}N_2$; M =914; F=210° C. ; $[\alpha]_D^{20}$ =–78° (c 0.05, $H_2O$). $^1$H NMR (250 MHz, DMSO) : δ ppm: 14.00 (br s, 2H), 8.00–6.90 (m, 6H), 5.48 (s, 1H), 5.23 (s, 1H), 5.07 (d, J=6.4 Hz), 4.98 (m, 2H), 4.59 (s, 2H), 3.99 (s, 3H), 3.30–3.10 (m, 2H), 2.96 (d, 1H, J=14 Hz), 2.91 (d, 1H, J=14 Hz), 2.20 (d, 1H, J=11.5 Hz), 2.13 (d, 1H, J=11.5 Hz), 1.87 (d, 1H, J=13 Hz), 1.48 (d, 1H, J=13 Hz), 1.13 (d, 3H, J=6.4 Hz).

EXAMPLE 16

Synthesis of N-4-hydroxy-3-nitro(benzyloxycarbonyl) daunorubicin α-D-galactopyranoside (75b).

1) 4-methylphenyl 2,3,4,6-tetra-O-acetyl-α-D-galactopyranoside (71).

According to scheme XIV, the coupling of penta-O-acetyl-D-galactopyranose (36 g, 92 mmoles) with p-cresol (30 g, 280 mmoles) is carried out by fusion in the presence of anhydrous $ZnCl_2$ (1.8 g) at 160° C. for 30 minutes, according Helferich technique. After cooling, a chromatography on a column of 60H silica (solvent:hexane-ethyl acetate: 90/10-v/v) is directly performed on the mixture and gives 15 g, yield=40% of 4-methylphenyl 2,3,4,6-tetra-O-acetyl-α-D-galactopyranoside, which crystallises in ethanol. Its analytical characteristics are identical as the one described before.

2) 4-bromomethylphenyl 2,3,4,6-tetra-O-acetyl-α-D-galactopyranoside (72).

Preparation:

1.4 g (3.2 mmoles) of 4-methylphenyl 2,3,4,6-tetra-O-acetyl-α-D-galactopyranoside (71) and 0.46 g (1.6 mmole) of 1,3-dibromo 5,5-dimethylhydantoine are added in 100 ml of carbone tetrachloride, and the mixture est refluxed under irradiation with light (1 000 W) for 15 minutes. After cooling, the reaction medium is filtered and the filtrate is then evaporated to dryness. 3.5 g of 4-bromomethylphenyl 2,3,4,6-tetra-O-acetyl-α-D-galactopyranoside (72) are isolated by crystallization from methanol (yield=76%).

Compound 72: $C_{21}H_{25}O_{10}Br$, M=517; F=105° C. (MeOH); $[\alpha]_D^{20}$=+168° (c 1, $CHCl_3$) ; IR (KBr) cm$^{-1}$: 1747 (vC=O ester), 1222 (ωCH$_2$Br) ; $^1$H NMR (270 MHz, $CDCl_3$) δ ppm: 1.97 (s, 3H), 2.08 (s, 3H), 2.10 (s, 3H), 2.21 (s, 3H), 4.05 (dd, J=11 et 7 Hz, 1H), 4.13 (dd, J=11 et 6 Hz, 1H), 4.18 (t, J=7 Hz, 1H), 4.52 (s, 2H), 5.28 (dd, J=11 et 4 Hz, 1H), 5.52 (d, J=3 Hz, 1H), 5.58 (dd, J=11 et 3 Hz, 1H), 5.79 (d, J=4 Hz, 1H), 7.04 (d, J=9 Hz, 2H), 7.35 (d, J=9 Hz, 2H). SM (DIC/NH$_3$) m/z: 534/536 (M+NH$_4$)$^+$.

3) (4-bromomethyl 2-nitro)-phenyl 2,3,4,6-tetra-O-acetyl-α-D-galactopyranoside (73).

Preparation:

5 ml of nitric acid are added dropwise to a solution of 4-bromomethylphenyl 2,3,4,6-tetra-O-acetyl-α-D-galactopyranoside (72) (1.5 g, 2.9 mmoles ) in acetic anhydride (10 ml), in 2 hours, at 20° C. After stirring for one hour, the medium is neutralized by a sodium hydrogenocarbonate solution. After conventional extraction, 1.12 g of (4-bromomethyl 2-nitro)-phenyl 2,3,4,6-tetra-O-acetyl-α-D-galactopyranoside (73) are isolated by chromatography on silica gel 60H (yield=69%).

Compound 73: $C_{21}H_{24}NO_{12}Br$; M=562; F=168° C. (MeOH); $[\alpha]_D^{20}$=+165° (c 1 01 $CHCl_3$) IR (KBr) cm$^{-1}$:1747 (vC=O ester), 1534 (vAsN=O), 1222 (vCH$_2$Br), $^1$H NMR (270 MHz, $CDCl_3$) δ ppm: 1.84 (s, 3H), 1.88 (s, 3H), 2.08 (s, 3H), 2.15 (s, 3H), 4.11 (d, J=7 Hz, 2H), 4.39 (t, J=7 Hz, 1H), 4.47 (s, 2H), 5.24 (dd, J=11 et 4 Hz, 1H), 5.48 (dd, J=11 et 3 Hz, 1H), 5.57 (d, J=3 Hz, 1H), 5.89 (d, J=4 Hz, 1H), 7.32 (d, J=9 Hz, 1H), 7.56 (dd, J=9 et 2 Hz, 1H), 7.84 (d, J=2 Hz, 1H). SM (DIC/NH$_3$) m/z: 579/581 (M+NH$_4$)$^+$.

4) (4-hydroxymethyl 2-nitro )-phenyl 2,3,4,6-tetra-O-acetyl-α-D-galactopyranoside (74).

Preparation:

A solution of the (4-bromomethyl 2-nitro)phenyl 2,3,4,6-tetra-O-acetyl-α-D-galactopyranoside (73) (0.3 g, 0.5 mmole) in 15 ml of acetone is stirred overnight at 20° C., in the presence of 15 ml of a 0.1N aqueous solution of AgNO$_3$. After filtration and acetone evaporation, the (4-hydroxymethyl 2-nitro)-phenyl 2,3,4,6-tetra-O-acetyl-α-D-galactopyranoside (74) precipitates in water. Said obtained product is then dried (0.25 g, yield=93%).

Compound 74: $C_{21}H_{25}NO_{13}$; M=499; F=170° C. (MeOH); $[\alpha]_D^{20}$ =+174° (c 1.02, $CHCl_3$) ; IR (KBr) cm$^{-1}$: 3500 (vOH), 1746 (vC=O ester), 1234 (vC—OH) ; $^1$H NMR (270 MHz, $CDCl_3$) δ ppm: 2.00 (s, 3H), 2.02 (s, 3H), 2.11 (s, 3H), 2.18 (s, 3H), 4.13 (d, J=6 Hz, 2H), 4.43 (t, J=6 Hz, 1H), 4.73 (d, J=5 Hz, 2H), 5.27 (dd, J=11 et 4 Hz, 1H), 5.50 (dd, J=11 et 3 Hz, 1H), 5.59 (d, J=3 Hz, 1H), 5.88 (d, J=4 Hz, 1H), 7.32 (d, J=9 Hz, 1H), 7.53 (dd, J=9 et 2 Hz, 1H), 7.84 (d, J=2 Hz, 1H). SM (DIC/NH$_3$) m/z: 517 (M+NH$_4$)$^+$.

5) N-4-hydroxy-3-nitro-(benzyloxycarbonyl) 2,3,4,6-tetra-O-acetyl-α-D-galactopyranoside daunorubicin (75a).

Preparation:

A solution of 74 (0.05 g–0.1 mmole) and triethylamine (28 μl, 0.2 mmole) in anhydrous dichloromethane (5 ml) is added, at 20° C., dropwise under argon to a solution of disuccinimido-carbonate (0.05 g–0.2 mmole) in 2 ml of acetonitrile. After stirring for 90 minutes, the medium is filtered and the filtrate is evaporated to dryness. The succinimidocarbonate is obtained in the form of a precipitate.

A solution of daunorubicin (0.03 g–0.06 mmole) and triethylamine (50 μl, 0.35 mmole) in 3 ml of dimethylformamide are added at 20° C., under argon, to a solution of the crude succinimidocarbonate previously prepared. After a reaction of 15 minutes and evaporation of the solvent, the N-[4-hydroxy-3-nitro-(2,3,4,6-tetra-O-acetyl-α-D-galactopyranoside) (benzyloxycarbonyl)]-daunorubicin is purified on silica gel chromatography 60H (solvent:cyclohexane-acetone: 50/50-v/v) and then washed in water (45.2 mg, yield=43% ).

Compound 75a: $C_{49}H_{52}N_2O_{24}$; M=1052; amorphous; $[\alpha]_D^{20}$ =+217° (c 0.10, $CHCl_3$) ; $^1$H NMR (270 MHz, $CDCl_3$) δ ppm: 1.28 (d, J=7 Hz, 3H), 1.97 (s, 3H), 2.02 (s, 3H), 2.09 (s, 3H), 2.16 (s, 3H), 2.41 (s, 3H), 2.69 (s, 1H ech/D$_2$O), 2.88 (d, J=12 Hz, 1H), 2.93 (d, J=19 Hz, 1H), 3.24 (d, J=12 Hz, 1H), 3.24 (d, H=19 Hz, 1H), 3.69 (broad s, 1H), 3.78 (m, 1H ech/D$_2$O), 4.09 (s, 3H), 4.13 (d, J=6 Hz, 2H), 4.23 (d, J=7 Hz, 1H), 4.39 (t, J=6 Hz, 1H), 4.72 (s, 1H ech/D$_2$O), 5.01 (s, 2H), 5.24 (dd, J=10 et 4 Hz, 1H), 5.27 (m, 2H), 5.48 (dd, J=10 et 3 Hz, 1H), 5.50 (m, 1H), 5.58 (d, J=3 Hz, 1H), 5.87 (d, J=4 Hz, 1H), 7.29 (d, J=8 Hz, 1H), 7.40 (d, J=8 Hz, 1H), 7.48 (dd, J=8 et 2 Hz, 1H), 7.76 (d, J=2 Hz, 1H), 7.79 (t, J=8 Hz, 1H), 8.02 (d, J=8 Hz, 1H). SM (DIC/NH$_3$) m/z: 813 (M−239)$^+$, 672 (M−380)$^+$.

6) N-4-hydroxy-3-nitro-(benzyloxycarbonyl)-daunorubicin α-D-galactopyranoside (75b).

Preparation:

A solution of N-4-hydroxy-3-nitro-2,3,4,6-tetra-O-acetyl-α-D-galactopyranoside (benzyloxycarbonyl) daunorubicin (17 mg, 0.016 mmole) in 2 ml of 0.1N sodium methanolate is stirred and kept at 0° C. for 30 minutes. The medium is neutralized by the addition of Amberlite IRC 120 H$^+$ resin and then filtered. The filtrate is evaporated to dryness to give 14 mg of N-4-hydroxy-3-nitro-(benzyloxycarbonyl)daunorubicin α-D-galactopyranoside (yield=98%).

Compound 75b : C$_{41}$H$_{44}$N$_2$O$_{20}$; M=884; amorphous; $[\alpha]_D^{20}$ =+246° (c 0.10, EtOH); $^1$H NMR (270 MHz, CDCl$_3$) δ ppm: 1.22 (d, J=7 Hz, 3H), 1.95 (m, 2H), 2.28 (m, 1H), 2.38 (m, 1H), 2.41 (s, 3H), 2.81 (d, J=19 Hz, 1H), 3.01 (d, J=19 Hz, 1H), 4.04 (s, 3H), 5.38 (m, 1H), 5.82 (m, 1H), 7.50–7.70 (m, 4H), 7.90 (m, 2H). SM (FAB, template: thioglycerol) m/z: 885 (M+H)$^+$.

EXAMPLE 17

Synthesis of N-[4-hydroxy-3-chloro(benzyloxycarbonyl)]-doxorubicin β-D-glucuronide (78b).

1) 4-hydroxy-3-chlorobenzaldehyde 2,3,4-tri-O-acetyl-β-D-methylglucuronide (76).

Preparation:

10 g of silver oxide are added to a solution of 2 g (12.8 mmoles) of 4-hydroxy-3-chlorobenzaldehyde and 3.4 g (8.5 mmoles) of 2,3,4-tri-O-acetyl-(α-D-methylglucuronide bromide in anhydrous acetonitrile (150 ml). The reaction medium is stirred for 4 hours at 20° C. and filtered on celite and the filtrate is evaporated to dryness. The dry residue obtained is then purified by a silica gel 60H chromatography (solvent:cyclohexaneacetone; 80/20 v/v). The 4-hydroxy-3-chlorobenzaldehyde 2,3,4-tri-O-acetyl-β-D-methylglucuronide (76) is thus obtained (1.6 g; yield=40%).

Compound 76: C$_{20}$H$_{21}$ClO$_{11}$; M=475; F=125° C.; $[\alpha]_D^{20}$ =−57° (c 0.5, CHCl$_3$); IR (KBr) ν cm$^{-1}$: 3030, 2975, 2875, 1760, 1680, 1595, 1375, 1235, 1040; $^1$H NMR (270 MHz, CDCl$_3$) δ ppm: 2.09 (3H, s), 2.11 (3H, s), 2.20 (3H, s), 3.73 (3H, s), 4.28 (1H, d, J=9 Hz), 5.25 (1H, d, J=7 Hz), 5.32–5.42 (3H, m), 7.30 (1H, d, J=8 Hz), 7.77 (1H, dd, J=8 et 2 Hz), 7.93 (1H, d, J=2 Hz), 9.90 (1H, s). SM (DIC/NH$_3$) m/z: 490/492 (M+NH$_4$)$^+$352, 317.

2) (4-hydroxy-methyl -2-chloro)-phenyl 2,3,4-tri-O-acetyl -β-D-methylglucuronide (77).

Preparation:

Silica (3 g) and sodium borohydride (0.3 g, 7.8 mmoles) are added at 0° C. to a solution of 76 (1.56 g; 3.3 mmoles) in a mixture of chloroforme (35 ml) and isopropanol (7.5 ml). The medium is stirred for 2 hours at room temperature. After filtration, the medium is diluted with CH$_2$Cl$_2$ (30 ml), then washed with water (3×30 ml), dried on Na$_2$SO$_4$ and evaporated to give 1.00 g of (4-hydroxymethyl-2-chloro)-phenyl 2,3,4-tri-O-acetyl-β-D-methylglucuronide (yield= 64%).

Compound 77: C$_{20}$H$_{23}$ClO$_{11}$; M=474.5; F=138°–140° C.; $[\alpha]_D^{20}$ =−95° (c 0.1 CHCl$_3$); IR (KBr) νcm$^{-1}$:3510, 2955, 1765, 1740, 1500, 1375, 1235, 1100, 1050, 900, 820, 775; $^1$H NMR (270 MHz, CDCl$_3$) δ ppm: 2.06 (3H, s), 2.09 (3H, s), 2.12 (3H, s), 3.74 (3H, s), 4.15 (1H, d, J=8 Hz), 4.63 (2H, s), 5.04 (1H, d, J=7 Hz), 5.35 (3H, m), 7.20 (2H, m), 7.38 (1H, d, J=1.5 Hz). SM (DIC/NH$_3$) m/z: 492/494 (M+NH$_4$)$^+$, 317.

3) N-(4-hydroxy-3-chloro 2,3,4-tri-O-acetyl-β-D-methyl glucuronide benzyloxycarbonyl)-doxorubicin (78a).

Preparation:

A solution of 77 (1.00 g; 2 mmoles) and triethylamine (300 μl ; 2.1 mmoles) in anhydrous dichloromethane (80 ml) is added dropwise, at 20° C., under argon, to a solution of disuccinimidocarbonate (1.08 g; 4.2 mmoles) in 50 ml of acetonitrile. After stirring for 90 minutes, the medium is filtered and the filtrate is evaporated to dryness to give the succinimidocarbonate (1.3 g), used without purification for the condensation with doxorubicin.

A solution of doxorubicin (0.882 g; 1.6 mmoles) and triethylamine (230 μl ; 1.6 mmoles) in 40 ml of dimethylformamide are added at 20° C., under argon, to a solution of the crude succinimidocarbonate previously prepared. After a reaction of 2 hours, the solvent is evaporated under reduced pressure. The obtained residue gives, after silica gel 60H chromatography (solvent:dichloromethane-methanol, 95/5 v/v), the N-(4-hydroxy-3-chloro-2,3,4-tri-O-acetyl-β-D-methylglucuronide benzyloxycarbonyl)-doxorubicin (78a) is obtained (0.691 g; yield=41%).

Compound 78a : C$_{48}$H$_{50}$ClNO$_{23}$; M=1043.5; amorphous; $[\alpha]_D^{20}$ =+260° (c 0.01, CH$_3$OH) ; IR (KBR) ν cm$^{-1}$:3430, 2960, 2950, 1725, 1580, 1460, 1380, 1290, 1235, 1125, 1070, 1040, 755. $^1$H NMR (270 MHz, CDCl$_3$) δ ppm: 1.30 (3H, d, J=6.5 Hz), 1.85 (2H, m), 2.02 (3H, s), 2.05 (3H, s), 2.09 (3H, s), 2.17 (1H, dd, J=15 et 3.5 Hz), 2.35 (1H, dd, J=15 et 1 Hz), 2.97 (1H, d, J=19 Hz), 3.27 (1H, d, J=19 Hz), 3.67 (1H, m), 3.77 (3H, s), 3.86 (1H, m), 4.08 (3H, s), 4.15 (2H, m), 4.75 (2H, s), 4.97 (2H, s), 5.02 (1H, d, J=7 Hz), 5.18 (3H, m), 5.50 (1H, dd, J=3.5 et 1 Hz), 7.18 (2H, m), 7.30 (1H, d, J=1 Hz), 7.38 (1H, d, J=8 Hz), 7.79 (1H, t, J=8 Hz), 8.03 (1H, d, J=8 Hz), 13.15 (1H, s, ech. D$_2$O), 13.85 (1H, s, ech. D$_2$O).

4) N-(4-hydroxy-3-chloro-benzyloxy-carbonyl)-doxorubicin β-D-glucuronide (78b).

Preparation:

A solution of 78a (0. 280 g; 0.27 mmoles ) in 60 ml of 0.05N sodium methanolate is stirred and kept at 0° C. for 45 minutes. The medium is neutralized by the addition of Amberlite IRC 120 H$^+$ resin and then filtered. The filtrate is evaporated to dryness to give 240 mg of N-(4-hydroxy-3-chloro-benzyloxycarbonyl)-doxorubicin β-D-methylglucuronide. Said compound is used without purification for the deprotection of carboxyl group.

The crude N-(4-hydroxy-3-chlorobenzyloxycarbonyl)-doxorubicin β-D-methylglucuronide previously prepared is dissolved in a phosphate buffer solution (48 ml) (pH=8), containing 1.2 ml of pig liver esterase (Sigma, ref. E-3128) and 24 ml of acetone. Said solution is kept 4 hours at 37° C. After evaporation to dryness, the residue is purified by a silica gel 60H chromatography (solvent:acetonitrile-water; 95/5 v/v). The compound 78b is obtained (0.049 g; yield= 20%).

Compound 78b: C$_{41}$H$_{42}$ClNO$_{20}$; M=903.5; amorphous; $[\alpha]_D^{20}$=+140° (c 0.01, CH$_3$OH); IR (KBr) ν cm$^{-1}$ : 3400, 2950, 1580, 1510, 1470, 1415, 1240, 1215, 1100, 830, 760; $^1$H NMR (300 MHz, DMSO-d$_6$) δ ppm: 1.11 (3H, d, J=6.5 Hz), 1.90 (2H, m), 2.15 (2H, m), 3.98 (3H, s), 4.54 (2H, s), 4.87 (2H, s), 4.94 (1H, d, J=Hz), 5.20 (1H, dd, J=3.5 et 1 Hz), 7.18 (2H, m), 7.36 (1H, d, J=1 Hz), 7.70 (2H, m), 7.94 (1H, d, J=8 Hz). SM (FAB, template:nitrobenzyl alcohol) m/z: 904/906 (M+H)$^+$.

PHARMACOLOGICAL REPORT ON PRODRUGS ACCORDING TO THE INVENTION

PHARMACOLOGICAL TEST:

Example A:

The biological and biochemical tests consisted in:

evaluating the cytotoxicity of the glycosylated prodrug, studying the cleavability of the glycoside by the corresponding enzyme, and determining in vitro the kinetics of disappearance of the glycoside and the formation of the two products (anthracycline+self-sacrificing arm and anthracycline) resulting initially from the scission of the sugar on the glycosylated phenol and then from the scission of the self-sacrificing arm (FIGS. 1, 2, 3 and 4).

Figure 3:
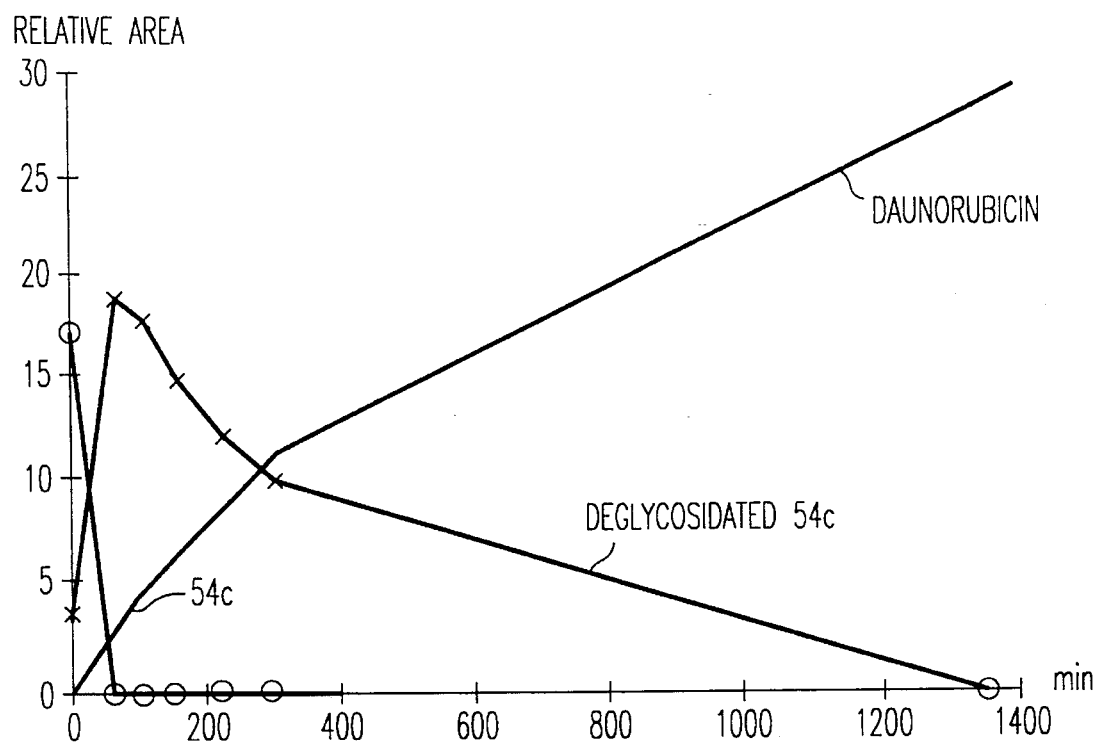
FIG. 3 shows the half-life when derivative 54c is incubated with concentrated recombinant human β-glucuronidase.
Figure 4:
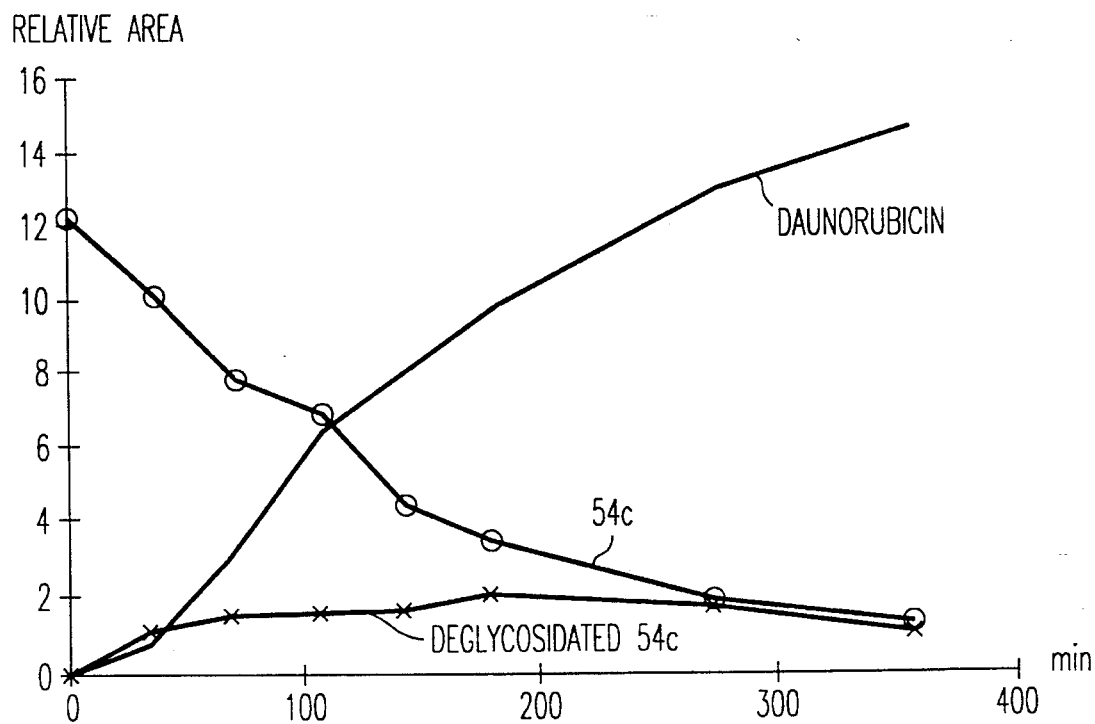
FIG. 4 shows the half-life when derivative 54c is incubated with β-glucuronidase diluted to 1/100 (other concentrations identical to those of FIG. 3).
Figure 5:
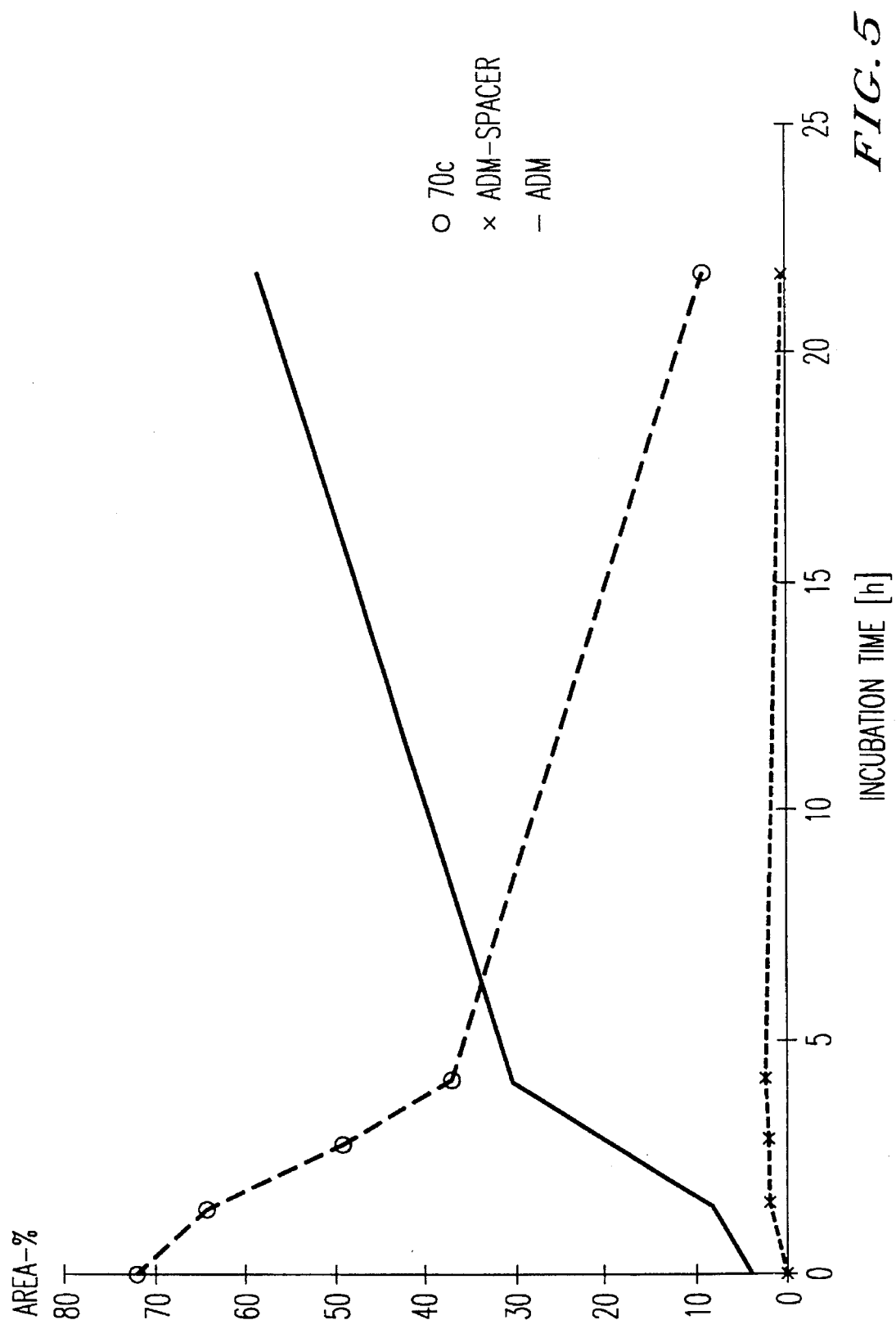
FIG. 5 shows the half-life when derivative 70c is incubated with human β-glucuronidase.

I. Half-life:

FIGS. 1, 2, 3, 4 and 5 illustrate the results obtained with the derivatives 48b (FIG. 1), 60 (FIG. 2), 54c (FIGS. 3 and 4) and 70c (FIG. 5). These figures show the time on the abscissa and the relative area on the ordinate and make it possible to evaluate the concentrations of prodrug and anthracycline as a function of time. It should be noted that the rate of appearance of the daunorubicin varies according to the type of self-sacrificing arm.

Results obtained with the derivative 48b:

This derivative is incubated with α-galactosidase (originating from human placenta) and 0.075M N-acetylgalactosamine at 37° C. and pH 5 (0.02M phosphate buffer). The results are determined by HPLC (daunorubicin: $t_r$=8.5 min; 48b: $t_r$=11.5 min; deglycosidated 48b: $t_r$=16.7 min). 48b is hydrolyzed with a half-life of 1 h.

At pH 5 the compound DNM/self-sacrificing arm (deglycosidated product) disappears with a half-life of 45 h; the half-life is less than 16 h for the same product at pH 7.3 and daunomycin appears in the medium.

The product is stable in plasma.

FIG. 1 illustrates the results obtained with the derivative 48b.

This FIG. 1 shows the concentrations, as a function of time, of daunorubicin (1), the derivative 8b (2) (anthracycline prodrug according to the invention) and the intermediate daunorubicin+self-sacrificing arm (deglycosidated derivative) (3).

Results obtained with the derivative 60 (FIG. 2):

This derivative is incubated with α-galactosidase (unroasted coffee beans, 0.04 U/ml) at 37° C. and pH 6.8 (0.02M phosphate buffer).

These results are determined by HPLC (daunorubicin: $t_r$=8.5 min; 60: $t_r$=11.0 min); the concentration of the derivative 60 is 660 µg/ml.

At pH 6.8 the deglycosidated derivative 60 is not detected because of its high rate of disappearance.

Results obtained with the derivative 54c (FIGS. 3 and 4):

FIG. 3 shows the results obtained when the derivative 54c is incubated with concentrated recombinant human β-glucuronidase at 37° C. and pH 7.2. The concentration of 54c is 530 µg/ml. The results were determined by HPLC (daunorubicin: $t_r$=8.8 min; 54c: $t_r$=9.7 min; deglycosidated 54c: $t_r$=16.0 min).

FIG. 4 shows the results obtained in the presence of β-glucuronidase diluted to 1/100 (other conditions identical to those of FIG. 3).

At pH 7.2 the deglycosidated derivative 54 has a half-life of the order of 5.3 h.

Results obtained with the derivative 70c (FIG. 5): FIG. 5 shows the results obtained when derivative 70c is incubated with human beta-glucuronidase (0,45 U/ml) at 37° C. and pH 7.2.

II. Proliferation test:

A. Experimental protocol (MTT reduction):

L1210 tumoral cells, at a density of $5.10^3$/ml in an RPMI medium, are incubated in microtitre plates containing 96 wells for 72 hours (37° C., 5% $CO_2$, 95% relative humidity) with different prodrugs according to the invention.

The controls consist of tumoral cells exposed to a culture medium. Four wells are prepared for each anthracycline concentration and for the control. After 65 hours, 50 µl of MTT (2.5 mg/ml in PBS) are added.

The MTT will be reduced in the presence of living cells to an insoluble red formazan dye. After incubation for a further 7 to 24 hours (depending on the cells used), the supernatant is removed. The formazan dye is solubilized by the addition of 100 µl of DMSO to each well, followed by gentle shaking.

The extinction is measured for each well at 492 nm (Multiscan 340 CC Fa. Flow photometer).

B. Results:

The results are expressed as the ratio of the extinction after incubation with the prodrugs to the extinction obtained with the controls. The coefficient of variation is less than 15%. The prodrugs have a considerably reduced cytotoxicity compared with doxorubicin.

| Product tested | L1210 $IC_{50}$ (µg/ml) |
| --- | --- |
| doxorubicin | 0.02 |
| derivative 6 | >1 |
| derivative 7 | >1 |
| derivative 13 | >1 |
| derivative 14 | >1 |
| derivative 22 | >10 |
| derivative 27c | >1 |
| derivative 48b | >1 |
| derivative 48a | >10 |

The acetates 6, 13 and 48a are hydrolyzed in vivo to 7, 14 and 48b respectively.

III. Comparison of the cleavability of glycosylated prodrugs according to the invention with that of glycosylated drugs, and influence of the structure of the arm on the rate of cleavage of the glycosyl and the rate of elimination of the self-sacrificing arm:

Prodrugs according to the invention of the daunomycin/self-sacrificing arm/β-glucuronide, doxorubicin/self-sacrificing arm/β-glucuronide and doxorubicin/self-sacrificing arm/α-galactoside type are synthesized by the method described above.

The substances are incubated at 37° C. with recombinant β-glucuronidase (or α-galactosidase from coffee beans) (1 U/ml) at a pH of 7.2 to 6.8 and the kinetics of disappearance of the glycoside and the kinetics of formation of the daunomycin and doxorubicin are determined in vitro by means of reversed-phase HPLC. The time for cleavage of 50% of the glycoside and the time for conversion of 50% of the anthracycline/arm compound to active anthracycline are indicated in Table I below, which refers to the following formula:

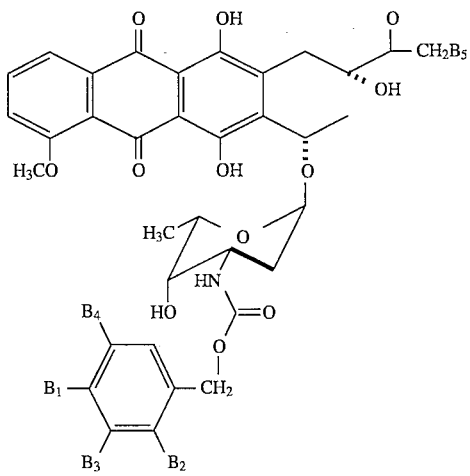

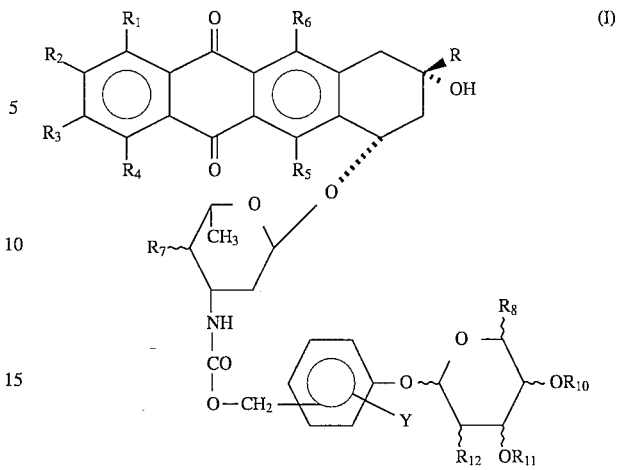

TABLE I

| Substance | $B_1$ | $B_2$ | $B_3$ | $B_4$ | $t_{1/2}$ cleavage of the glycoside (h) | $t_{1/2}$ arm (h) |
|---|---|---|---|---|---|---|
| $B_5$ = H (daunomycin) | | | | | | |
| 1 (68c) | $OCH_3$ | β-Gluc | H | $NO_2$ | 1,88 | 0,75 |
| 2 (54c) | H | β-Gluc | H | $NO_2$ | 0,69 | 5,30 |
| 3 (82c) | H | β-Gluc | H | Cl | 4,06 | 12,00 |
| 4 (64c) | β-Gluc | H | H | $NO_2$ | 0,42 | <0,08 |
| 5 (60) | α-Gal | H | H | Cl | 0,02 | <0,08 |
| $B_5$ = OH (doxorubicin) | | | | | | |
| 6 (70c) | H | β-Gluc | H | $NO_2$ | 0,92 | n.t. |

β-Glucuronide not carrying an arm, which serves as the comparison substance, is cleaved 50 to 100 times less rapidly than the daunomycin/arm/glucuronide compounds or than the doxorubicine/arm/glucuronide compounds. This indicates that the presence of a self-sacrificing arm appropriate for the cleavage of the glucuronide/prodrug compound is of decisive importance. Furthermore, the substituents present on the aromatic cycle of this self-sacrificing arm (hydroxybenzyl carbamates, for example) influence the kinetics of the cleavage of the glycosylated derivative and the kinetics of the decomposition of the product anthracycline+self-sacrificing arm. A more rapid cleavage of the glycosyl and a more rapid automatic elimination of the arm are found for the prodrugs according to the invention in which $B_1$ is a β-glucuronide and $B_4$ is an $NO_2$ group or a chlorine atom. Other substituents also make it possible to obtain the desired kinetics.

As is apparent from the foregoing description, the invention is in no way limited to those modes of execution, embodiments and modes of application which have now been described more explicitly; on the contrary, it encompasses all the variants thereof which may occur to those skilled in the art, without deviating from the framework or the scope of the present invention.

We claim:

1. An anthracycline prodrug having the formula:

wherein $R_1$, $R_2$ and $R_3$, which are identical or different from each other, are hydrogen or hydroxyl;

$R_4$ is hydrogen, hydroxyl or methoxy;

R is $CO-CH_2-R''$, wherein R" is hydrogen, $C_1-C_6$-alkyl, hydroxyl, alkoxy, O-acyl or aryl;

$R_5$ and $R_6$, which are identical or different from each other, are hydrogen or hydroxyl;

$R_7$ is hydrogen or hydroxyl;

$R_8$ is $-CH_2OR_9$ or $-COOR_9$, wherein $R_9$ is $C_1-C_3$-alkyl or hydrogen;

$R_{10}$ and $R_{11}$ are hydrogen, alkyl or an acyl protecting group;

$R_{12}$ is hydroxyl, amine, amide or an O-acyl protecting group;

Y is at least one member selected from the group consisting of hydrogen, nitro, halogen, $SO_2X$, CN, acyl, COO-alkyl, O-alkyl, NHCO-alkyl, N(alkyl)CO-alkyl, S-alkyl and alkyl, wherein X is $CH_3$, $C_6H_4CH_3$, $NH_2$, $N(C_1-C_4$-alkyl$)_2$ or $NH-C_1-C_4$-alkyl.

2. The prodrug of claim 1, wherein Y is one or more members selected from the group consisting of $NO_2$, halogen, $SO_2X$, CN, acyl and COO-alkyl and Y is in the ortho position, para position or both ortho and para positions relative to a glycosyl oxygen, or Y is one or more members selected from the group consisting of O-alkyl, NHCO-alkyl, N(alkyl)CO-alkyl, S-alkyl and alkyl and Y is in the meta position relative to a glycosyl oxygen.

3. The prodrug of claim 1, wherein:

$R_1$, $R_2$ and $R_3$ are hydrogen;

$R_4$ is methoxy;

$R_5$ and $R_6$ are hydroxyl;

R is $-CO-CH_3$ or $-CO-CH_2OH$;

$R_7$ is hydrogen or hydroxyl;

$R_8$ is $-CH_2-OAc$, $-CH_2OH$, $-COOMe$ or COOH;

$R_{10}$ and $R_{11}$, which are identical or different from each other, are hydrogen or an Ac group;

$R_{12}$ is hydroxyl or an OAc group; and

Y is hydrogen, $NO_2$ or chlorine in the ortho or para position relative to a glycosyl oxygen, or $OCH_3$ in the meta position to a glycosyl oxygen.

4. The prodrug of claim 3, wherein $R_8$, $R_{10}$, $R_{11}$ and $R_{12}$ have the stereochemistry shown below:

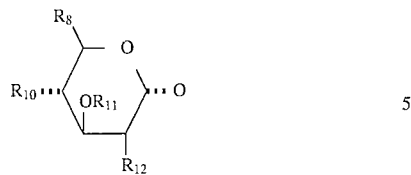
5. The prodrug of claim 1, having the formula shown below:
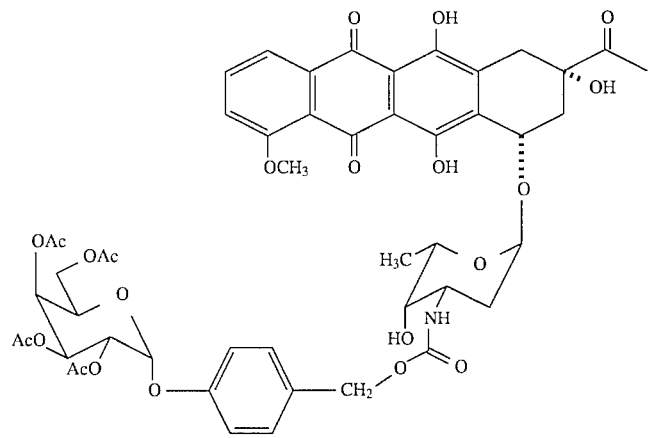
6. The prodrug of claim 1, having the formula shown below:
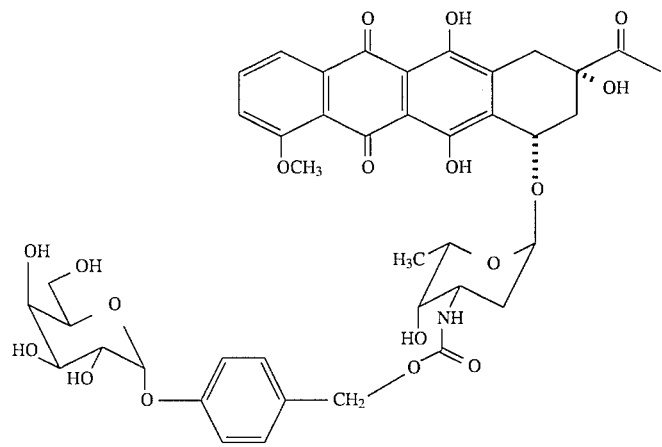
7. The prodrug of claim 1, having the formula shown below:

8. The prodrug of claim 1, having the formula shown below:
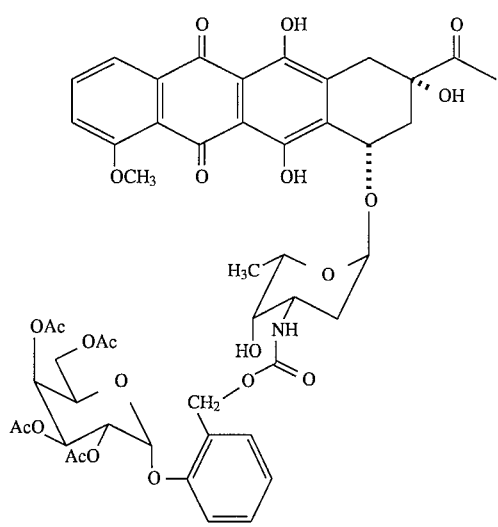
9. The prodrug of claim 1, having the formula shown below:
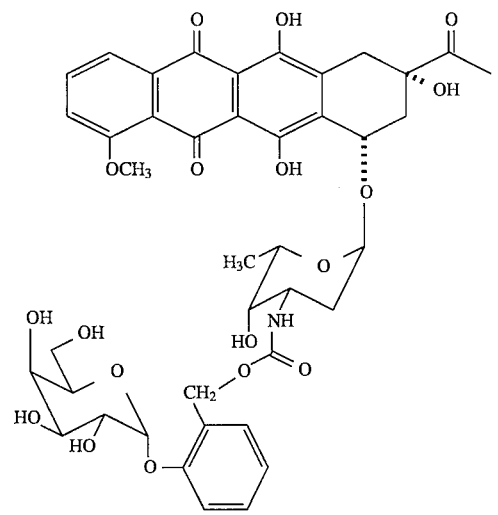
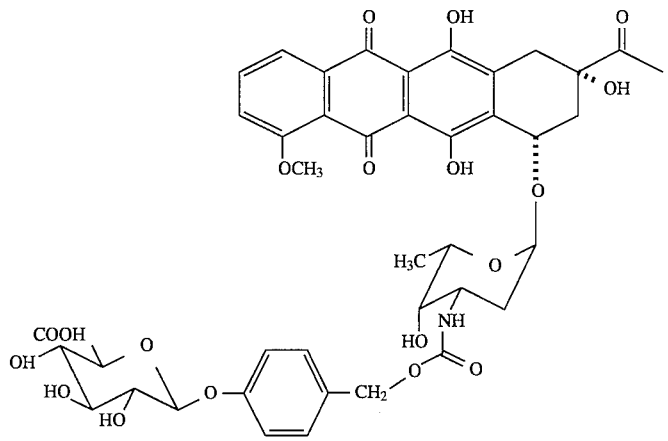
10. The prodrug of claim 1, having the formula shown below:
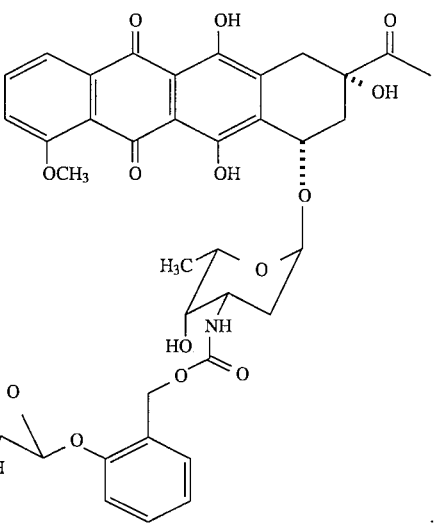
11. The prodrug of claim 1, having the formula shown below:

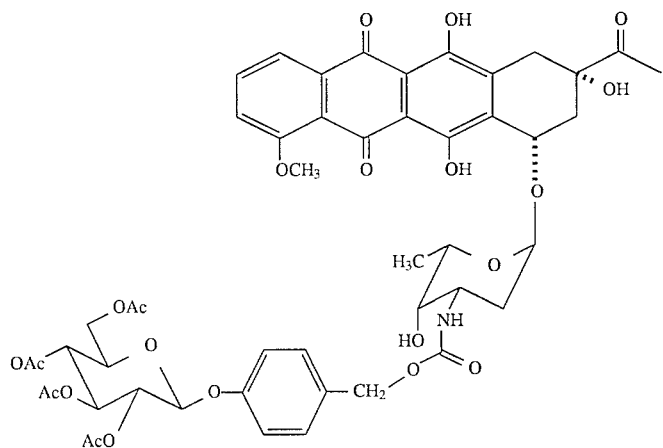
12. The prodrug of claim 1, having the formula shown below:
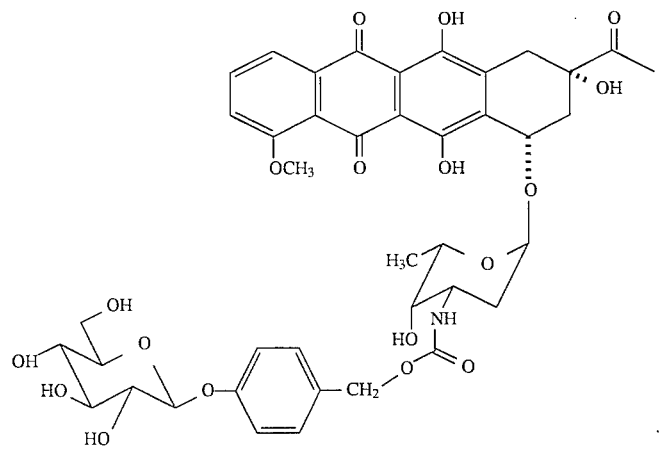
13. The prodrug of claim 1, having the formula shown below:
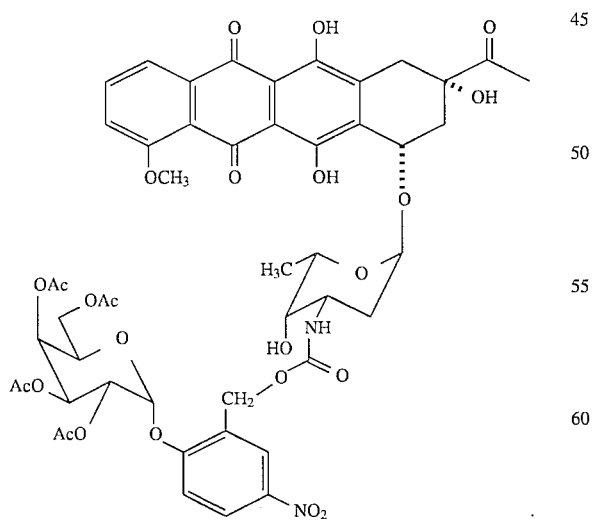
14. The prodrug of claim 1, having the formula shown below:
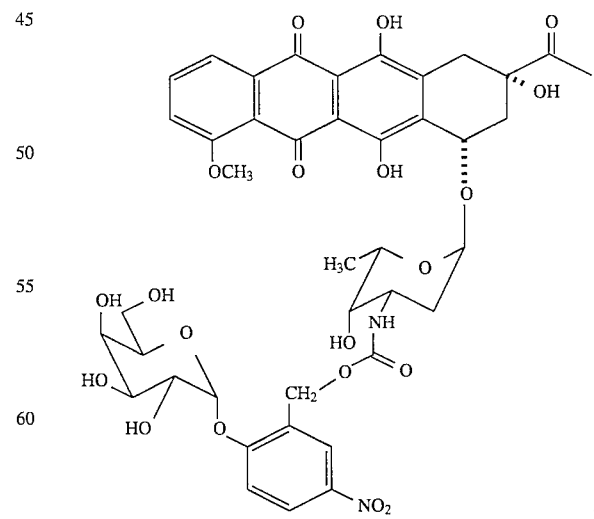
15. The prodrug of claim 1, having the formula shown below:

73
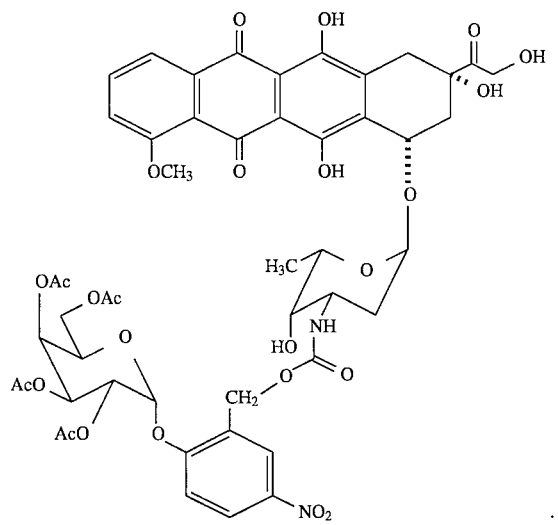
16. The prodrug of claim 1, having the formula shown below:
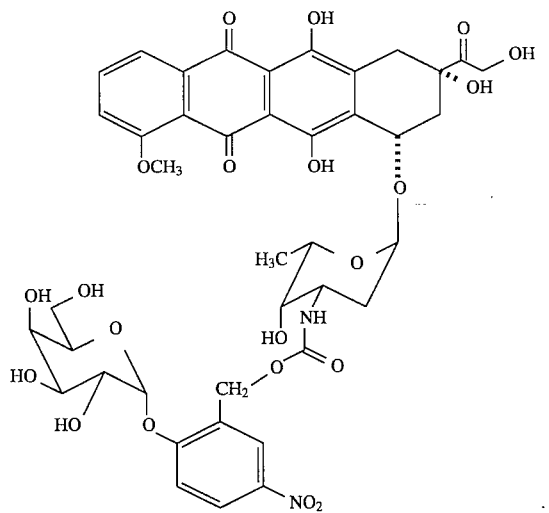
17. The prodrug of claim 1, having the formula shown below:
74
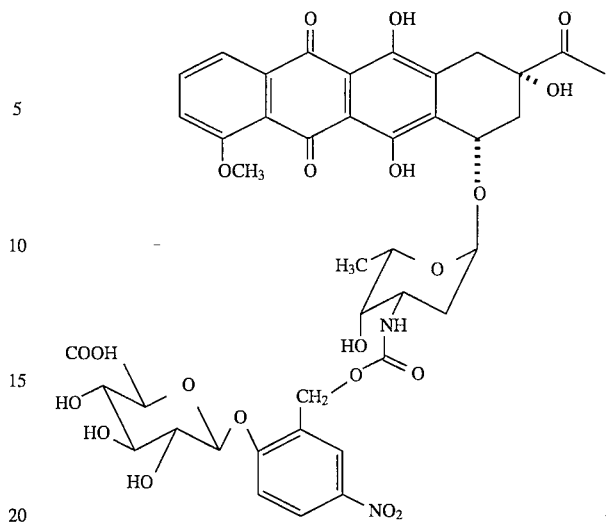
18. The prodrug of claim 1, having the formula shown below:
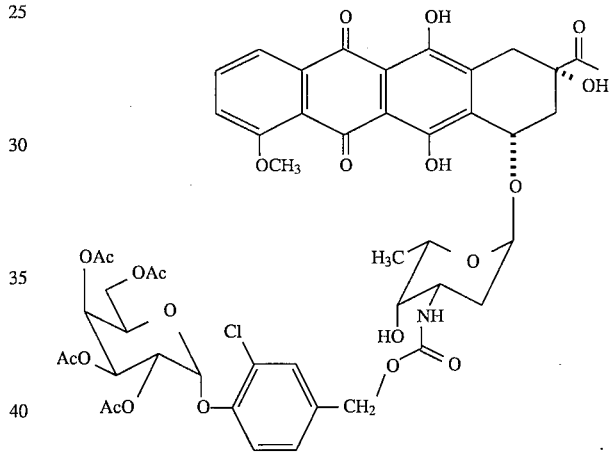
19. The prodrug of claim 1, having the formula shown below:

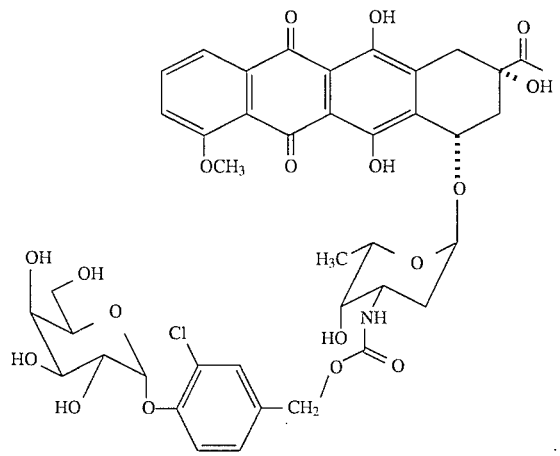
20. The prodrug of claim 1, having the formula shown below:
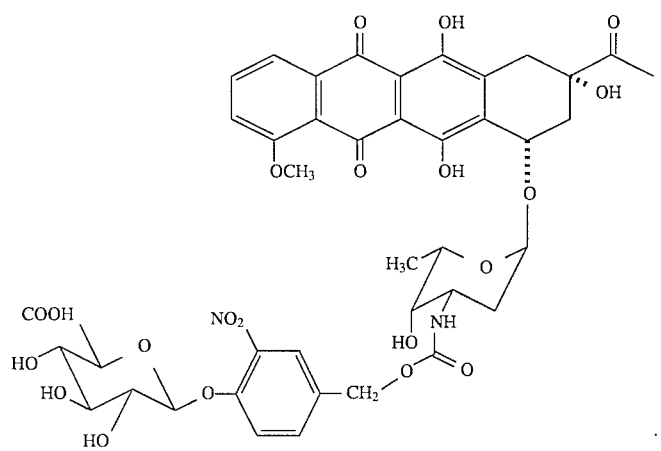
21. The prodrug of claim 1, having the formula shown below:
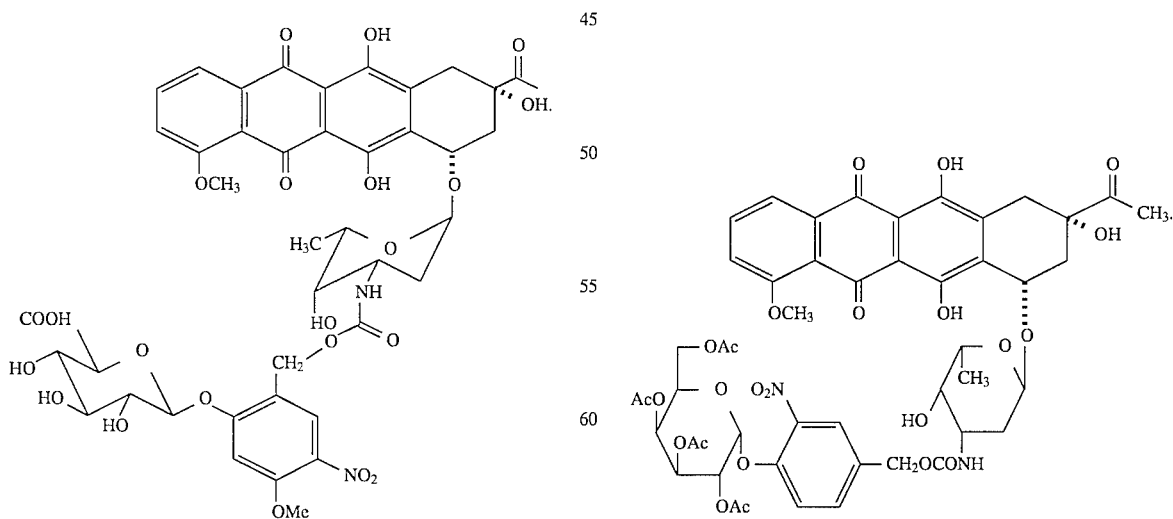
22. The prodrug of claim 1, having the formula shown below:
23. The prodrug of claim 1, having the formula shown below:

24. The prodrug of claim 1, having the formula shown below:
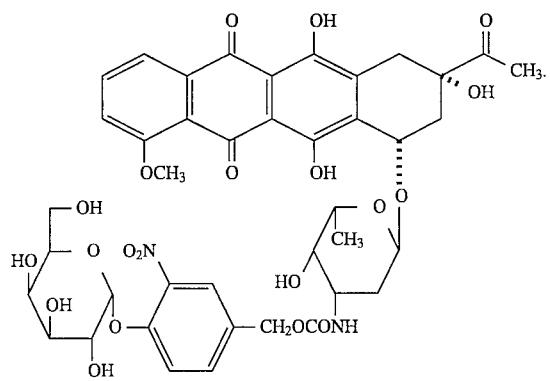
25. The prodrug of claim 1, having the formula shown below:
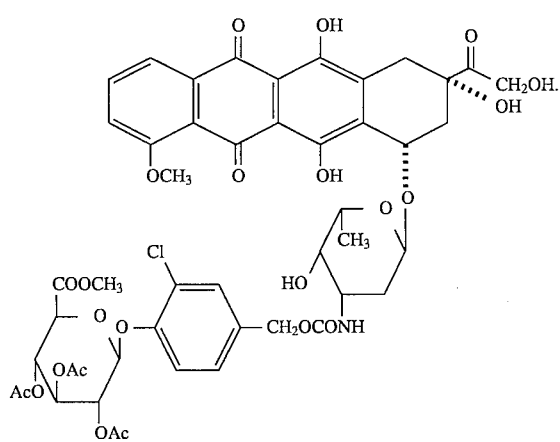
26. The prodrug of claim 1, having the formula shown below:
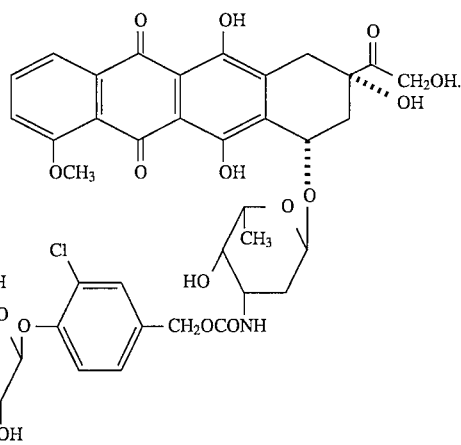
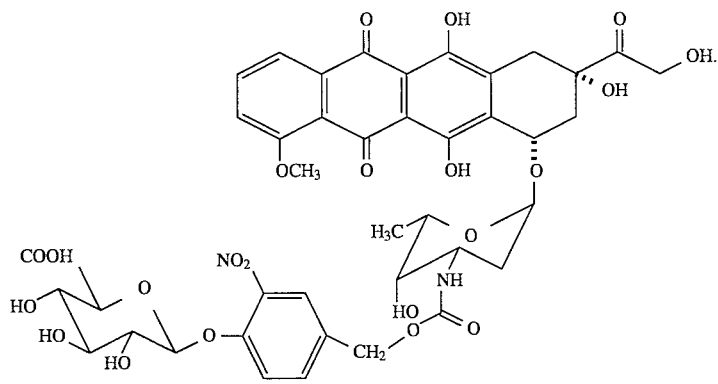
27. The prodrug of claim 1, having the formula shown below:

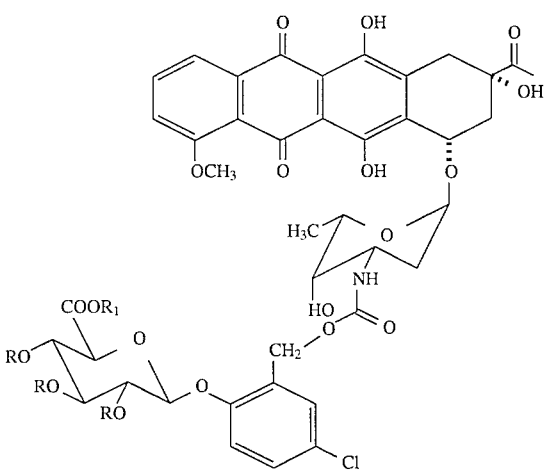

wherein either (a) R is Ac and $R_1$ is $CH_3$; or
(b) R is H and $R_1$ is $CH_3$; or
(c) R and $R_1$ are H.

28. The prodrug of claim 1, having the formula shown below:

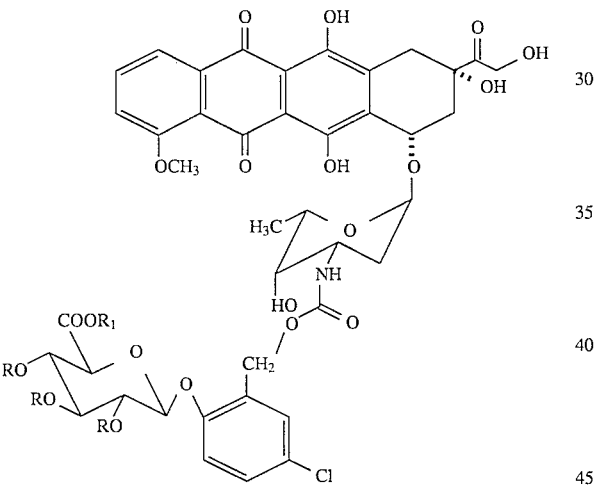

wherein either (a) R is Ac and $R_1$ is $CH_3$; or
(b) R is H and $R_1$ is $CH_3$; or
(c) R and $R_1$ are H.

29. A compound selected from the group consisting of 4-bromomethylphenyl 2,3,4,6-tetra-O-acetyl-α-D-galactopyranoside,
4-formylphenyl 2,3,4,6-tetra-O-acetyl-α-D-galactopyranoside,
4-hydroxymethylphenyl 2,3,4,6-tetra-O-acetyl-α-D-galactopyranoside,
2-bromomethylphenyl 2,3,4,6-tetra-O-acetyl-α-D-galactopyranoside,
2-formylphenyl 2,3,4,6-tetra-O-acetyl-α-D-galactopyranoside,
2-hydroxymethylphenyl 2,3,4,6-tetra-O-acetyl-α-D-galactopyranoside,
methyl (4-bromomethylphenyl 2,3,4-tri-O-acetyl-β-D-glucopyranoside)uronate,
methyl (4-formylphenyl 2,3,4-tri-O-acetyl-β-D-glucopyranoside)uronate,
methyl (4-hydroxymethylphenyl 2,3,4-tri-O-acetyl-β-D-glucopyranoside)uronate,
methyl (2-bromomethylphenyl 2,3,4-tri-O-acetyl-β-D-glucopyranoside)uronate,
methyl (2-hydroxymethylphenyl 2,3,4-tri-O-acetyl-β-D-glucopyranoside)uronate,
methyl (2-formylphenyl 2,3,4-tri-O-acetyl-β-D-glucopyranoside)uronate,
N-(2-hydroxybenzyloxycarbonyl)daunorubicin,
N-(4-hydroxybenzyloxycarbonyl)daunorubicin,
2-methyl-4-nitrophenyl 2,3,4,6-tetra-O-acetyl-α-D-galactopyranoside,
2-bromomethyl-4-nitrophenyl 2,3,4,6-tetra-O-acetyl-α-D-galactopyranoside,
2-dibromomethyl-4-nitrophenyl 2,3,4,6-tetra-O-acetyl-α-D-galactopyranoside,
2-formyl-4-nitrophenyl 2,3,4,6-tetra-O-acetyl-α-D-galactopyranoside,
2-hydroxymethyl-4-nitrophenyl 2,3,4,6-tetra-O-acetyl-α-D-galactopyranoside,
methyl (2-formyl-4-nitrophenyl 2,3,4-tri-O-acetyl-β-D-glucopyranoside)uronate,
methyl (2-hydroxymethyl-4-nitrophenyl 2,3,4-tri-O-acetyl-β-D-glucopyranoside)uronate,
2-chloro-4-methylphenyl 2,3,4,6-tetra-O-acetyl-α-D-galactopyranoside,
2-chloro-4-bromomethylphenyl 2,3,4,6-tetra-O-acetyl-α-D-galactopyranoside,
2-chloro-4-hydroxymethylphenyl 2,3,4,6-tetra-O-acetyl-α-D-galactopyranoside,
methyl (4-formyl-2-nitrophenyl 2,3,4-tri-O-acetyl-β-D-glucopyranoside)uronate,
methyl (4-hydroxymethyl-2-nitrophenyl 2,3,4-tri-O-acetyl-β-D-glucopyranoside)uronate,
4-bromomethyl-2-nitrophenyl 2,3,4,6-tetra-O-acetyl-α-D-galactopyranoside,
4-hydroxymethyl-2-nitrophenyl 2,3,4,6-tetra-O-acetyl-α-D-galactopyranoside,
4-hydroxy-3-chlorobenzaldehyde 2,3,4-tri-O-acetyl-β-D-methylglucuronide,
4-hydroxymethyl-2-chlorophenyl 2,3,4-tri-O-acetyl-β-D-methylglucuronide,
2,5-dioxopyrrolidin-1-yl 4-(2,3,4,6-tetra-O-acetyl-α-D-galactopyranosyl)benzyl carbonate,
2,5-dioxopyrrolidin-1-yl 2-(2,3,4,6-tetra-O-acetyl-α-D-galactopyranosyl)benzyl carbonate,
2,5-dioxopyrrolidin-1-yl 4-(methyl(2,3,4-tri-O-acetyl-β-D-glucopyranosyl)uronate)benzyl carbonate,
4-nitrophenyl 2-(methyl(2,3,4-tri-O-acetyl-β-D-glucopyranosyl)uronate) benzyl carbonate,
4-nitrophenyl 2-(tert-butyldimethylsiloxy)benzyl carbonate,
2,5-dioxopyrrolidin-1-yl 4-(2,3,4,6-tetra-O-acetyl-β-D-glucopyranosyl)benzyl carbonate,
2,5-dioxopyrrolidin-1-yl 4-dimethyl-t-hexylsilyloxybenzyl carbonate,
4-nitrophenyl 2-(2,3,4,6-tetra-O-acetyl-α-D-galactopyranosyl)-5-nitrobenzyl carbonate,
4-nitrophenyl 2-(methyl(2,3,4-tri-O-acetyl-β-D-glucopyranosyl)uronate)-5-nitrobenzyl carbonate, 4-nitrophenyl 4-methoxy-5-nitro-2-(methyl(2,3,4-tri-O-acetyl-β-D-glucopyranosyl)uronate)benzyl carbonate, 4-nitrophenyl 4-(methyl(2,3,4-tri-O-acetyl-β-D-glucopyranosyl)uronate)-5-nitrobenzyl carbonate, and 4-chlorophenyl 2-(methyl(2,3,4-tri-O-acetyl-β-D-glucopyranosyl)uronate)-5-nitrobenzyl carbonate.

30. A method of treating a disease involving activated macrophages, granulocytes, thrombocytes or human tumoral cells, comprising administering to a patient in need thereof an effective amount of the prodrug of claim 1.

31. A composition comprising the prodrug of claim 1 and a conjugate having the formula
wherein:

Ab is an antibody or antibody fragment having specificity to a tumor antigen, or Ab is a compound which accumulates in a tumor selected from the group consisting of epidermal growth factor, α-transforming growth factor, platelet derived growth factor, insulin growth factor I, insulin growth factor II, fibroblast growth factor a, and fibroblast growth factor b;

E is a mammalian glycosidase selected from the group consisting of α-galactosidase, β-glucuronidase, α-fucosidase, α-mannosidase, β-mannosidase, α-glucosidase, β-glucosidase, β-glucocerebrosidase, α-N-acetylglucosaminidase, β-acetylglucosaminidase, and α-N-acetylgalactosaminidase; and Sp is a polypeptide or Sp is a sulfide of disulfide selected from the group consisting X'—S—Y', X'—S—S—Y', X'—S, or X'—S—S, wherein X' and Y' are each CO—R$_{13}$—(N-succinimido) or C(=R$_{14}$)—CH$_2$—CH$_2$, wherein R$_{13}$ is CH$_2$CH$_2$, 1,4-cyclohexylidene, 1,3-phenylene, 1,4-phenylene, methoxycarbonyl-1,4-phenylene, or chloro-1,4-phenylene, and wherein R$_{14}$ is O or NH.

32. A method for reducing the growth of a tumor, comprising administering to a patient in need thereof an effective amount of the composition of claim 31.

33. A method of preparing an anthracycline prodrug, wherein said method comprises:

(1) coupling of a compound having the formula shown below:

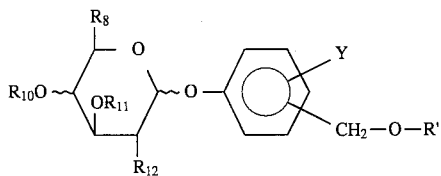

wherein

R$_8$ is —CH$_2$OR$_9$ or —COOR$_9$, wherein R$_9$ is C$_1$–C$_3$ alkyl or hydrogen;

R$_{10}$ and R$_{11}$ are hydrogen, alkyl or an acyl protecting group;

R$_{12}$ is hydroxyl, amine, amide or an O-acyl protecting group;

R' is one of the following groups:

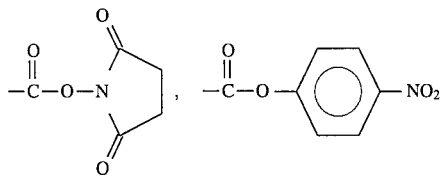

and

Y is one or more members selected from the group consisting of NO$_2$, halogen, hydrogen and OCH$_3$, with an anthracycline having the following formula:

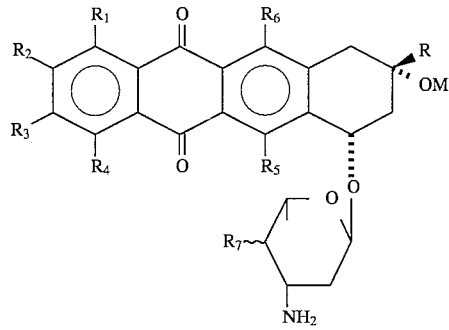

wherein

R$_1$, R$_2$ and R$_3$, which are identical or different from each other, are hydrogen or hydroxyl;

R$_4$ is hydrogen, hydroxyl or methoxy;

R is CO—CH$_2$—R", where R" is hydrogen, C$_1$–C$_6$ alkyl, hydroxyl, alkoxy, O-acyl or aryl;

R$_5$ and R$_6$, which are identical or different from each other, are hydrogen or hydroxyl;

R$_7$ is hydrogen or hydroxyl; and (2) removing protecting groups present in the compounds obtained, wherein said coupling results in formation of an amide linkage between the nitrogen atom of said anthracycline and the carbonyl group of the ester moiety of R'.

34. The method according to claim 33, wherein prior to step (1), said compound of formula:

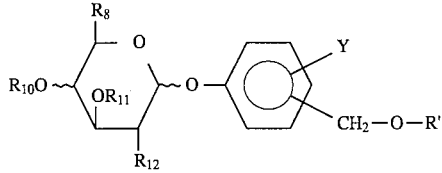

is obtained by:

(a) reaction of a cresol with a compound selected from the group consisting of an acetyl-D-galactopyranose, a peracetylated methyl glucuronate and a peracetyl-D-glucose to form a glycoside product, (b) benzyl bromination of the product obtained in (a), (c) solvolysis of the brominated derivative, and (d) activation of the hydroxyl group with a hydroxysuccinimidyl or paranitrophenoxycarbonyl derivative.

35. A method of preparing an anthracycline prodrug of claim 1, wherein said method comprises:

(1) coupling of a silylated compound having the formula shown below:

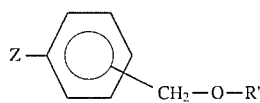

wherein

Z is O-dimethylthexylsilyl or O-tert-butyldimethylsilyl, and

R' is one of the following groups:

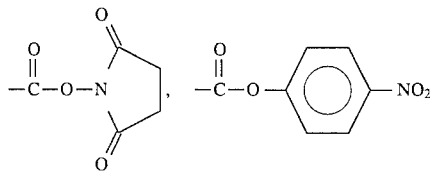

with an anthracycline having the following formula:

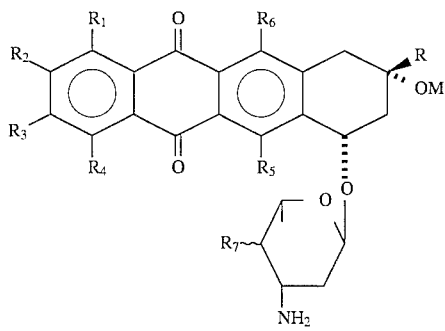

wherein $R_1$, $R_2$ and $R_3$, which are identical or different from each other, are hydrogen or hydroxyl;

$R_4$ is hydrogen, hydroxyl or methoxy;

R is CO—$CH_2$—R", wherein R" is hydrogen, $C_1$–$C_6$ alkyl, hydroxyl, alkoxy, O-acyl or aryl;

$R_5$ and $R_6$, which are identical or different from each other, are hydrogen or a hydroxyl; and $R_7$ is hydrogen or hydroxyl;

(2) removing protecting groups present in the compounds obtained, and (3) condensing the compound obtained in (2) with a derivative having the following formula:

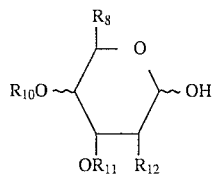

wherein $R_8$ is —$CH_2OR_9$ or —$COOR_9$, wherein $R_9$ is $C_1$–$C_3$ alkyl or hydrogen;

$R_{10}$ and $R_{11}$ are hydrogen, alkyl or an acyl protecting group; and $R_{12}$ is hydroxyl, amine, amide or an O-acyl protecting group.

36. A method of preparing an anthracycline prodrug of claims 13, 14, 15, 16, 17, 21, 27 or 28, wherein said method comprises:

(1) coupling of a compound having the formula shown below:

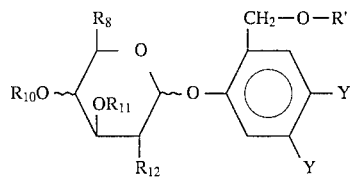

wherein $R_8$ is —$CH_2OR_9$ or —$COOR_9$, wherein $R_9$ is $C_1$–$C_3$ alkyl or hydrogen;

$R_{10}$ and $R_{11}$ are hydrogen, alkyl or an acyl protecting group;

$R_{12}$ is hydroxyl, amine, amide or an O-acyl protecting group;

R' is one of the following groups:

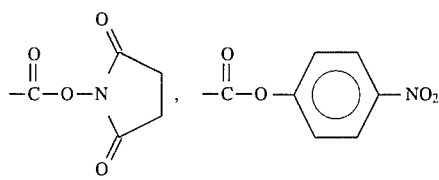

and

Y is one or more members selected from the group consisting of $NO_2$ and halogen, and Y is in a para position relative to a glycosyl oxygen; or Y is one or more members selected from the group consisting of hydrogen and $OCH_3$ and Y is in a meta position relative to a glycosyl oxygen, with an anthracycline having the following formula:

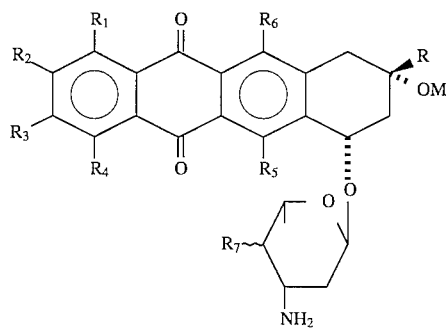

wherein $R_1$, $R_2$ and $R_3$, which are identical or different from each other, are hydrogen or hydroxyl;

$R_4$ is hydrogen, hydroxyl or methoxy;

R is CO—$CH_2$—R", where R" is hydrogen, $C_1$–$C_6$ alkyl, hydroxyl, alkoxy, O-acyl or aryl;

$R_5$ and $R_6$, which are identical or different from each other, are hydrogen or hydroxyl; and $R_7$ is hydrogen or hydroxyl; and (2) removing protecting groups present in the compounds obtained.

* * * * *